United States Patent [19]

Enari et al.

[11] Patent Number: 4,668,815
[45] Date of Patent: May 26, 1987

[54] DERIVATIVES OF PHENYLACETIC ESTER, A PROCESS FOR PRODUCING THE SAME AND INSECTICIDAL COMPOSITIONS CONTAINING THE SAME AS AN ACTIVE INGREDIENT

[75] Inventors: Hiroyuki Enari; Yutaka Konai; Uichi Akiba; Masayo Ito, all of Iwaki, Japan

[73] Assignee: Kureha Kagaku Kogyo Kabushiki Kaisha, Tokyo, Japan

[21] Appl. No.: 751,313

[22] Filed: Jul. 2, 1985

[30] Foreign Application Priority Data

Jul. 6, 1984 [JP] Japan ................................ 59-140250

[51] Int. Cl.$^4$ .............................................. C07C 69/76
[52] U.S. Cl. ...................................................... 560/55
[58] Field of Search .......................... 560/55; 574/532

[56] References Cited

FOREIGN PATENT DOCUMENTS 3230775 2/1984 Fed. Rep. of Germany .

Primary Examiner—Paul J. Killos
Attorney, Agent, or Firm—John P. White

[57] ABSTRACT

Disclosed herein are derivatives of phenylacetic ester represented by the formula (I):

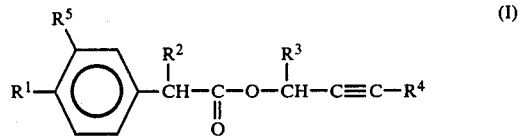

wherein $R^1$ represents a halogen atom or a lower alkoxy group; $R^2$ represents a lower alkyl group; $R^3$ represents a hydrogen atom or a methyl group; $R^4$ represents a hydrogen atom, a lower alkyl group, $$-CH_2-CH=CH_2, -CH_2-CH=CH-CH_3,$$

$$-CH_2-\underset{\underset{CH_3}{|}}{C}=CH_2, -CH_2OCH_3, -CH_2OCH_2CH_3,$$

$$-CH_2-O-CH_2-CH=CH_2, -CH_2-O-CH_2-C\equiv CH,$$
$$-CH_2-O-CH_2-C\equiv C-CH_3, -COCH_3,$$

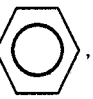

and $R^5$ represents a hydrogen atom or a halogen atom, a process for producing the derivatives and an insecticidal composition containing the derivatives of phenylacetic ester as an active ingredient.

37 Claims, 82 Drawing Figures

DERIVATIVES OF PHENYLACETIC ESTER, A PROCESS FOR PRODUCING THE SAME AND INSECTICIDAL COMPOSITIONS CONTAINING THE SAME AS AN ACTIVE INGREDIENT

BACKGROUND OF THE INVENTION

The present invention relates to derivatives of phenylacetic ester, represented by the formula (I):

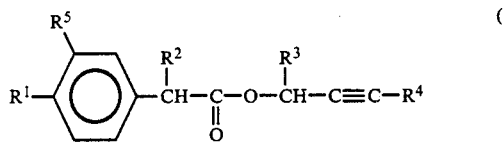

wherein $R^1$ represents a halogen atom or a lower alkoxy group; $R^2$ represents a lower alkyl group; $R^3$ represents a hydrogen atom or a methyl group; $R^4$ represents a hydrogen atom, a lower alkyl group, $-CH_2-CH=CH_2$, $-CH_2-CH=CH-CH_3$,

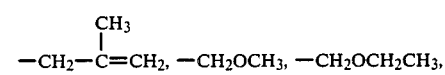

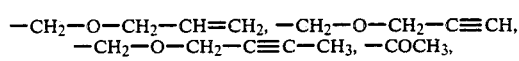

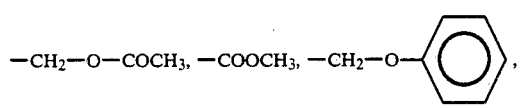

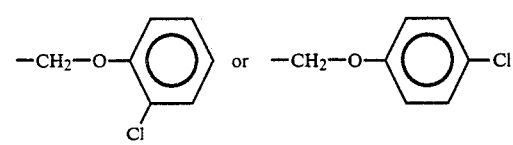

and $R^5$ represents a hydrogen atom or a halogen atom, a process for producing the derivatives and an insecticidal composition containing at least one of the derivatives of phenylacetic ester represented by the formula (I) as an active ingredient.

Although many insecticidally active compounds have been hitherto known, of these compounds, natural pyrethrins and their analogous compounds have been broadly used for controlling noxious insects in sanitation, agriculture and horticulture because of their excellent insecticidal activity as well as the swift activity to noxious insects, the low toxicity to human and animal and the fact that they hardly cause insecticide-resistance in insect species to which the insecticides are applied.

However, since natural pyrethrins are so high in price, it is difficult economically to use natural pyrethrins or their analogous compounds such as allethrin broadly in various fields. In order to dissolve the demerit, many compounds have been synthesized. However, at present a larger part of the thus synthesized compounds are inferior to natural pyrethrins and allethrin in the insecticidal activity and the economical efficiency.

As a result of study for a novel and easily synthesizable insecticidal compound, the present inventors have found that the derivatives of phenylacetic ester represented by the formula (I) has excellent insecticidal properties, more swifter insecticidal activity as compared with allethrin and a reliable lethality to insect which has been quite insufficient in allethrin, and based on the finding, the present inventors have completed the present invention.

SUMMARY OF THE INVENTION

In the first aspect of the present invention, there is provided novel derivatives of phenylacetic ester represented by the formula (I):

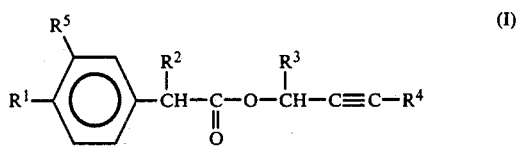

wherein $R^1$ represents a halogen atom or a lower alkoxy group; $R^2$ represents a lower alkyl group; $R^3$ represents a hydrogen atom or a methyl group; $R^4$ represents a hydrogen atom, a lower alkyl group, $-CH_2-CH=CH_2$, $-CH_2-CH=CH-CH_3$,

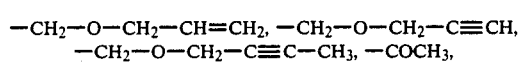

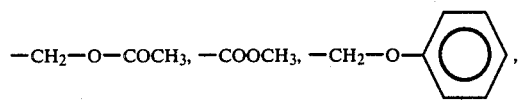

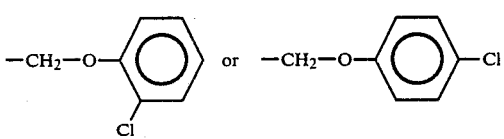

and $R^5$ represents a hydrogen atom or a halogen atom.

In the second aspect of the present invention, there is provided a process for producing a derivative of phenylacetic ester represented by the formula (I):

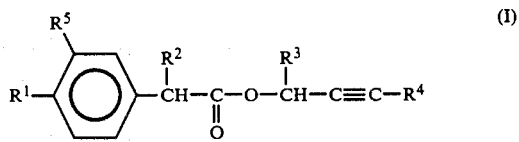

wherein $R^1$ represents a halogen atom or a lower alkoxy group; $R^2$ represents a lower alkyl group; $R^3$ represents a hydrogen atom or a methyl group; $R^4$ represents a hydrogen atom, a lower alkyl group, $-CH_2-CH=CH_2$, $-CH_2-CH=CH-CH_3$,

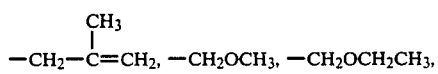

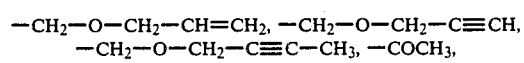

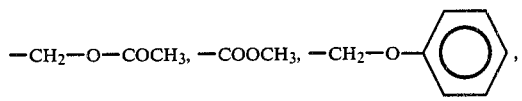

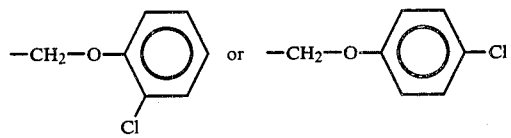

and $R^5$ represents a hydrogen atom or a halogen atom, comprising reacting carboxylic acid halide represented by the following formula (II):

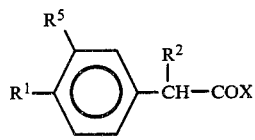
(II)

wherein $R^1$, $R^2$ and $R^5$ are the same as defined above and X represents a halogen atom, with an alcohol represented by the following formula (III):

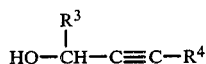
(III)

wherein $R^3$ and $R^4$ are the same as defined above, in a solvent in the presence of a condensing agent.

In the third aspect of the present invention, there is provided an insecticidal composition comprising an insecticidally effective amount of at least one of the derivatives of phenylacetic ester represented by the formula (I) as an active ingredient:

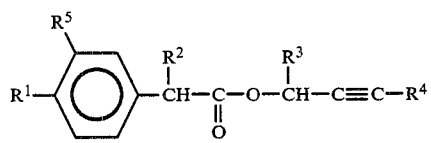
(I)

wherein $R^1$ represents a halogen atom or a lower alkoxy group; $R^2$ represents a lower alkyl group; $R^3$ represents a hydrogen atom or a methyl group; $R^4$ represents a hydrogen atom, a lower alkyl group, $-CH_2-CH=CH_2$, $-CH_2-CH=CH-CH_3$,

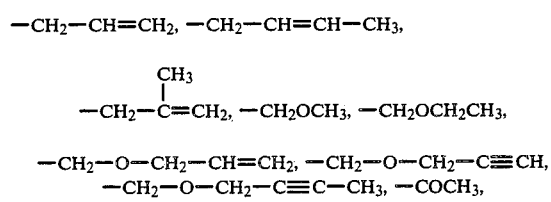

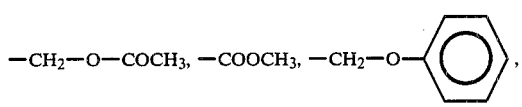

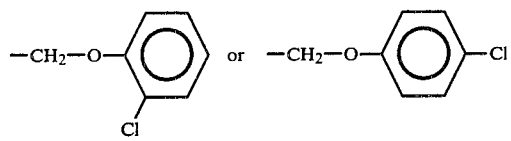

and $R^5$ represents a hydrogen atom or a halogen atom, an insecticidally acceptable carrier and a diluent therefor.

In the fourth aspect of the present invention, there is provided a method for controlling noxious insects, which comprises applying an insecticidally effective amount of a derivative of phenylacetic ester represented by the formula (I):

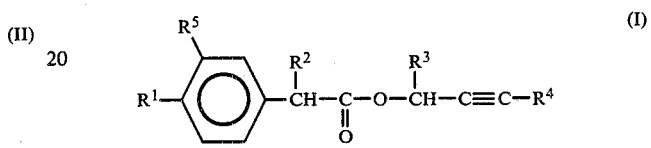
(I)

wherein $R^1$ represents a halogen atom or a lower alkoxy group; $R^2$ represents a lower alkyl group; $R^3$ represents a hydrogen atom or a methyl group; $R^4$ represents a hydrogen atom, a lower akyl group, $-CH_2-CH=CH_2$, $-CH_2-CH=CH-CH_3$,

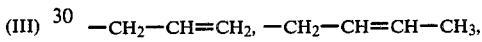
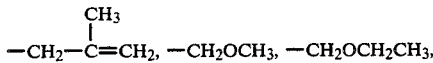

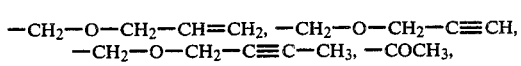

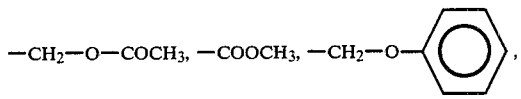

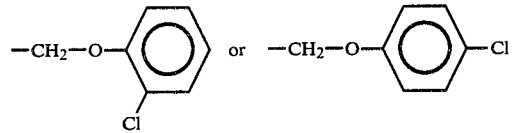

and $R^5$ represents a hydrogen atom or a halogen atom.

BRIEF EXPLANATION OF DRAWINGS

Of the attached drawings.

DETAILED DESCRIPTION OF THE INVENTION

Figure 1:
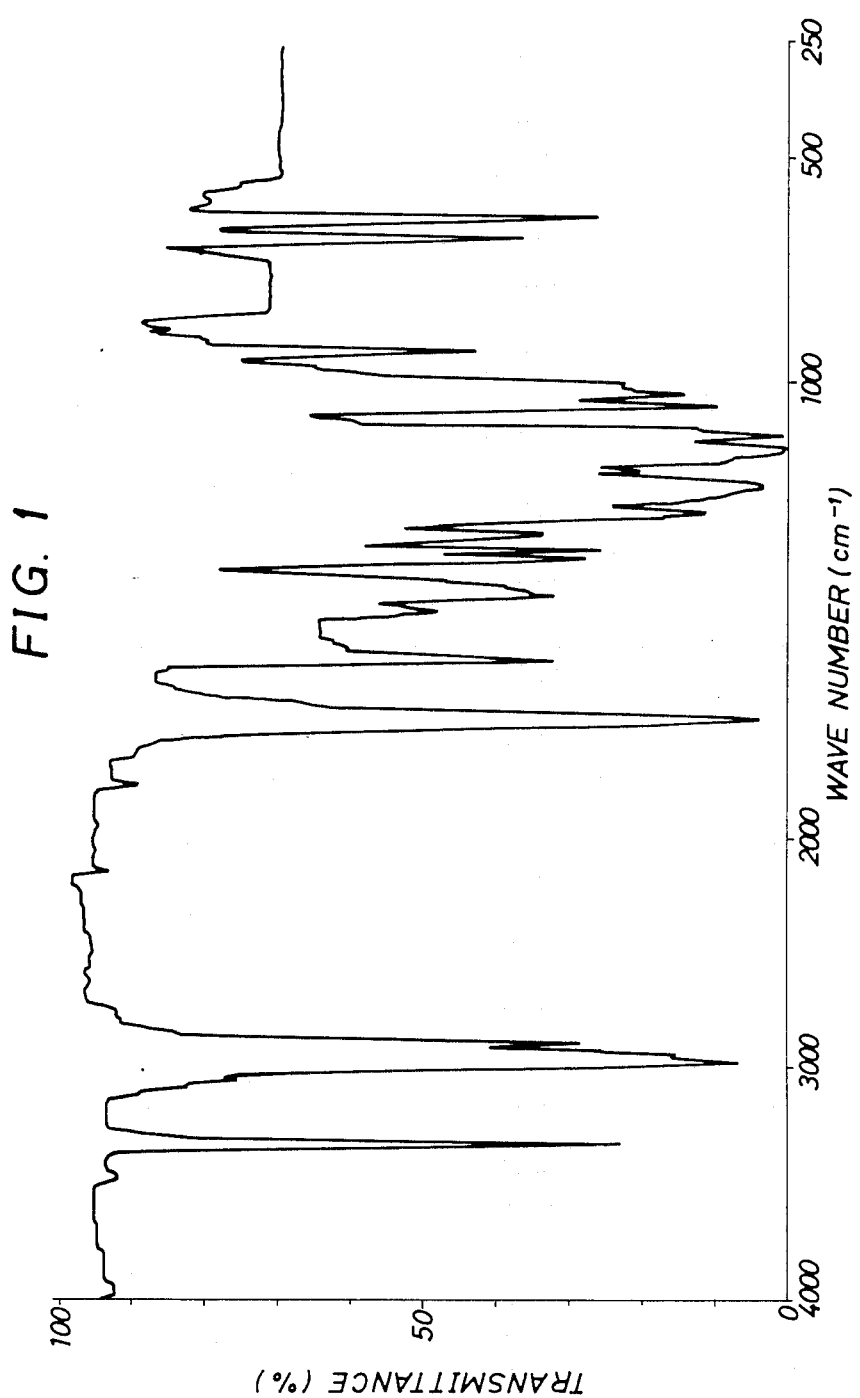
FIGS. 1 to 41 are the infrared absorption spectra of the compounds, derivatives of phenylacetic ester of the present invention.
Figure 2:
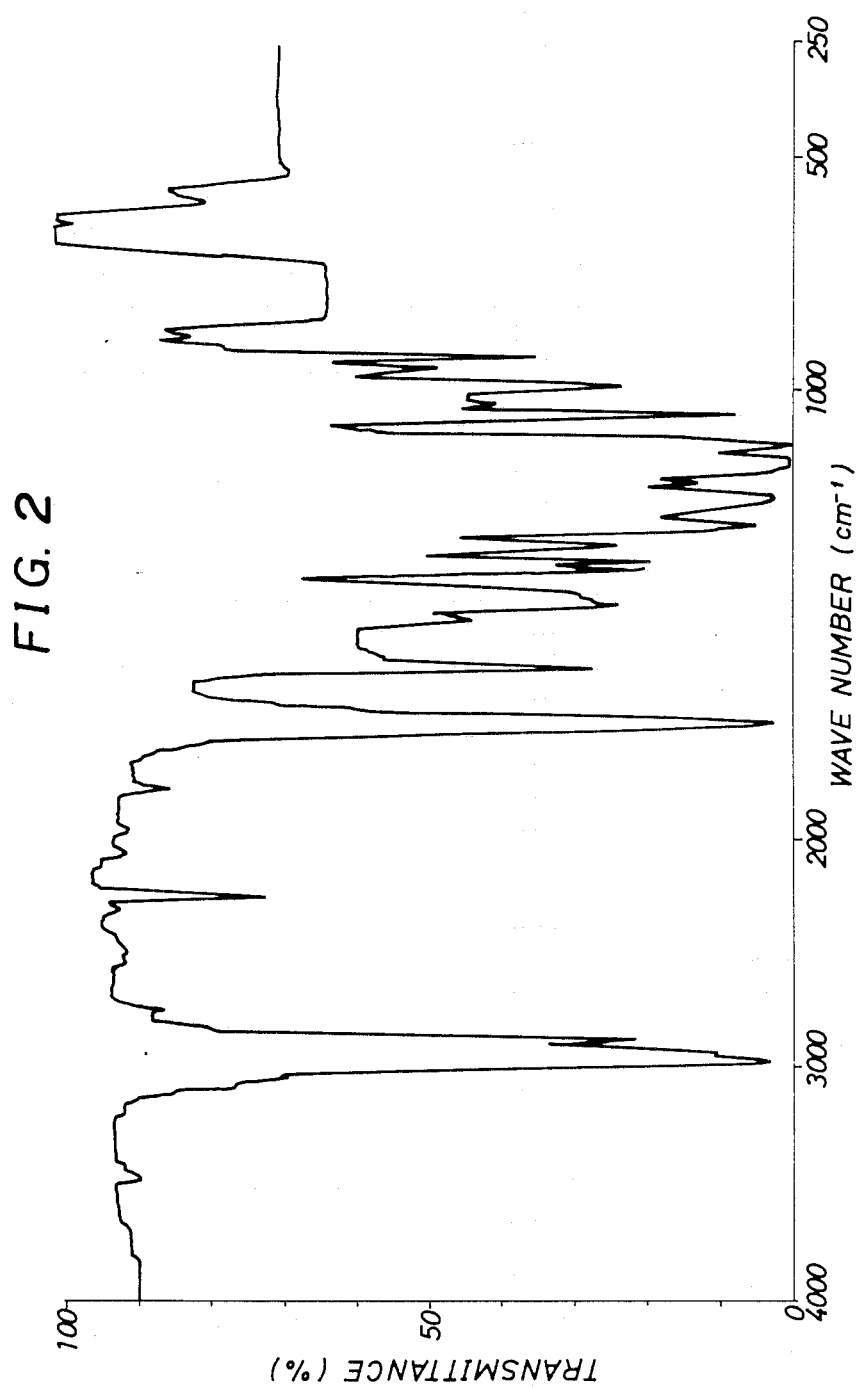
Figure 3:
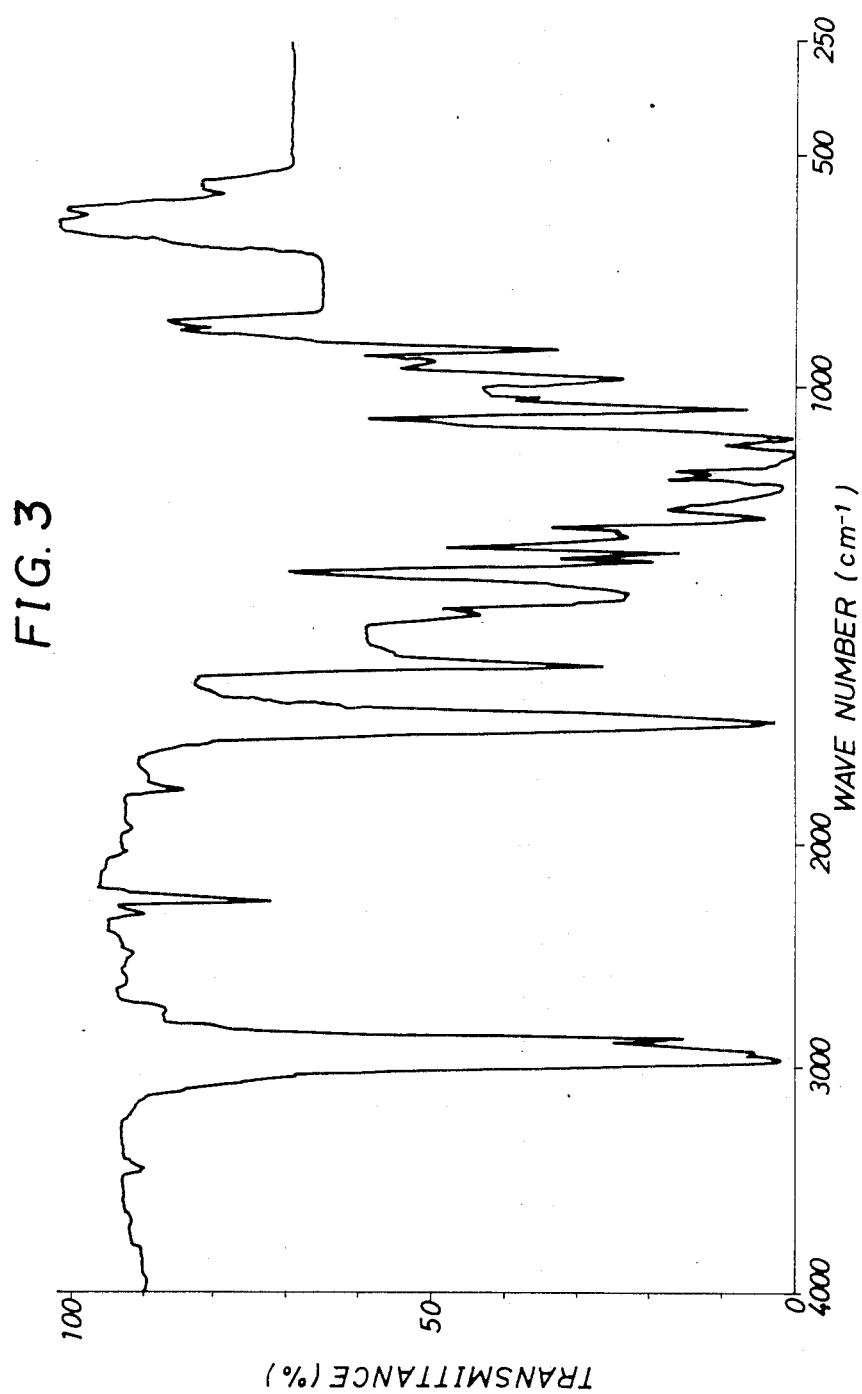
Figure 4:
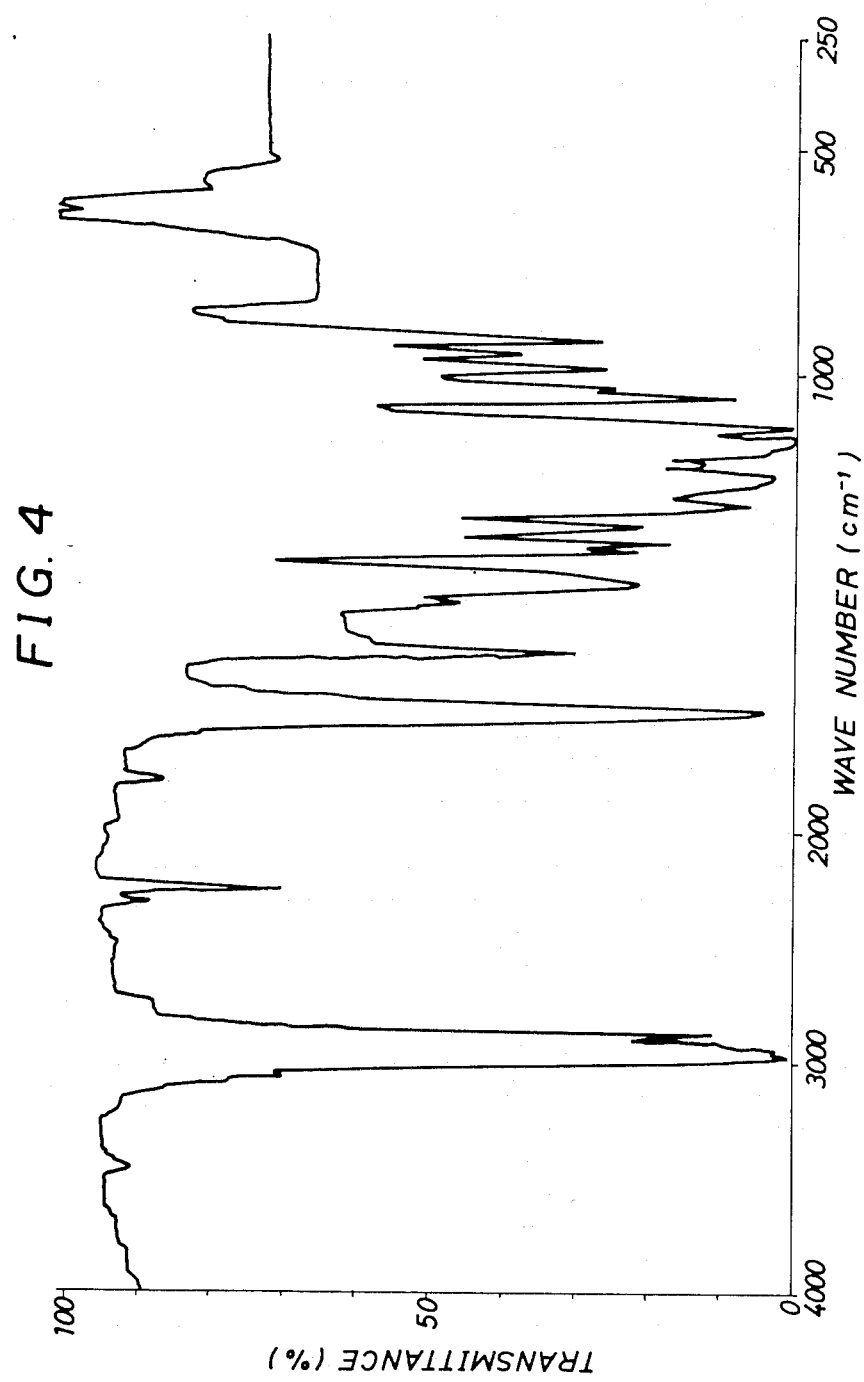
Figure 5:
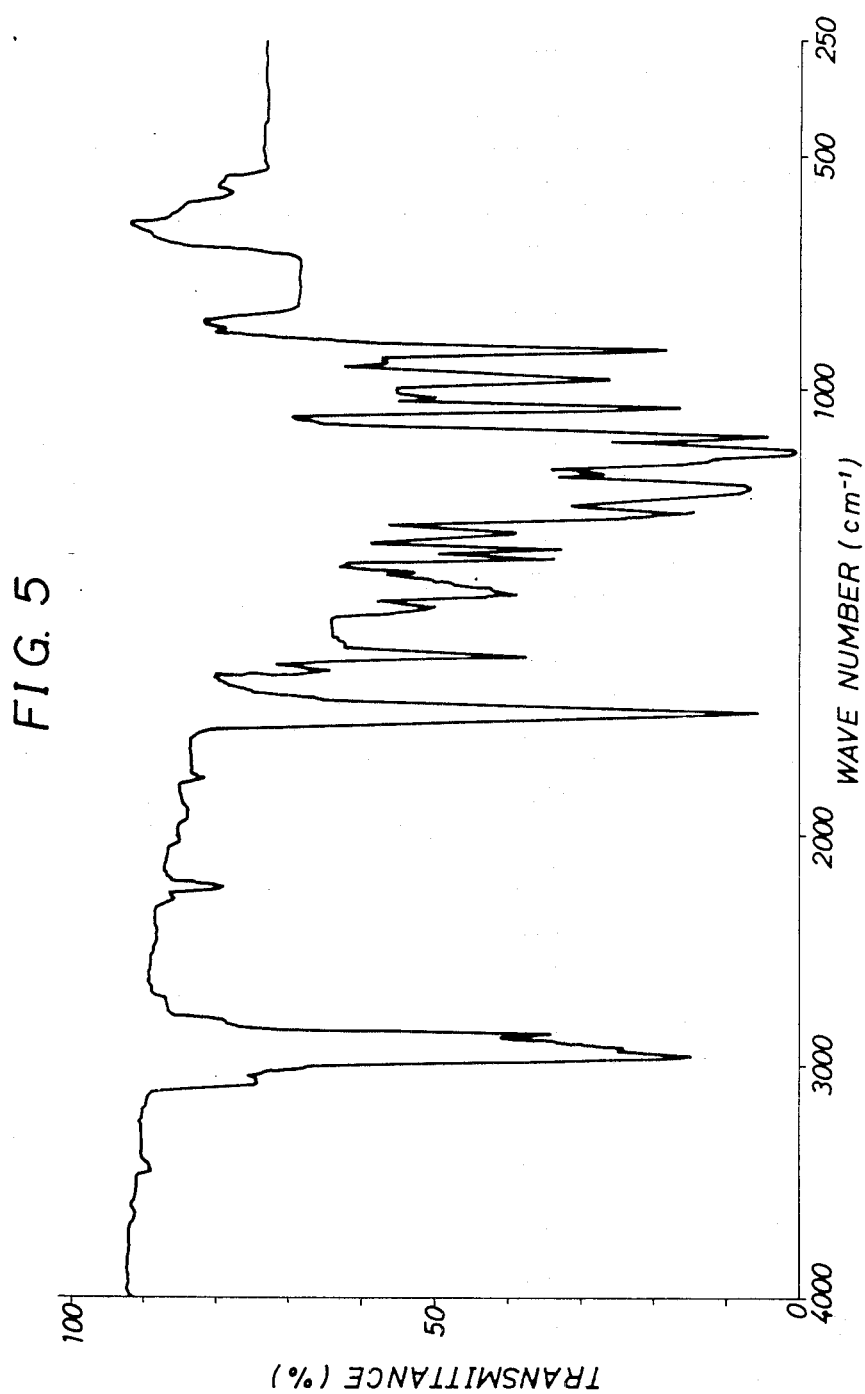
Figure 6:
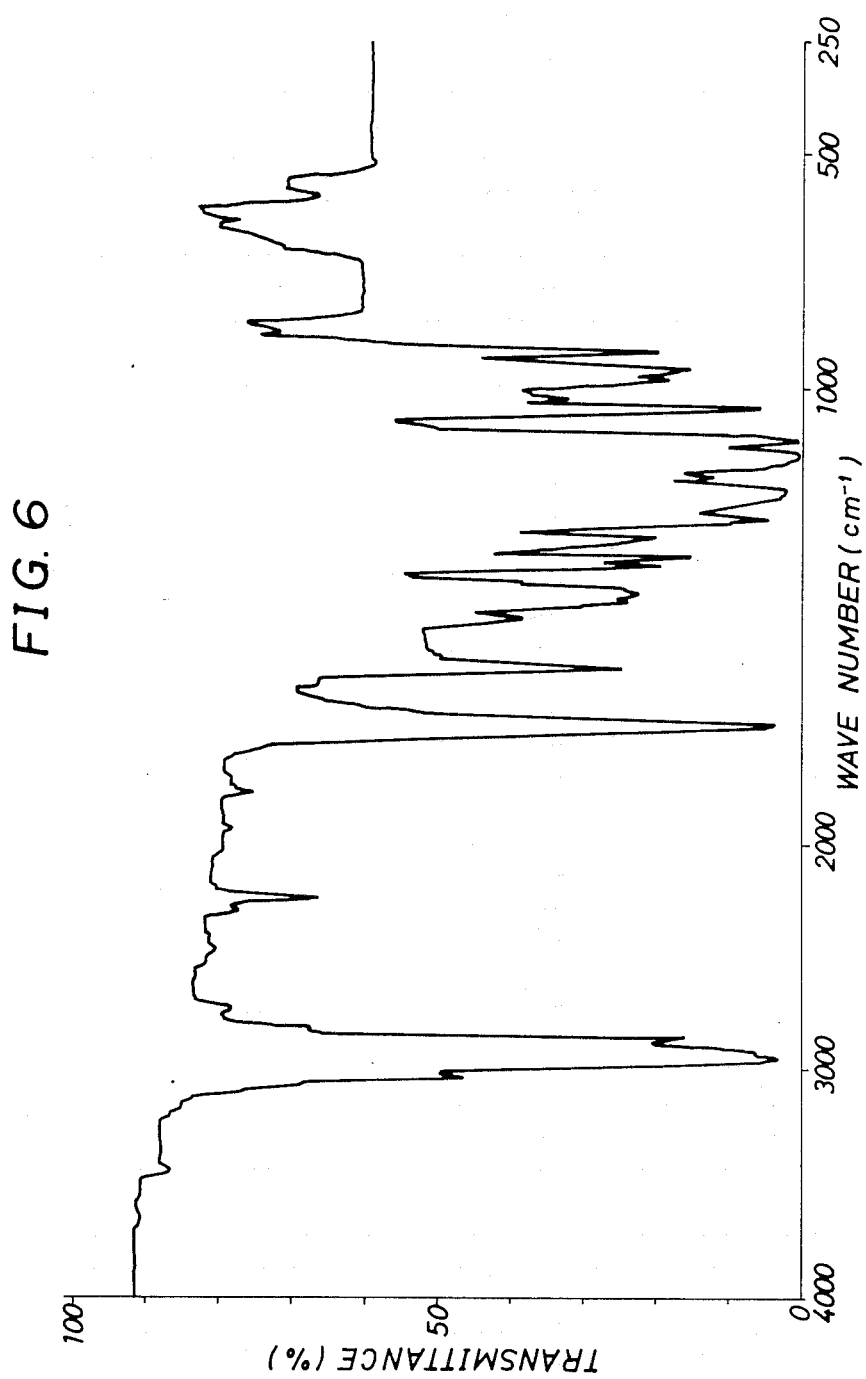
Figure 7:
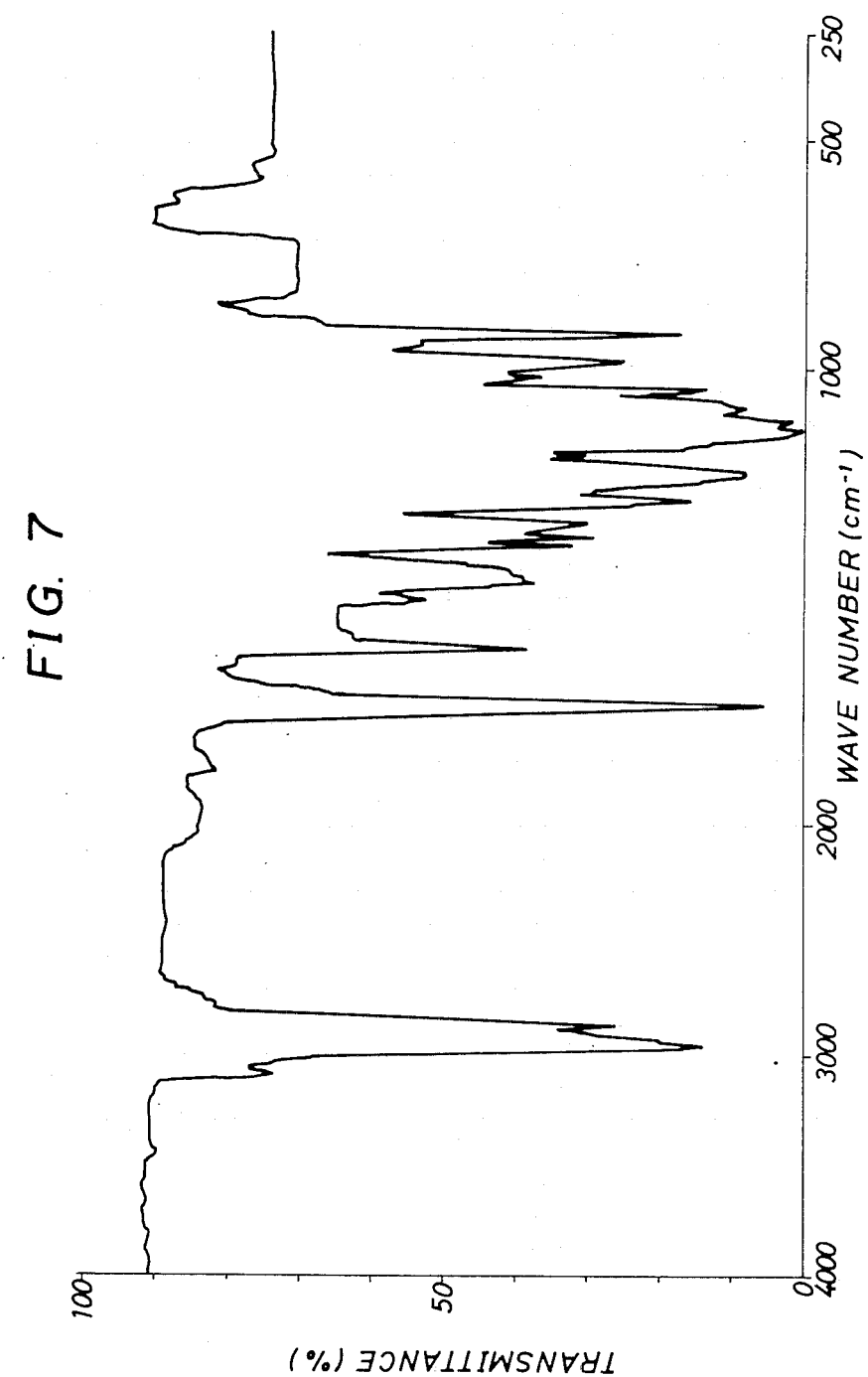
Figure 8:
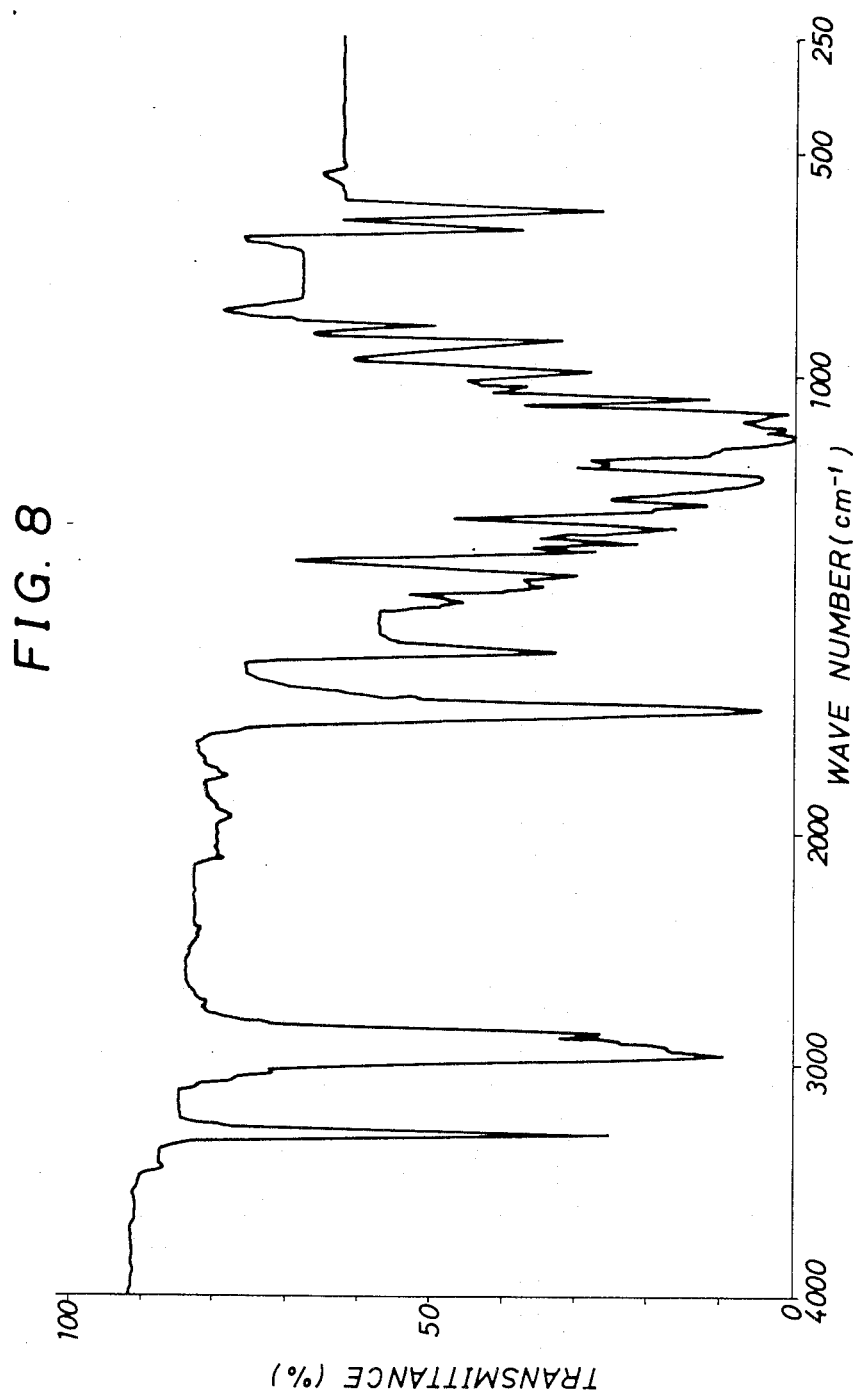
Figure 9:
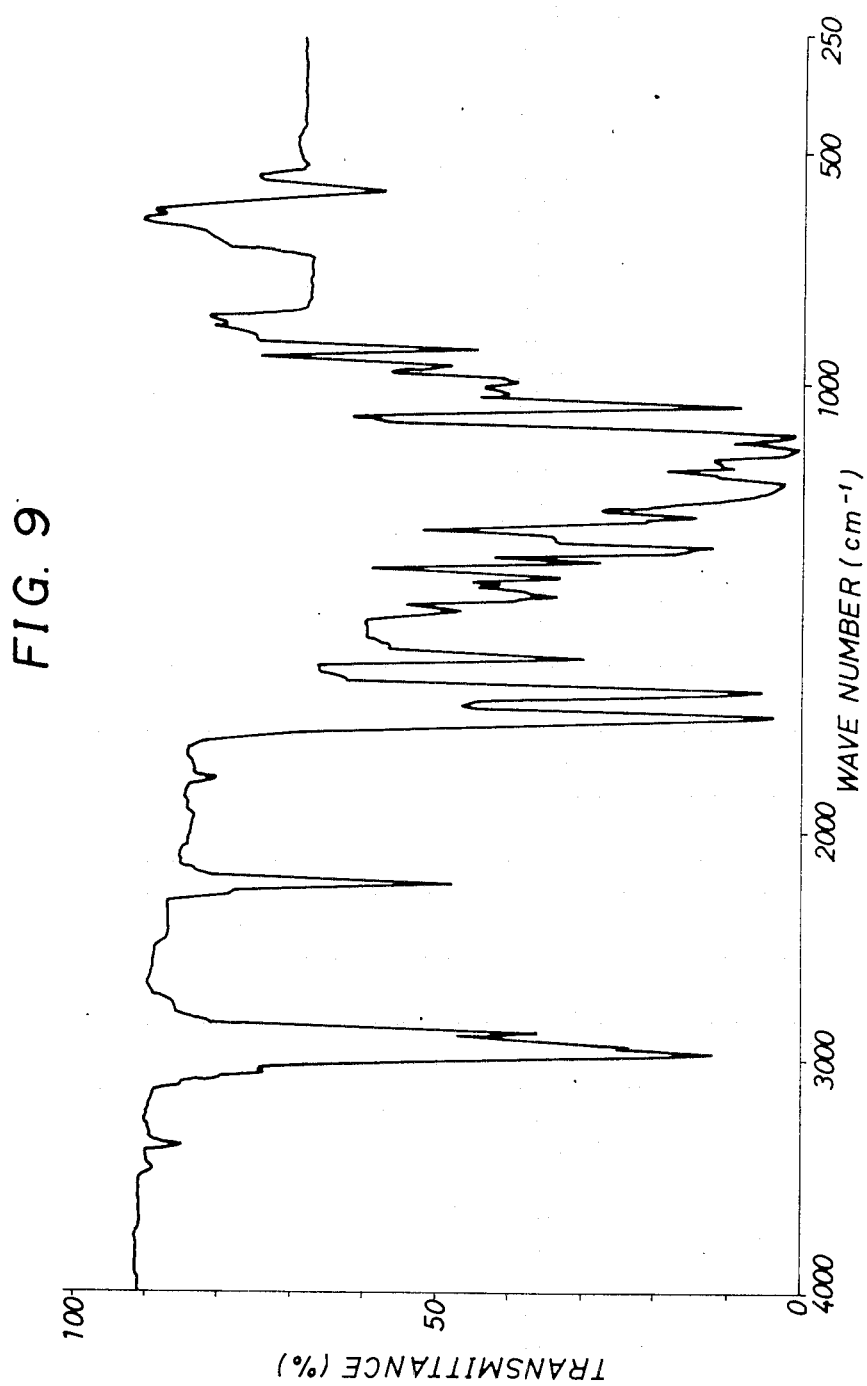
Figure 10:
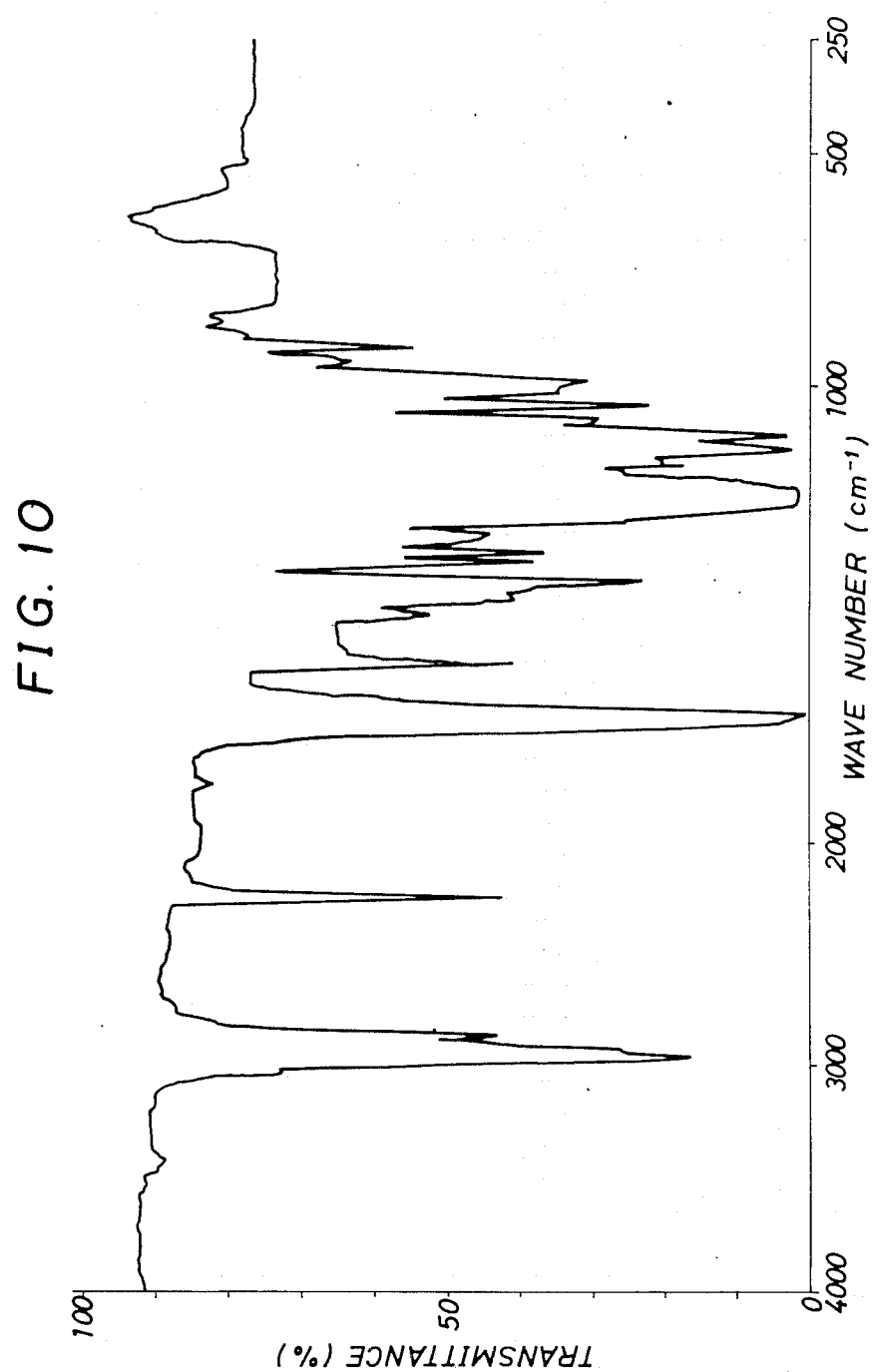
Figure 11:
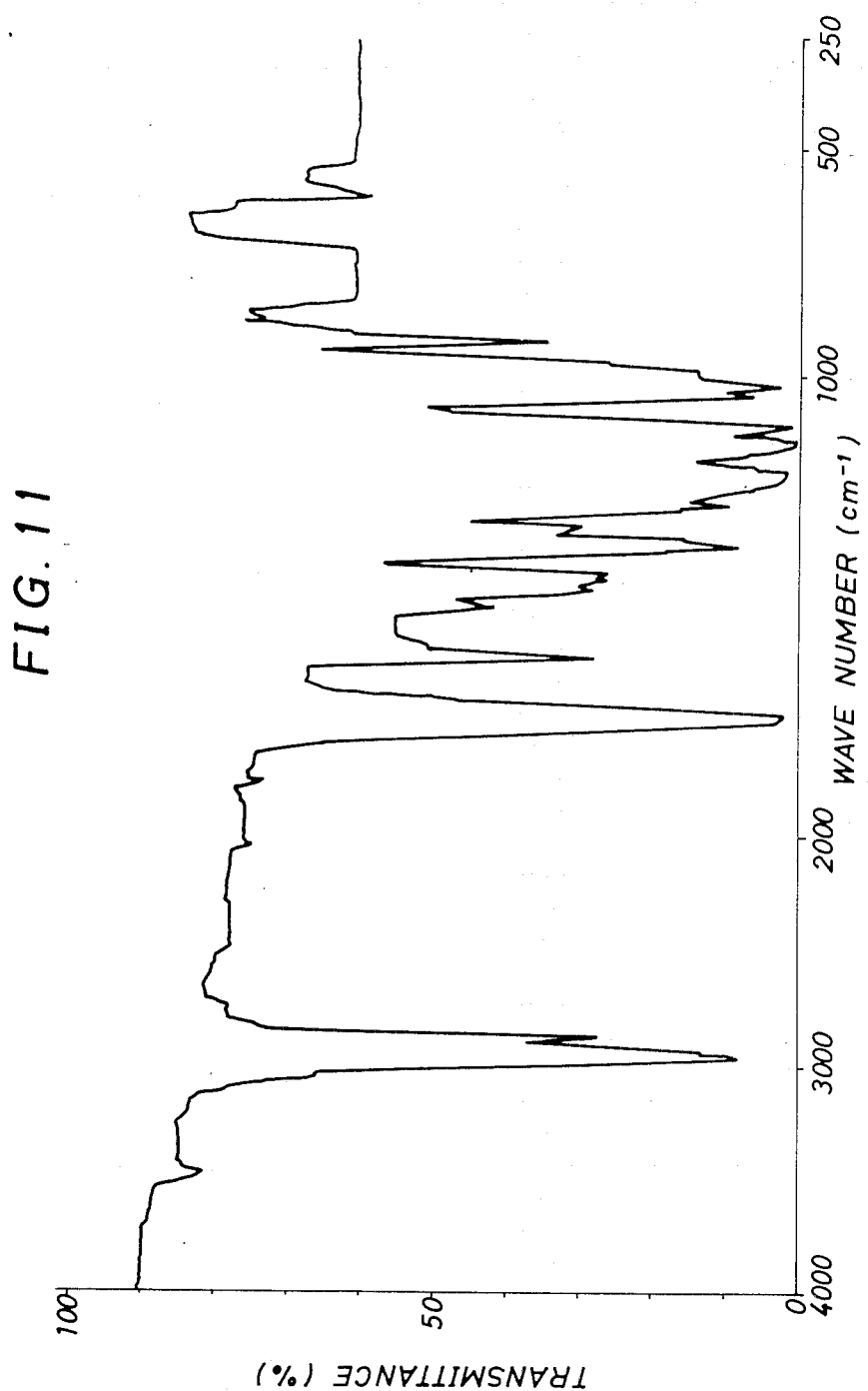
Figure 12:
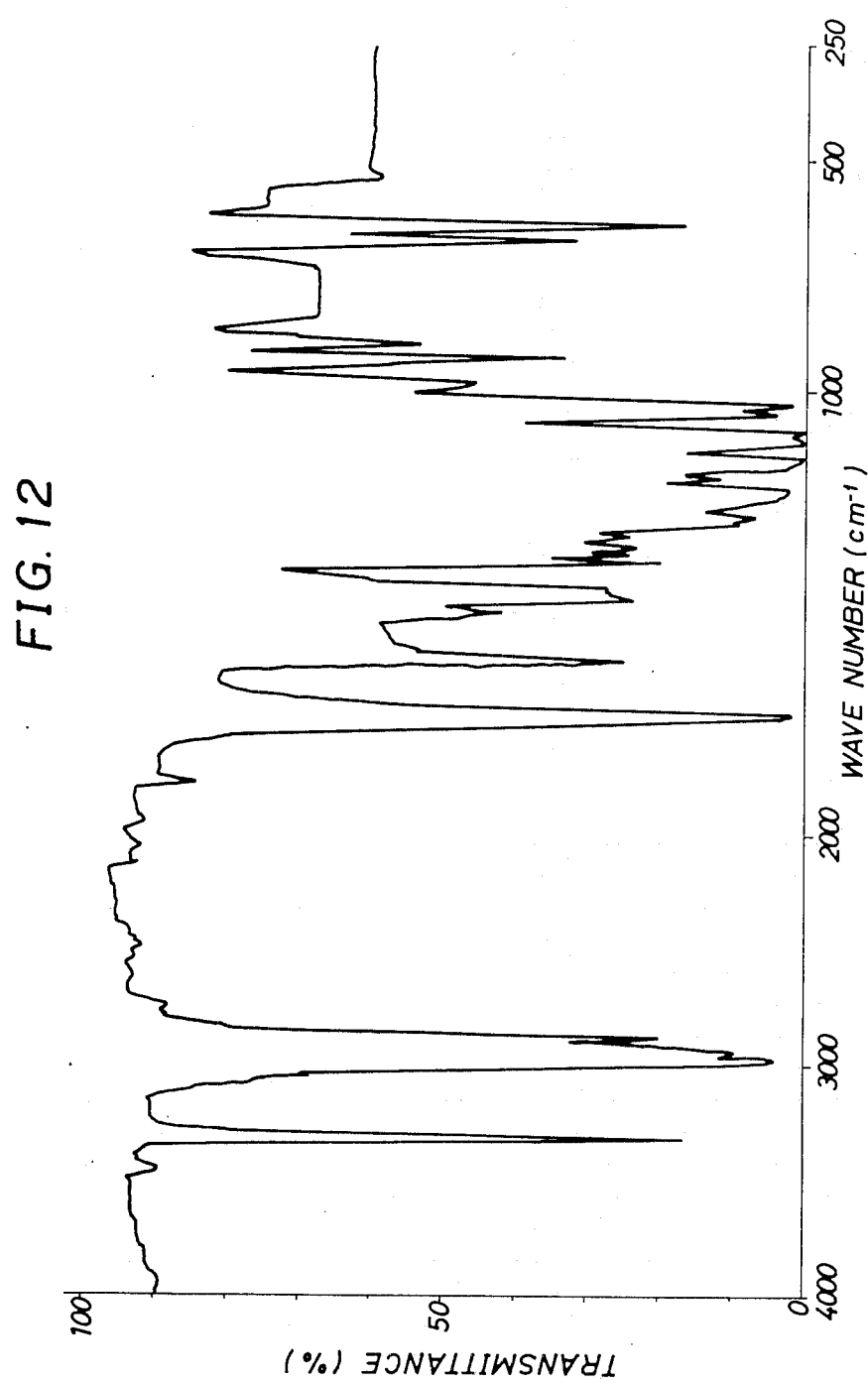
Figure 13:
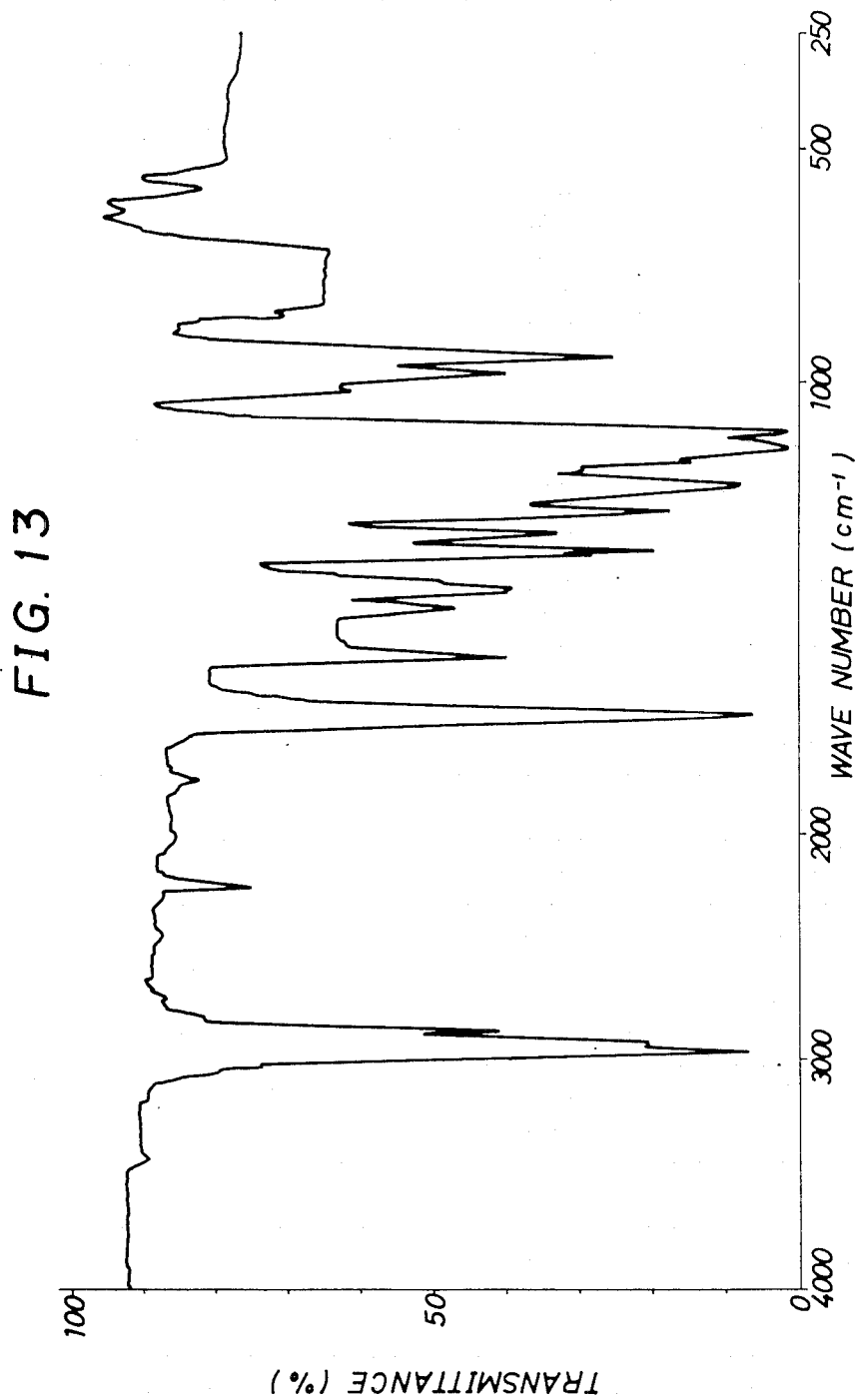
Figure 14:
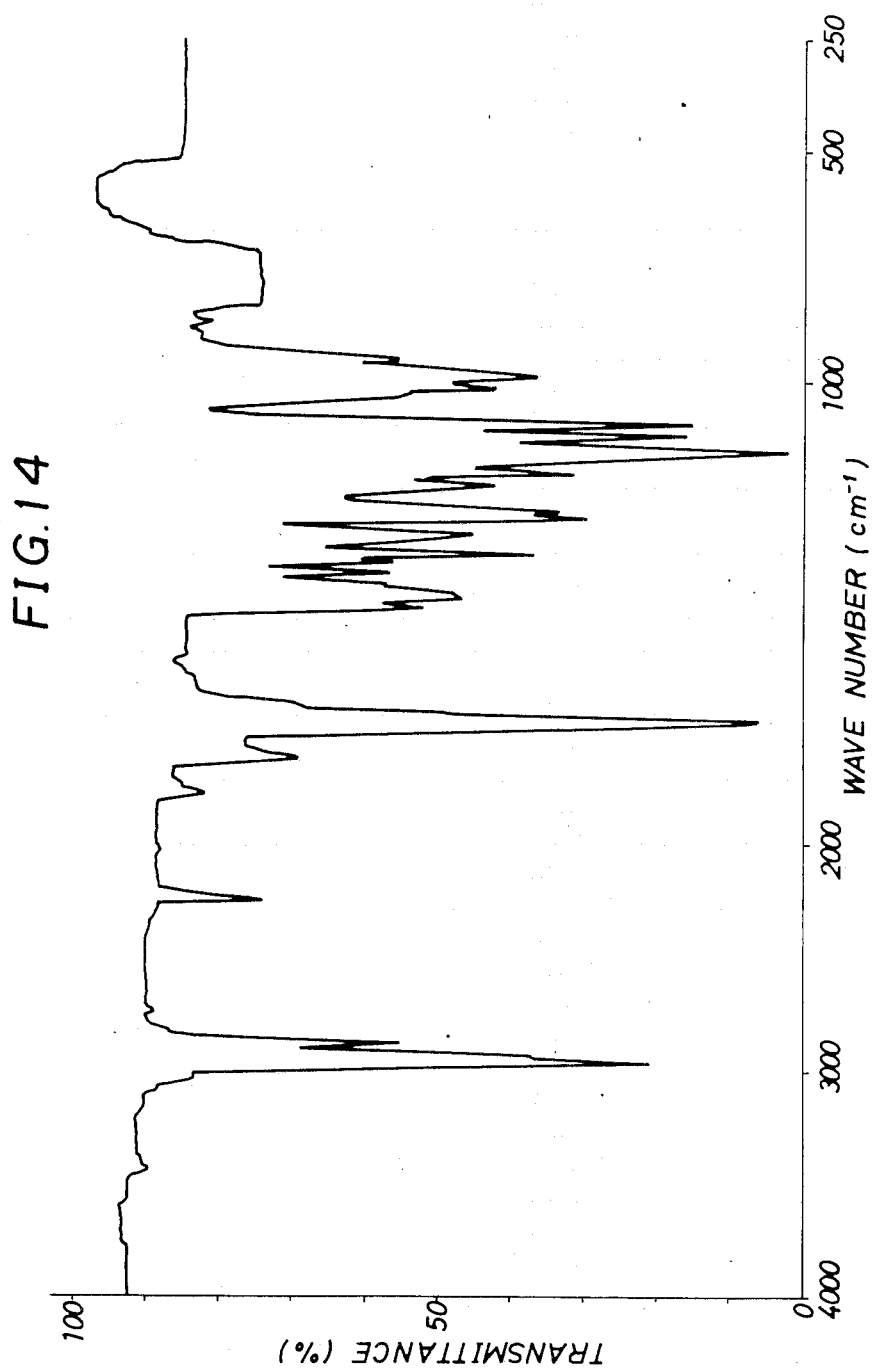
Figure 15:
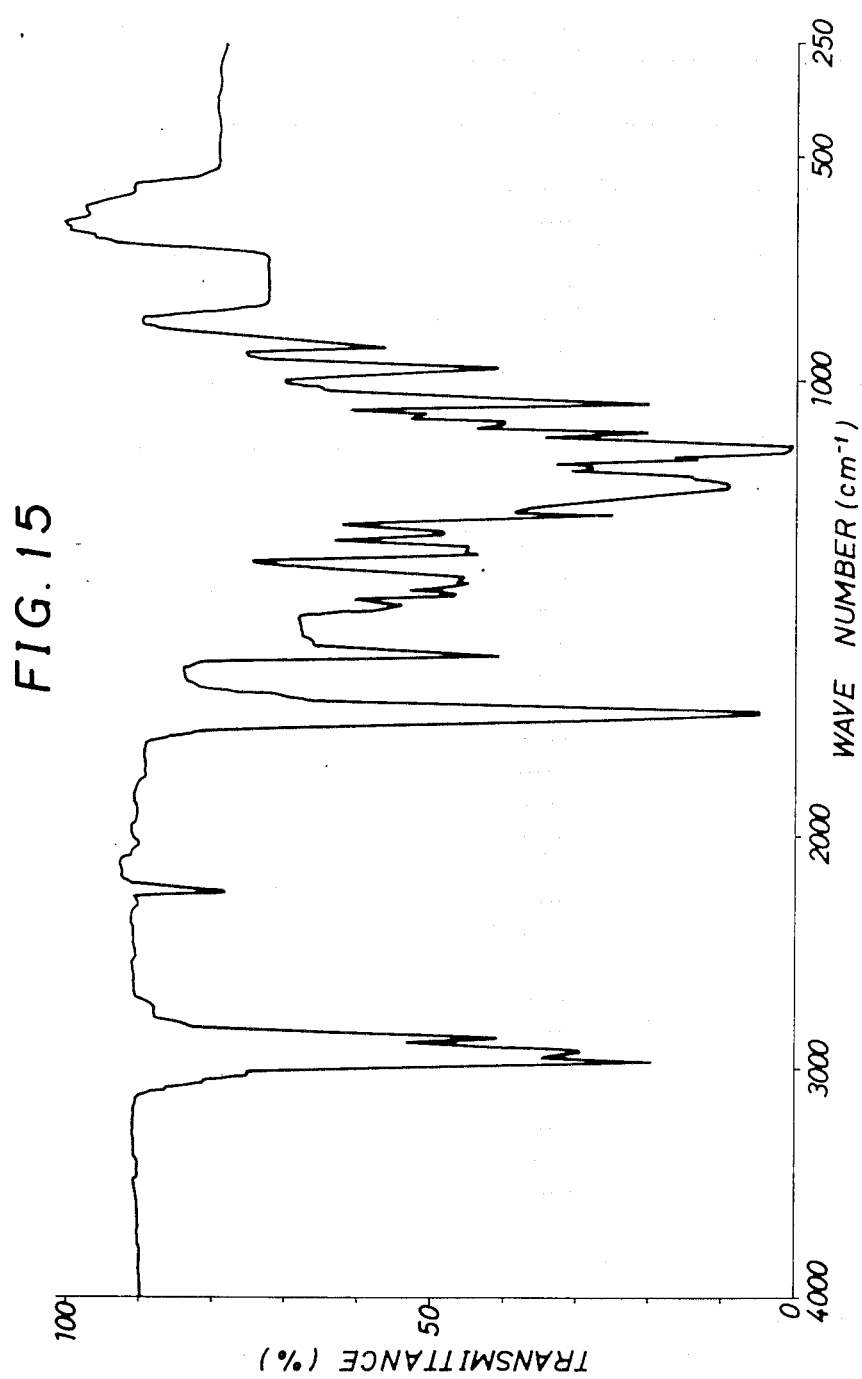
Figure 16:
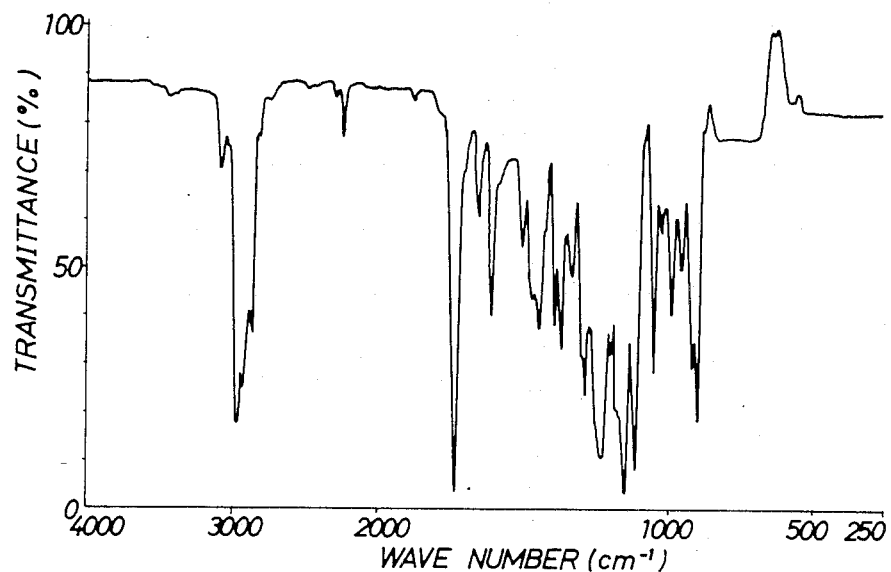
Figure 17:
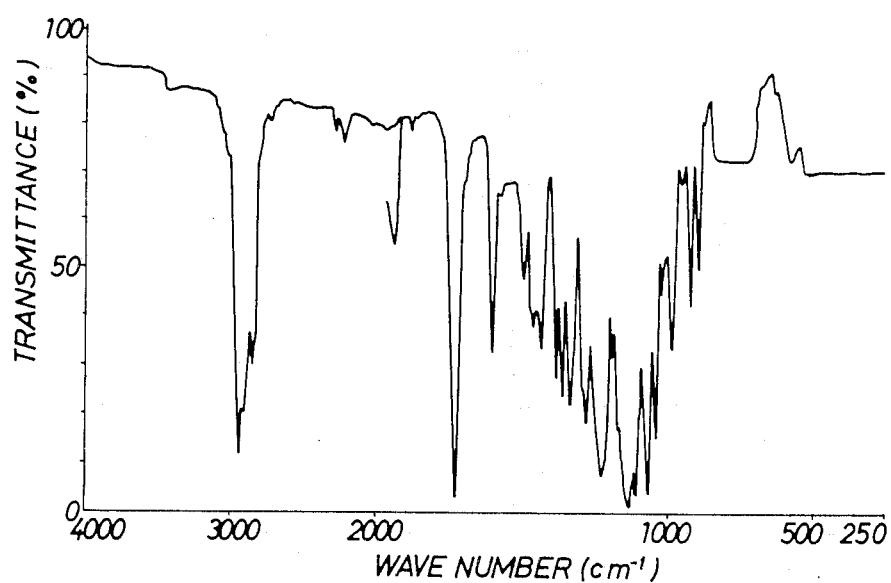
Figure 18:
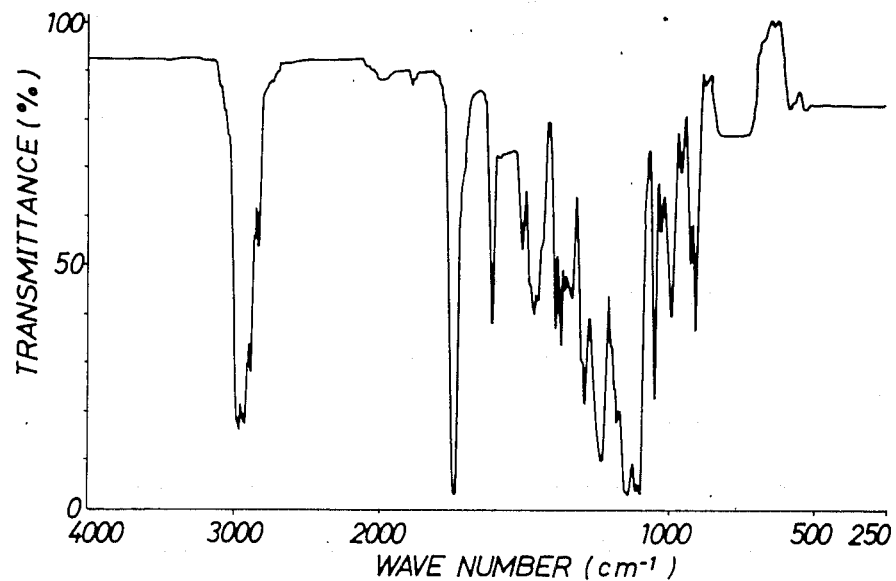
Figure 19:
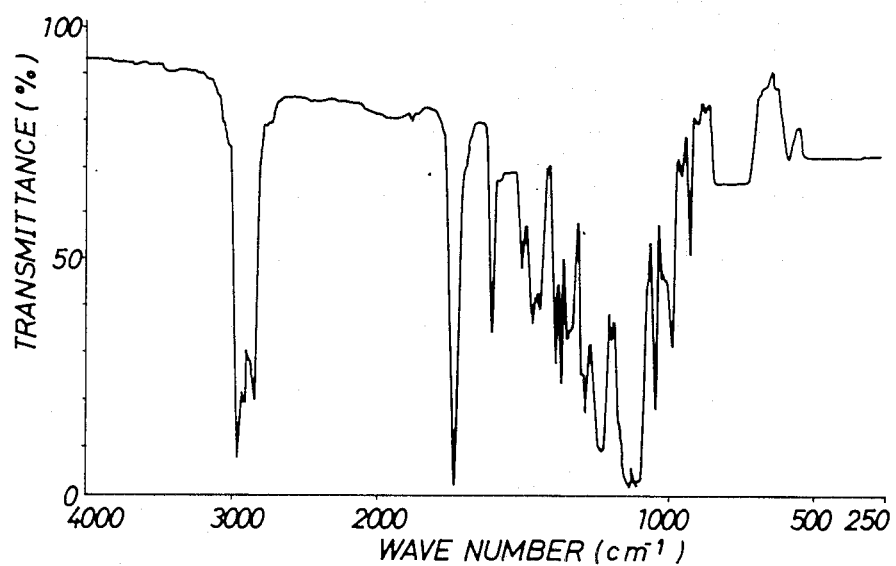
Figure 20:
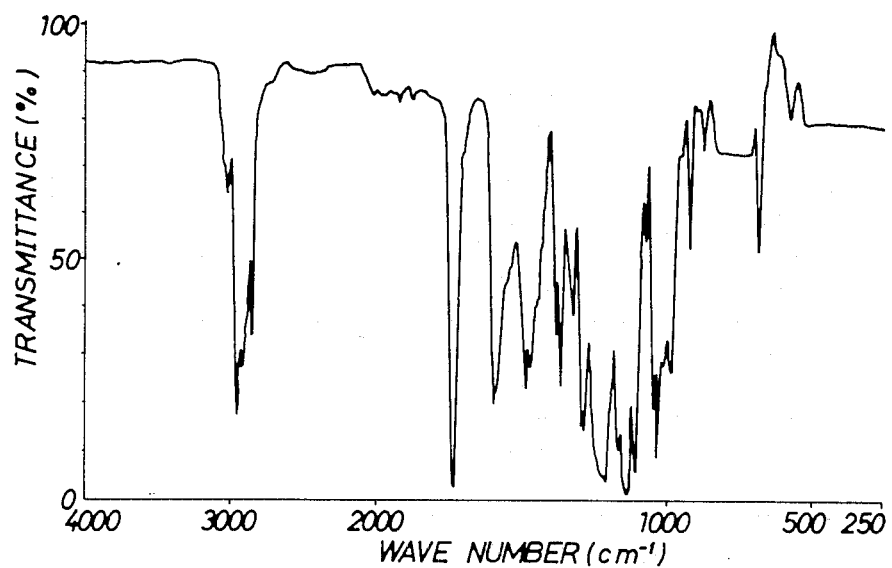
Figure 21:
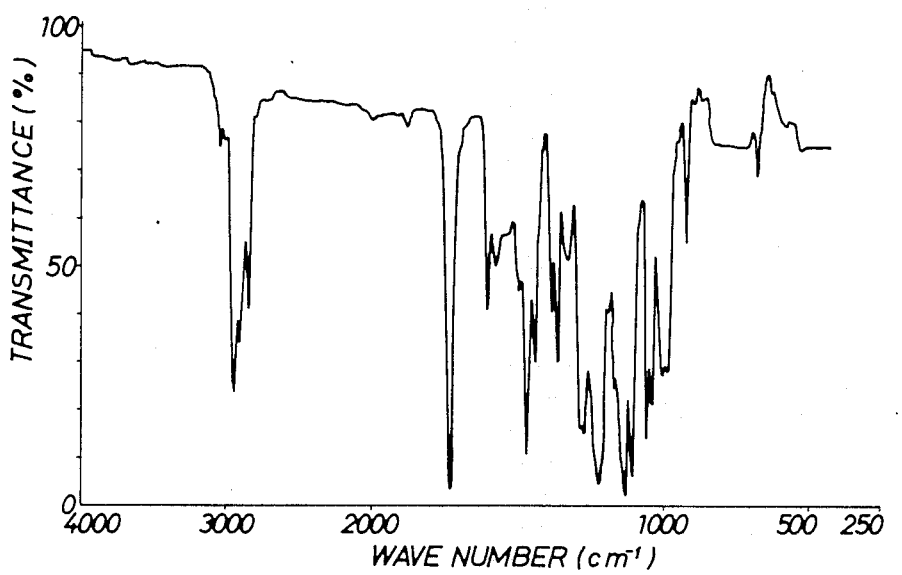
Figure 22:
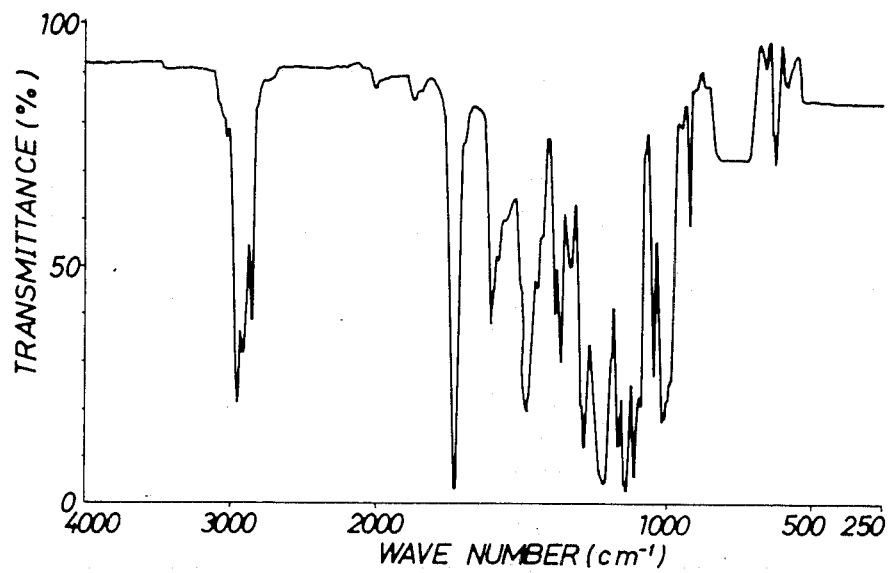
Figure 23:
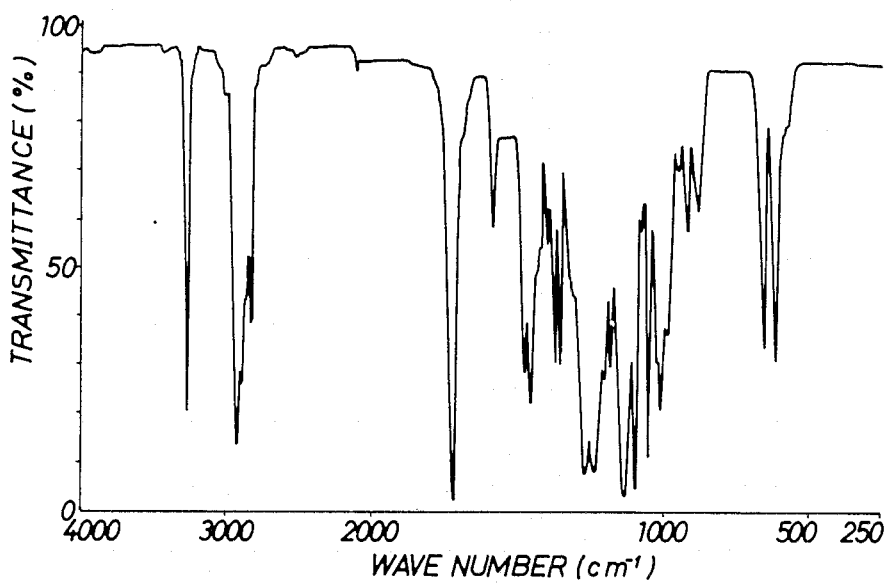

The compounds according to the present invention (hereinafter referred to as "the present compounds") represented by the general formula (I) are new compounds of substituted phenylacetic ester having one carbon-carbon triple bond in the alcohol moiety thereof and show insecticidal activity to noxious insects. The present compounds particularly show excellent and swift insecticidal activity to *Musca domestica*.

The present compounds may be easily synthesized, for instance, according to the following reaction formula:

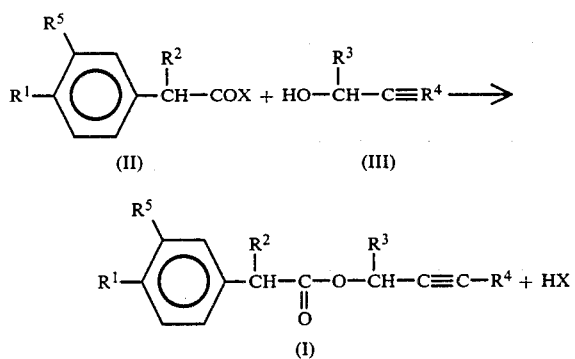

wheren $R^1$ represents a halogen atom or a lower alkoxy group, preferably ($C_1$-$C_3$) alkoxy group; $R^2$ represents a lower alkyl group, preferably ($C_1$-$C_3$) alkyl group; $R^3$ represents a hydrogen atom or a methyl group; $R^4$ represents a hydrogen atom, a lower alkyl group, preferably ($C_1$-$C_3$) alkyl group,

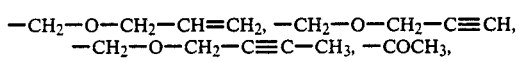

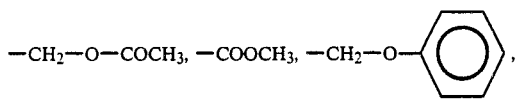

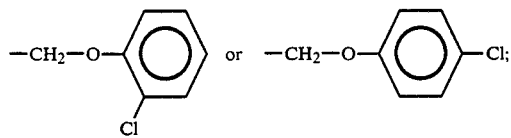

$R^5$ represents a hydrogen atom or a halogen atom and X represents a halogen atom such as chlorine and bromine.

Namely, the present compounds may be produced by reacting a carboxylic acid halide represented by the formula (II) with an alcohol represented by the formula (III) in a solvent in the presence of a condensing agent. As the solvent, benzene, toluene, ethyl ether, dioxane, chloroform, methylene chloride and carbon tetrachloride may be used, and more preferably used are benzene and toluene. As the condensing agent, pyridine, triethylamine, sodium hydroxide, potassium hydroxide, sodium carbonate and potassium carbonate may be used, and more preferably used are pyridine and triethylamine.

The carboxylic acid halide and the alcohol are condensed at a temperature of 0° to 100° C., preferably 10° to 40° C. for 1 to 24 hours, preferably for 1 to 4 hours.

Further, in the case of chlorinating the derivatives of phenylacetic ester represented by the formula (V), such a reaction formula is set forth below.

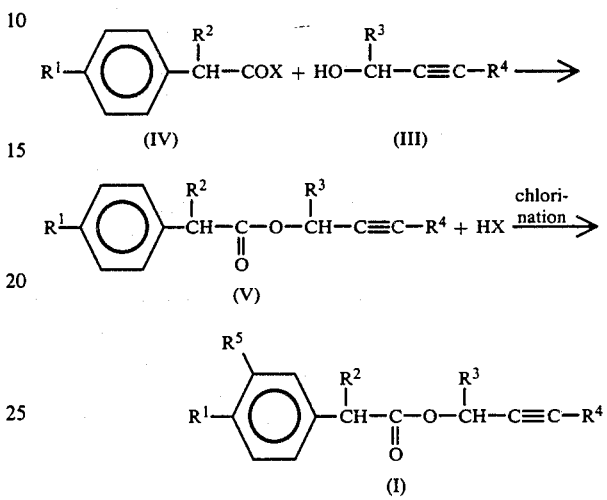

wherein $R^1$, $R^2$, $R^3$, $R^4$ and X are the same as defined above and $R^5$ represents a chlorine atom.

Namely, the present compounds may be produced by reacting a carboxylic acid halide represented by the formula (IV) with an alcohol represented by the formula (III) in a solvent in the presence of a condensing agent. As the solvent, benzene, toluene, ethyl ether, dioxane, chloroform, methylene chloride and carbon tetrachloride may be used, and more preferably used are benzene and toluene. As the condensing agent, pyridine, triethylamine, sodium hydroxide, potassium hydroxide, sodium carbonate and potassium carbonate may be used, and more preferably used are pyridine and triethylamine.

The carboxylic acid halide (IV) and the alcohol (III) are condensed at a temperature of 0° to 100° C., preferably 10° to 40° C. for 1 to 24 hours, preferably for 1 to 4 hours.

Then, the thus obtained ester (V) is chlorinated with a chlorinating agent such as thionyl chloride in a solvent such as chloroform, carbon tetrachloride and dichloromethane at a temperature of 0° C. to the boiling point of the solvent used for 1 to 50 hours.

However, the process for producing the present compound is not limited to the above-mentioned synthetic process.

The concrete examples of the present compounds are shown in Table 1. It should be understood that the compounds shown in Table 1 have stereoisomers and each one of these stereoisomers is included in the present invention.

TABLE 1

| Compound No. | Name | Structural formula |
|---|---|---|
| 1. | 2-propynyl 2-(4-ethoxyphenyl)isovalerate | $CH_3CH_2O$—⟨phenyl⟩—$CH-C(=O)-O-CH_2-C\equiv CH$ with $CH(CH_3)_2$ substituent |

TABLE 1-continued

| Compound No. | Name | Structural formula |
|---|---|---|
| 2. | 2-butynyl 2-(4-ethoxyphenyl)isovalerate | $CH_3CH_2O-C_6H_4-CH(CH(CH_3)_2)-C(=O)-O-CH_2-C{\equiv}C-CH_3$ |
| 3. | 2-pentynyl 2-(4-ethoxyphenyl)isovalerate | $CH_3CH_2O-C_6H_4-CH(CH(CH_3)_2)-C(=O)-O-CH_2-C{\equiv}C-CH_2CH_3$ |
| 4. | 2-hexynyl 2-(4-ethoxyphenyl)isovalerate | $CH_3CH_2O-C_6H_4-CH(CH(CH_3)_2)-C(=O)-O-CH_2-C{\equiv}C-CH_2CH_2CH_3$ |
| 5. | 5-hexen-2-ynyl 2-(4-ethoxyphenyl)isovalerate | $CH_3CH_2O-C_6H_4-CH(CH(CH_3)_2)-C(=O)-O-CH_2-C{\equiv}C-CH_2-CH{=}CH_2$ |
| 6. | trans-5-hepten-2-ynyl 2-(4-ethoxyphenyl)isovalerate | $CH_3CH_2O-C_6H_4-CH(CH(CH_3)_2)-C(=O)-O-CH_2-C{\equiv}C-CH_2-CH{=}CH-CH_3$ |
| 7. | 4-(2-propenyloxy)-2-butynyl 2-(4-ethoxyphenyl)isovalerate | $CH_3CH_2O-C_6H_4-CH(CH(CH_3)_2)-C(=O)-O-CH_2-C{\equiv}C-CH_2OCH_2CH{=}CH_2$ |
| 8. | 4-(2-propynyloxy)-2-butynyl 2-(4-ethoxyphenyl)isovalerate | $CH_3CH_2O-C_6H_4-CH(CH(CH_3)_2)-C(=O)-O-CH_2-C{\equiv}C-CH_2OCH_2-C{\equiv}CH$ |
| 9. | 2-pentyn-4-on-1-yl 2-(4-ethoxyphenyl)isovalerate | $CH_3CH_2O-C_6H_4-CH(CH(CH_3)_2)-C(=O)-O-CH_2-C{\equiv}C-C(=O)-CH_3$ |
| 10. | 3-methoxycarbonyl-2-propynyl 2-(4-ethoxyphenyl)isovalerate | $CH_3CH_2O-C_6H_4-CH(CH(CH_3)_2)-C(=O)-O-CH_2-C{\equiv}C-C(=O)-O-CH_3$ |
| 11. | 4-acetoxy-2-butynyl 2-(4-ethoxyphenyl)isovalerate | $CH_3CH_2O-C_6H_4-CH(CH(CH_3)_2)-C(=O)-O-CH_2-C{\equiv}C-CH_2-O-C(=O)-CH_3$ |
| 12. | 1-methyl-2-propynyl 2-(4-ethoxyphenyl)isovalerate | $CH_3CH_2O-C_6H_4-CH(CH(CH_3)_2)-C(=O)-O-CH(CH_3)-C{\equiv}CH$ |
| 13. | 2-butynyl 2-(4-isopropoxyphenyl)isovalerate | $(CH_3)_2CHO-C_6H_4-CH(CH(CH_3)_2)-C(=O)-O-CH_2-C{\equiv}C-CH_3$ |
| 14. | 2-butynyl 2-(4-chlorophenyl)isovalerate | $Cl-C_6H_4-CH(CH(CH_3)_2)-C(=O)-O-CH_2-C{\equiv}C-CH_3$ |

TABLE 1-continued

| Compound No. | Name | Structural formula |
|---|---|---|
| 15. | 2-butynyl 2-(4-ethoxyphenyl)-n-butyrate | CH₃CH₂O—⟨C₆H₄⟩—CH(CH₂—CH₃)—C(=O)—O—CH₂—C≡C—CH₃ |
| 16 | 5-methyl-5-hexen-2-ynyl 2-(4-ethoxyphenyl)isovalerate | CH₃CH₂O—⟨C₆H₄⟩—CH(CH(CH₃)₂)—C(=O)—O—CH₂—C≡C—CH₂—C(CH₃)=CH₂ |
| 17 | 4-(2-butynyloxy)-2-butynyl 2-(4-ethoxyphenyl)isovalerate | CH₃CH₂O—⟨C₆H₄⟩—CH(CH(CH₃)₂)—C(=O)—O—CH₂—C≡C—CH₂OCH₂—C≡C—CH₃ |
| 18 | 4-methoxy-2-butynyl 2-(4-ethoxyphenyl)isovalerate | CH₃CH₂O—⟨C₆H₄⟩—CH(CH(CH₃)₂)—C(=O)—O—CH₂—C≡C—CH₂OCH₃ |
| 19 | 4-ethoxy-2-butynyl 2-(4-ethoxyphenyl)isovalerate | CH₃CH₂O—⟨C₆H₄⟩—CH(CH(CH₃)₂)—C(=O)—O—CH₂—C≡C—CH₂OCH₂CH₃ |
| 20 | 4-phenoxy-2-butynyl 2-(4-ethoxyphenyl)isovalerate | CH₃CH₂O—⟨C₆H₄⟩—CH(CH(CH₃)₂)—C(=O)—O—CH₂—C≡C—CH₂—O—⟨C₆H₅⟩ |
| 21 | 4-(2-chlorophenoxy)-2-butynyl 2-(4-ethoxyphenyl)isovalerate | CH₃CH₂O—⟨C₆H₄⟩—CH(CH(CH₃)₂)—C(=O)—O—CH₂—C≡C—CH₂—O—⟨C₆H₄-2-Cl⟩ |
| 22 | 4-(4-chlorophenoxy)-2-butynyl 2-(4-ethoxyphenyl)isovalerate | CH₃CH₂O—⟨C₆H₄⟩—CH(CH(CH₃)₂)—C(=O)—O—CH₂—C≡C—CH₂—O—⟨C₆H₄-4-Cl⟩ |
| 23 | 2-propynyl 2-(3-chloro-4-ethoxyphenyl)isovalerate | CH₃CH₂O—⟨C₆H₃-3-Cl⟩—CH(CH(CH₃)₂)—C(=O)—O—CH₂—C≡CH |
| 24 | 2-butynyl 2-(3-chloro-4-ethoxyphenyl)isovalerate | CH₃CH₂O—⟨C₆H₃-3-Cl⟩—CH(CH(CH₃)₂)—C(=O)—O—CH₂—C≡C—CH₃ |
| 25 | 5-hexen-2-ynyl 2-(3-chloro-4-ethoxyphenyl)isovalerate | CH₃CH₂O—⟨C₆H₃-3-Cl⟩—CH(CH(CH₃)₂)—C(=O)—O—CH₂—C≡C—CH₂—CH=CH₂ |
| 26 | 4-(2-propynyloxy)-2-butynyl 2-(3-chloro-4-ethoxyphenyl)-isovalerate | CH₃CH₂O—⟨C₆H₃-3-Cl⟩—CH(CH(CH₃)₂)—C(=O)—O—CH₂—C≡C—CH₂—O—CH₂—C≡CH |

TABLE 1-continued

| Compound No. | Name | Structural formula |
|---|---|---|
| 27 | 2-butynyl 2-(3-chloro-4-methoxyphenyl)isovalerate | 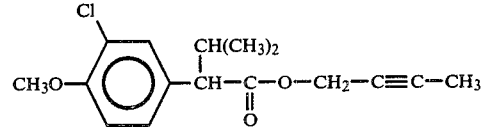 |
| 28 | 4-(2-propynyloxy)-2-butynyl 2-(3-chloro-4-methoxyphenyl)-isovalerate | 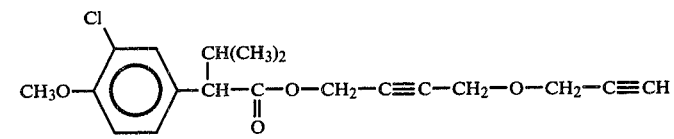 |
| 29 | 2-butynyl 2-(3-chloro-4-isopropoxyphenyl)isovalerate | 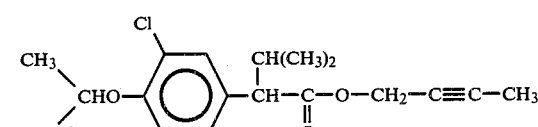 |
| 30 | 4-(2-propynyloxy)-2-butynyl 2-(3-chloro-4-isopropoxy-phenyl)isovalerate | 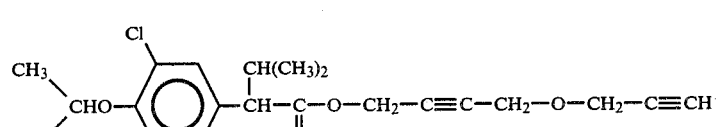 |
| 31 | 2-butynyl 2-(3-bromo-4-ethoxyphenyl)isovalerate | 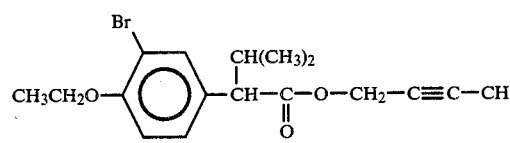 |
| 32 | 4-(2-propynyloxy)-2-butynyl 2-(3-bromo-4-ethoxyphenyl)-isovalerate | 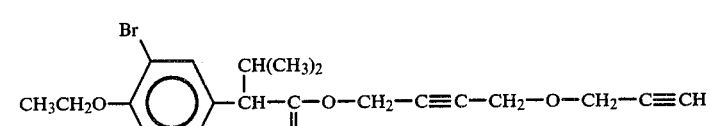 |
| 33 | 2-propynyl 2-(3-fluoro-4-ethoxyphenyl)isovalerate | 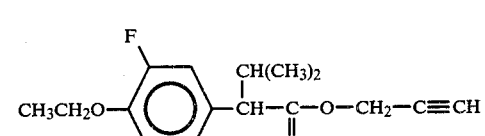 |
| 34 | 2-butynyl 2-(3-fluoro-4-ethoxyphenyl)isovalerate | 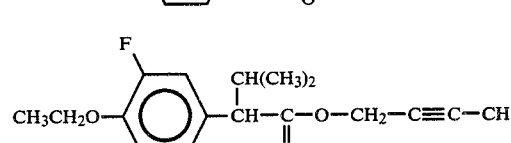 |
| 35 | 2-pentynyl 2-(3-fluoro-4-ethoxyphenyl)isovalerate | 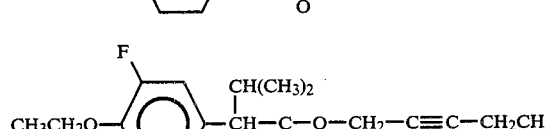 |
| 36 | 4-(2-propynyloxy)-2-butynyl 2-(3-fluoro-4-ethoxyphenyl)-isovalerate | 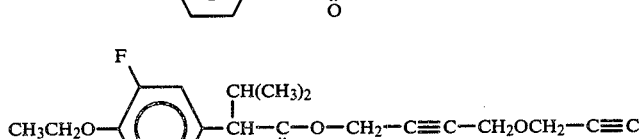 |
| 37 | 2-butynyl 2-(3-fluoro-4-methoxyphenyl)isovalerate | 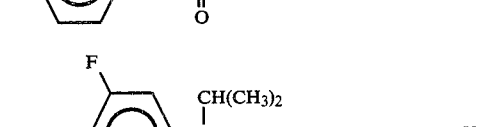 |

TABLE 1-continued

| Compound No. | Name | Structural formula |
|---|---|---|
| 38 | 2-propynyl 2-(3-fluoro-4-isopropoxyphenyl)isovalerate | |
| 39 | 2-butynyl 2-(3-fluoro-4-isopropoxyphenyl)isovalerate | |
| 40 | 4-(2-propynyloxy)-2-butynyl 2-(3-fluoro-4-isopropoxyphenyl)isovalerate | |
| 41 | 2-butynyl 2-(3,4-dichlorophenyl)isovalerate | |

Generally, the swift effect of an insecticidal compound closely depends on the volatility thereof, and the volatility of the present compounds is equal to or higher than allethrin as will be seen in Table 2 wherein the retention time of the present compounds in gas-chromatography and that of allethrin is given.

TABLE 2

Retention Time in Gas-chromatography

| Compound | Retention time (min) |
|---|---|
| Present compound | |
| No. 1 | 6.57 |
| No. 2 | 14.98 |
| No. 3 | 20.18 |
| No. 4 | 29.77 |
| No. 5 | 32.09 |
| No. 12 | 6.87 |
| No. 13 | 14.71 |
| No. 14 | 7.87 |
| Allethrin | 28.80 |

Note:
Conditions in Gas-chromatography:
Column material: Dexsil packed in the length of 1 m
Column temperature: 190° C.
Carrier gas: helium at a flow rate of 40 ml/min The present invention will be explained more in detail in the non-limitative Examples which follow.

EXAMPLE

Synthesis of 2-propynyl 2-(4-ethoxyphenyl)isovalerate (Compound No. 1)

Into a solution of 0.10 g of (0.45 mM) of 2-(4-ethoxyphenyl)isovalerianic acid in 2 ml of anhydrous methylene chloride, 0.11 g (0.90 mM) of thionyl chloride and a catalytic amount of dimethylformamide were added, and the mixture was stirred for 2 hours in an oil bath at 40° C. Thereafter, an excess of thionyl chloride and methylene chloride were distilled off from the reaction mixture under a reduced pressure, whereby 2-(4-ethoxyphenyl)isovaleric chloride was obtained as an oily substance. After dissolving the thus obtained oily substance in 1 ml of anhydrous benzene, a solution of 0.025 g (0.45 mM) of 2-propyn-1-ol in 1 ml of anhydrous benzene and 0.043 g of pyridine were added to the thus prepared solution, and the thus prepared mixture was stirred for 2 hours at room temperature, thereby completing the reaction.

Then, the reaction mixture was poured into iced water, and the mixture was extracted with benzene. After washing the extract with 5% hydrochloric acid, a saturated solution of sodium hydrogen carbonate and a saturated solution of sodium chloride, successively and drying the thus washed extract over anhydrous sodium sulfate, benzene was distilled off from the dried extract to obtain an oily substance. The oily substance was subjected to silica gel column chromatography while using a 1:20 mixture of ethyl acetate and n-hexane as an eluent for the purpose of purification of the oily substance to obtain 0.084 g of the colourless and oily compound No. 1 (yield: 71%).

Figure 42:
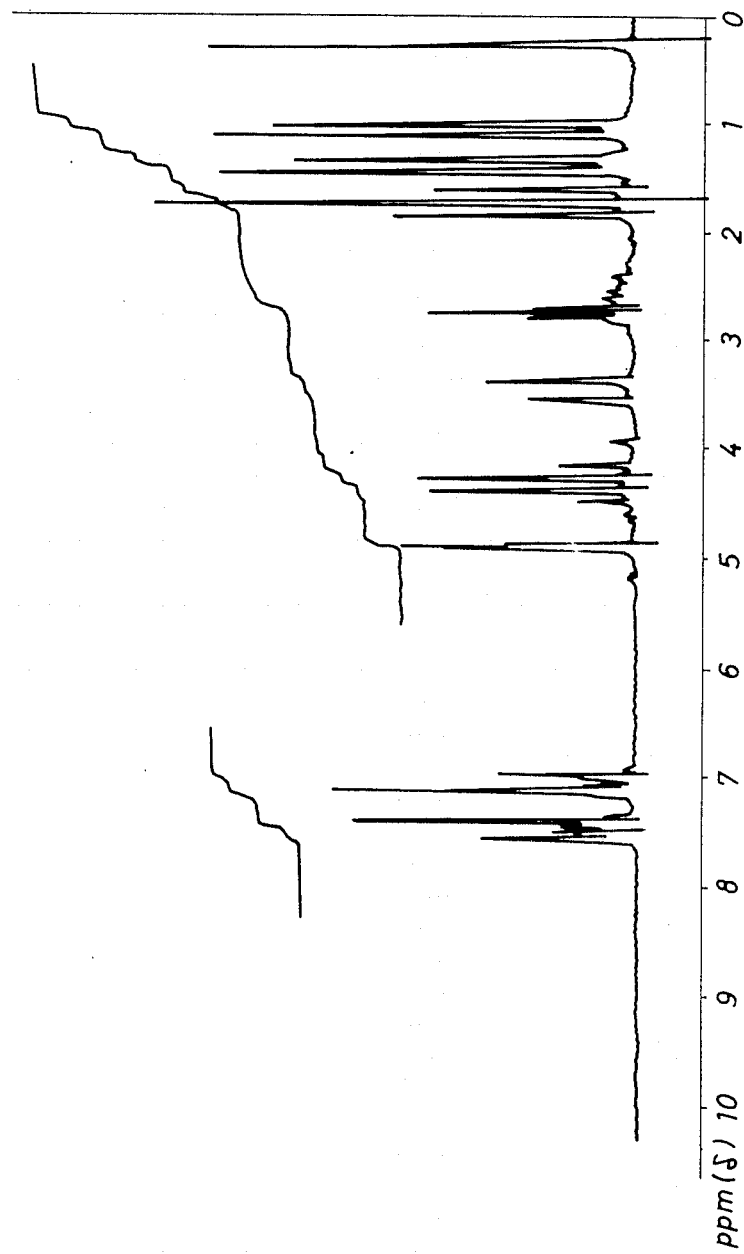
FIGS. 42 to 82 are the nuclear magnetic resonance (NMR) spectra of the derivatives of phenylacetic ester of the present invention.
Figure 43:
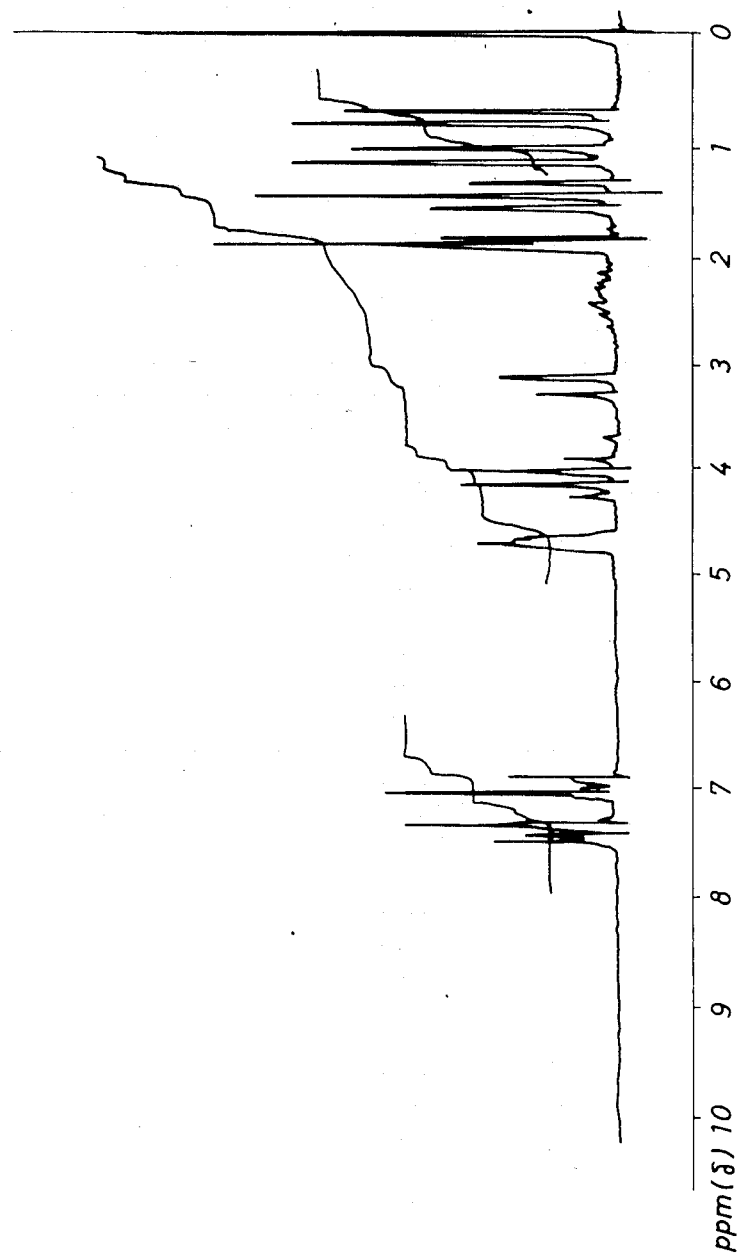
Figure 44:
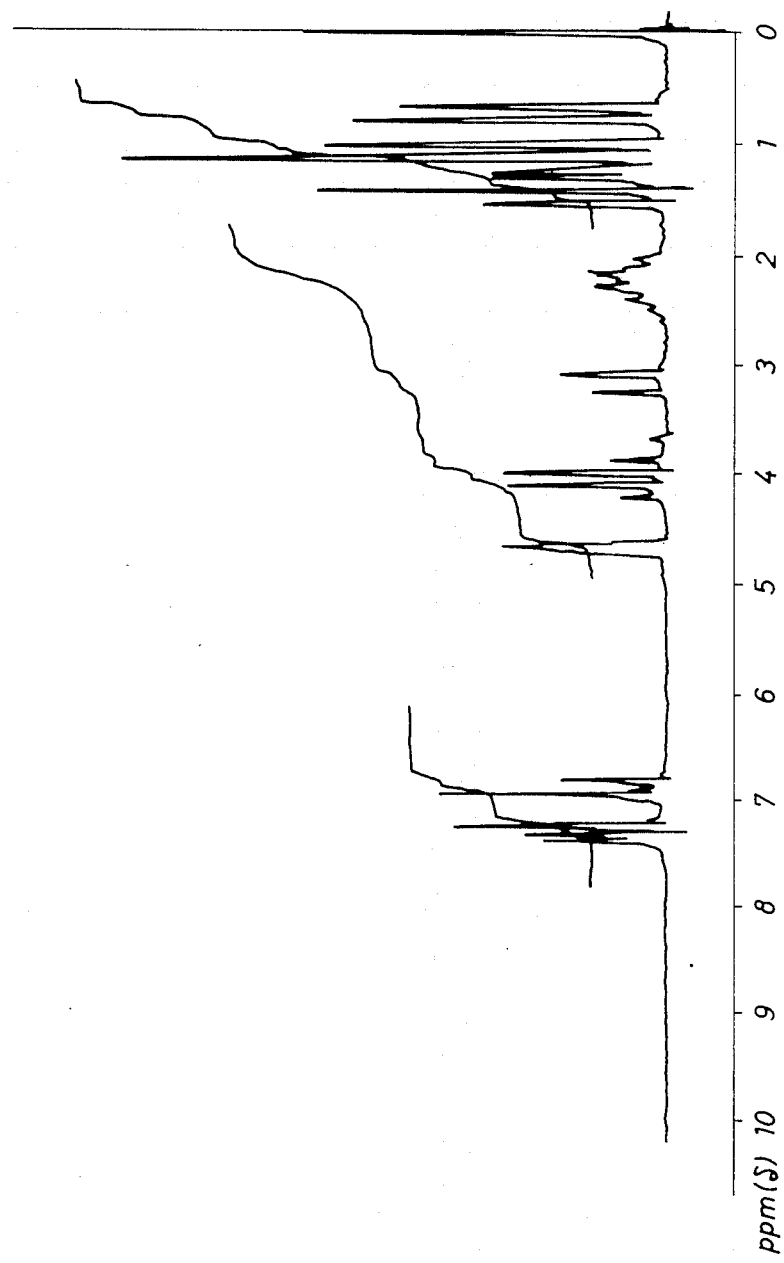
Figure 45:
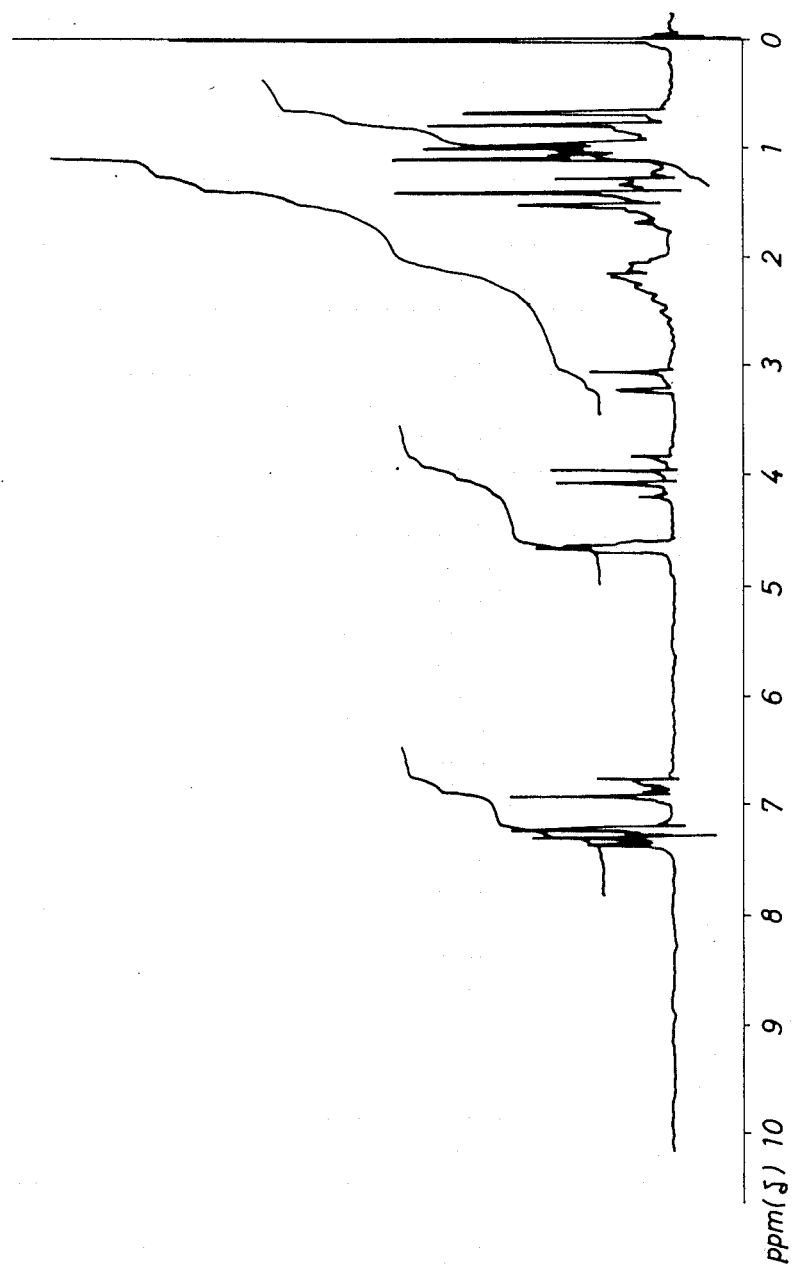
Figure 46:
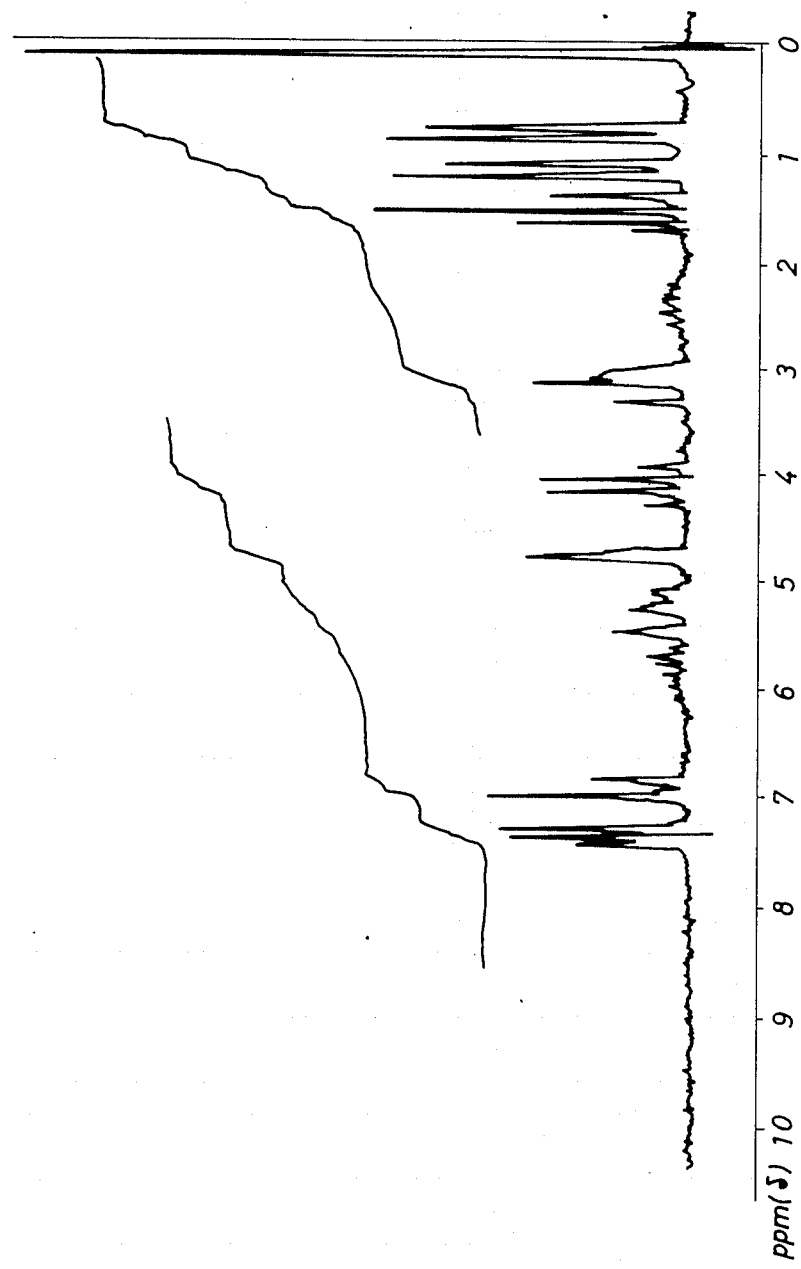
Figure 47:
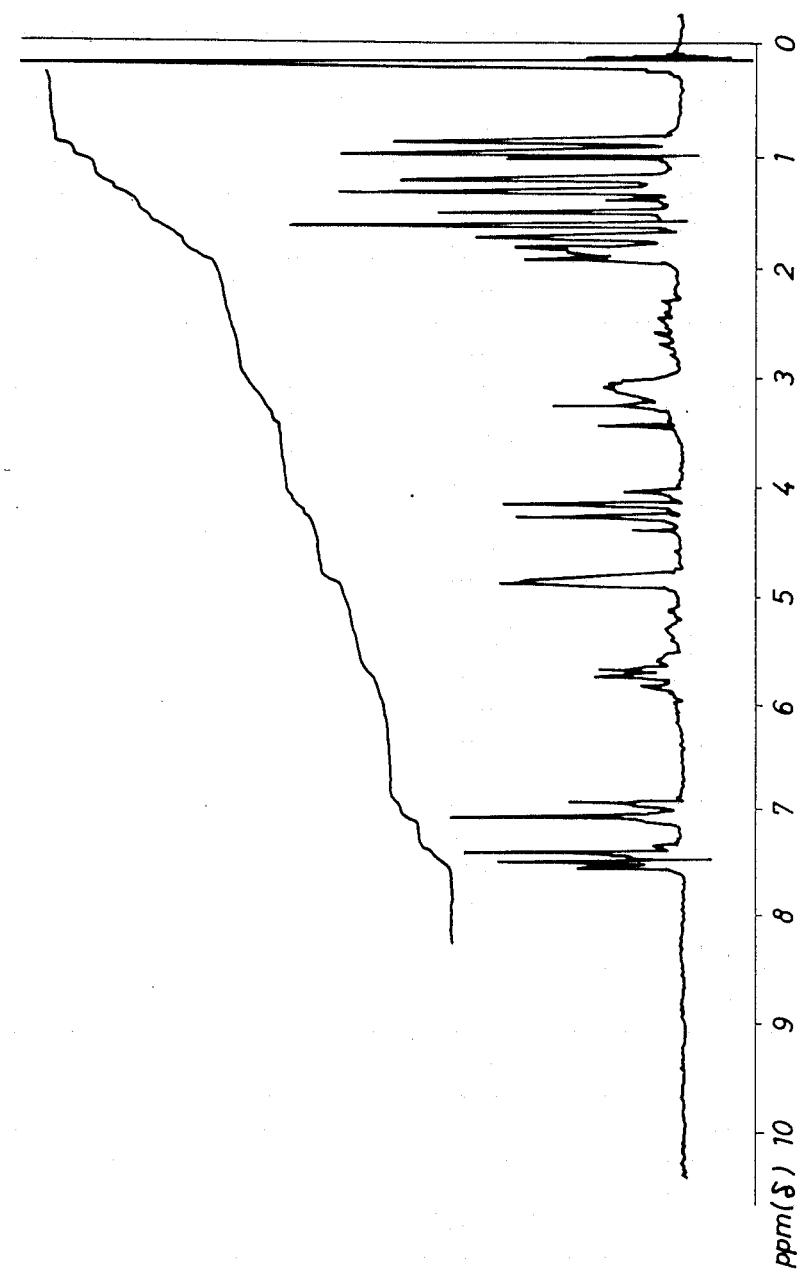
Figure 48:
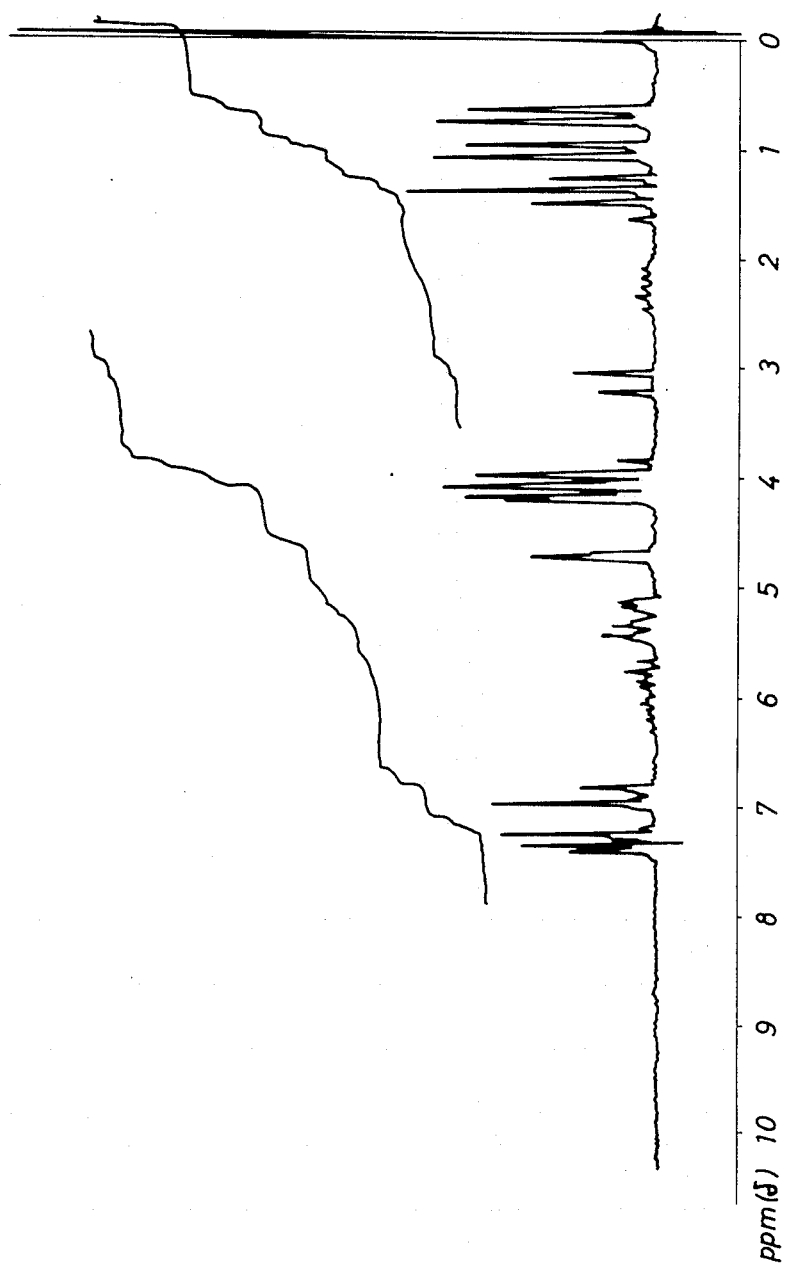
Figure 49:
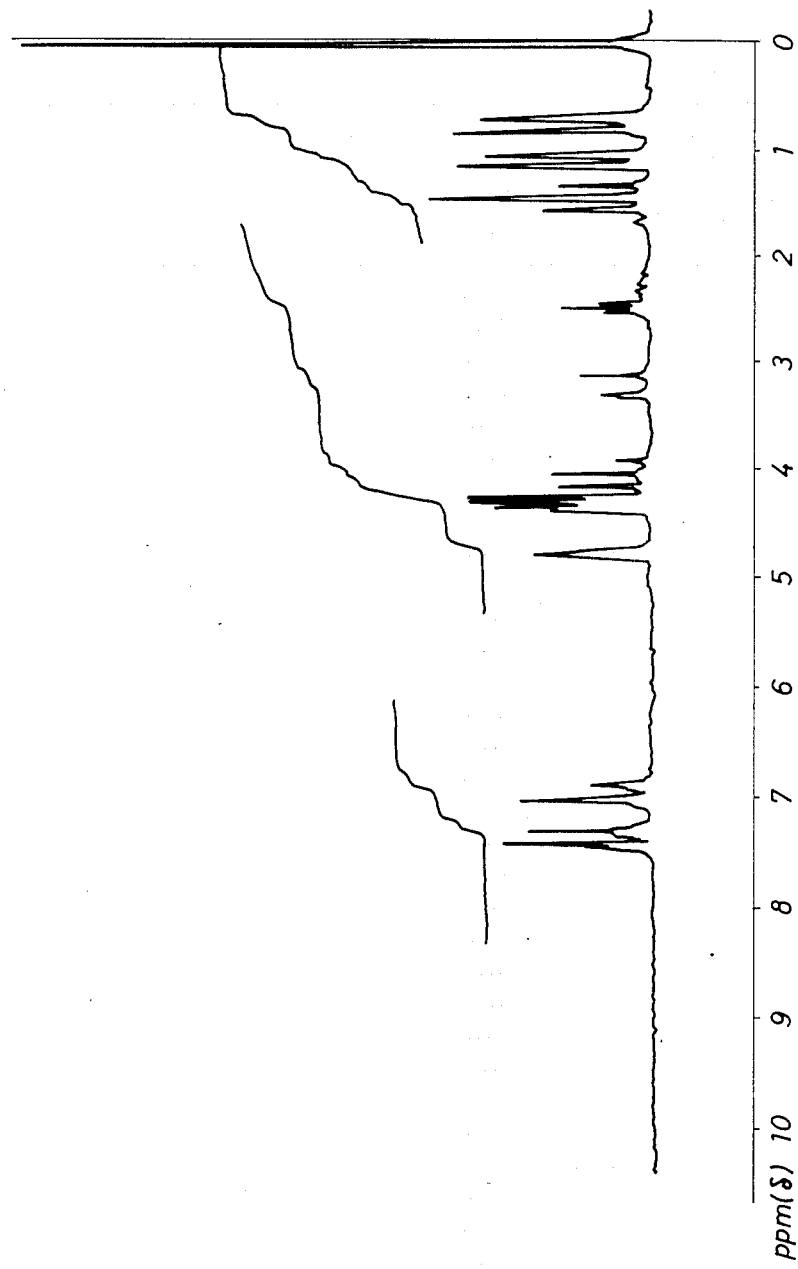
Figure 50:
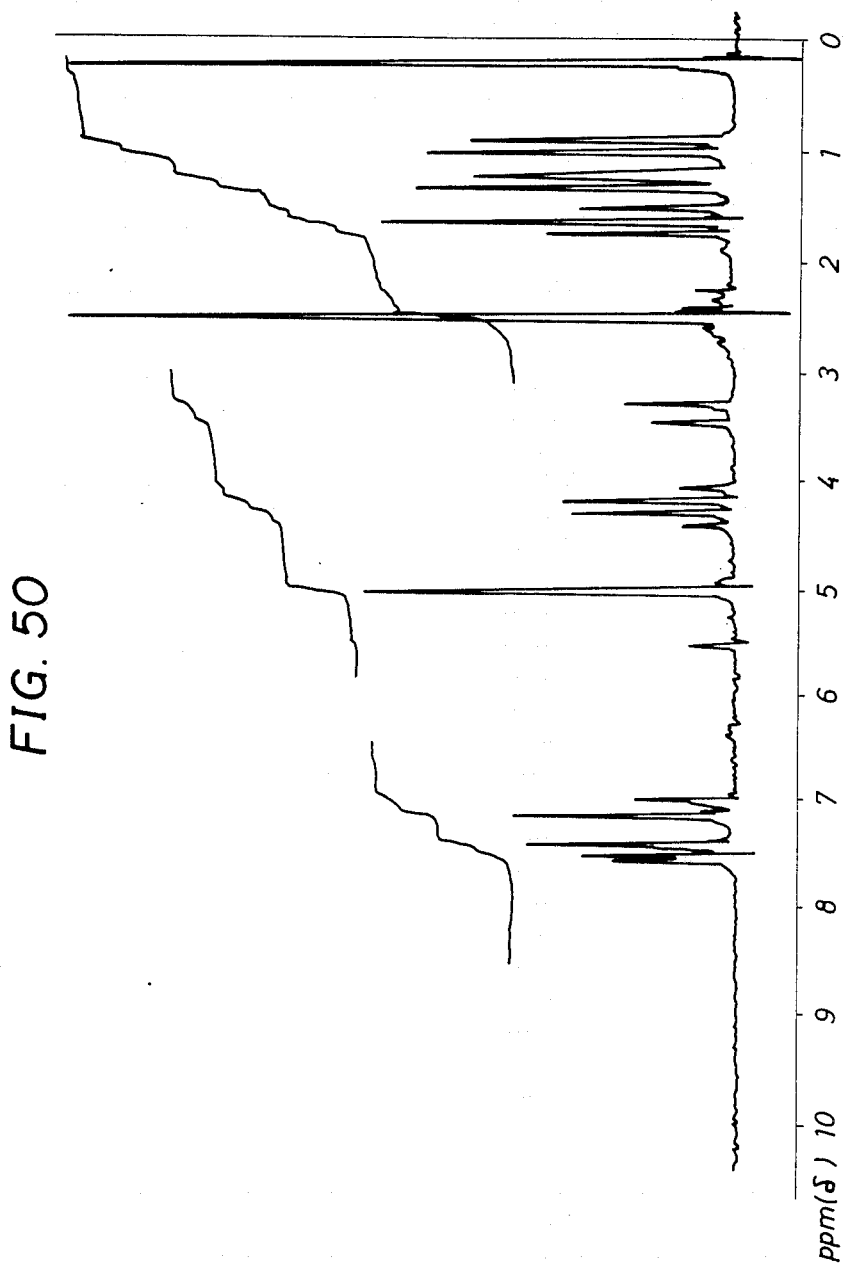
Figure 51:
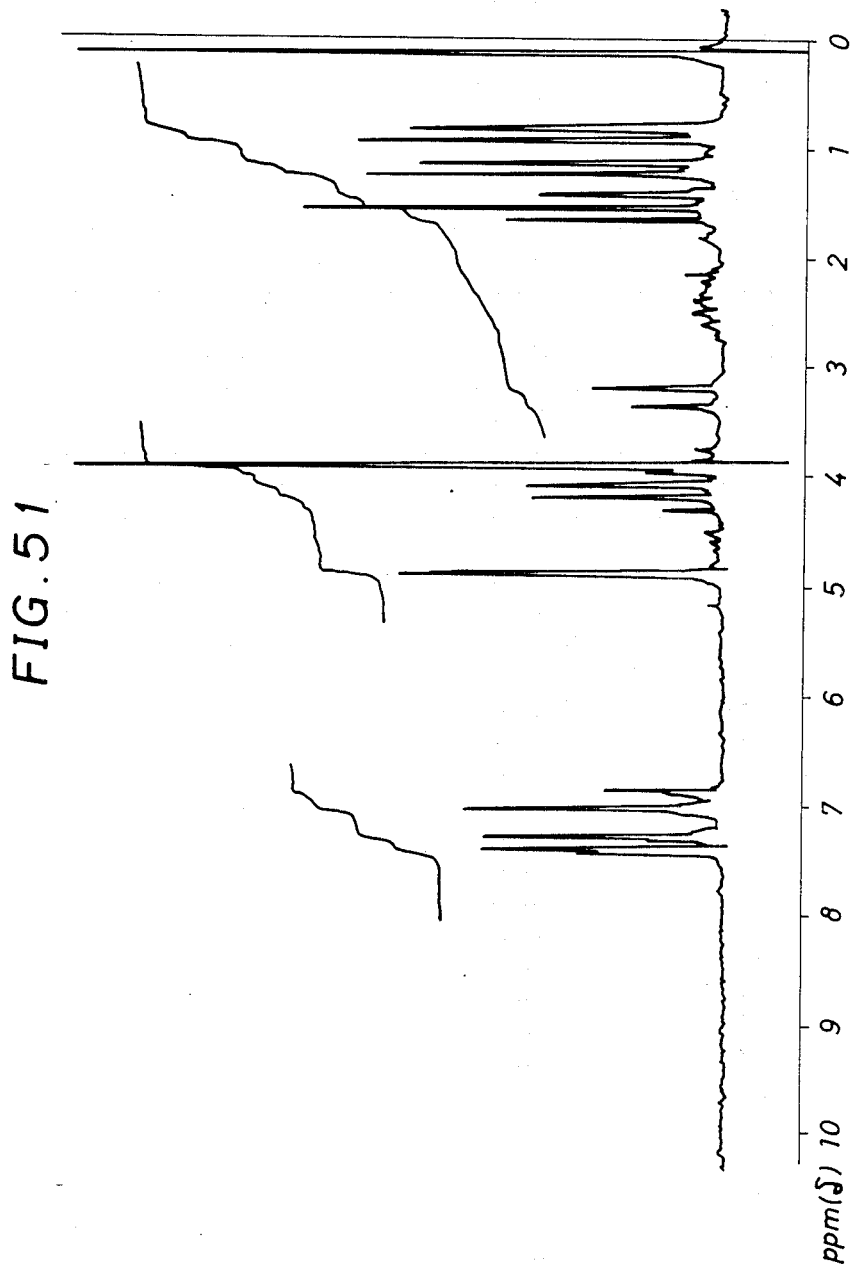
Figure 52:
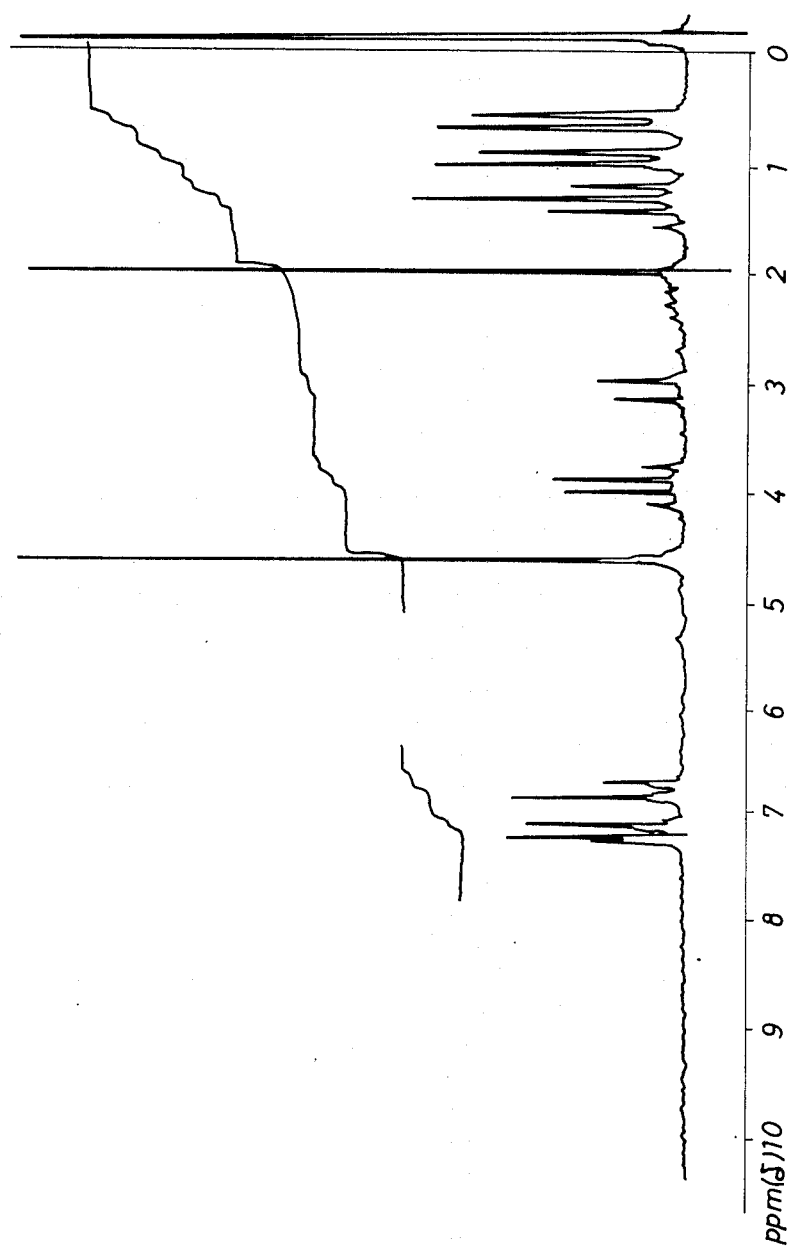
Figure 53:
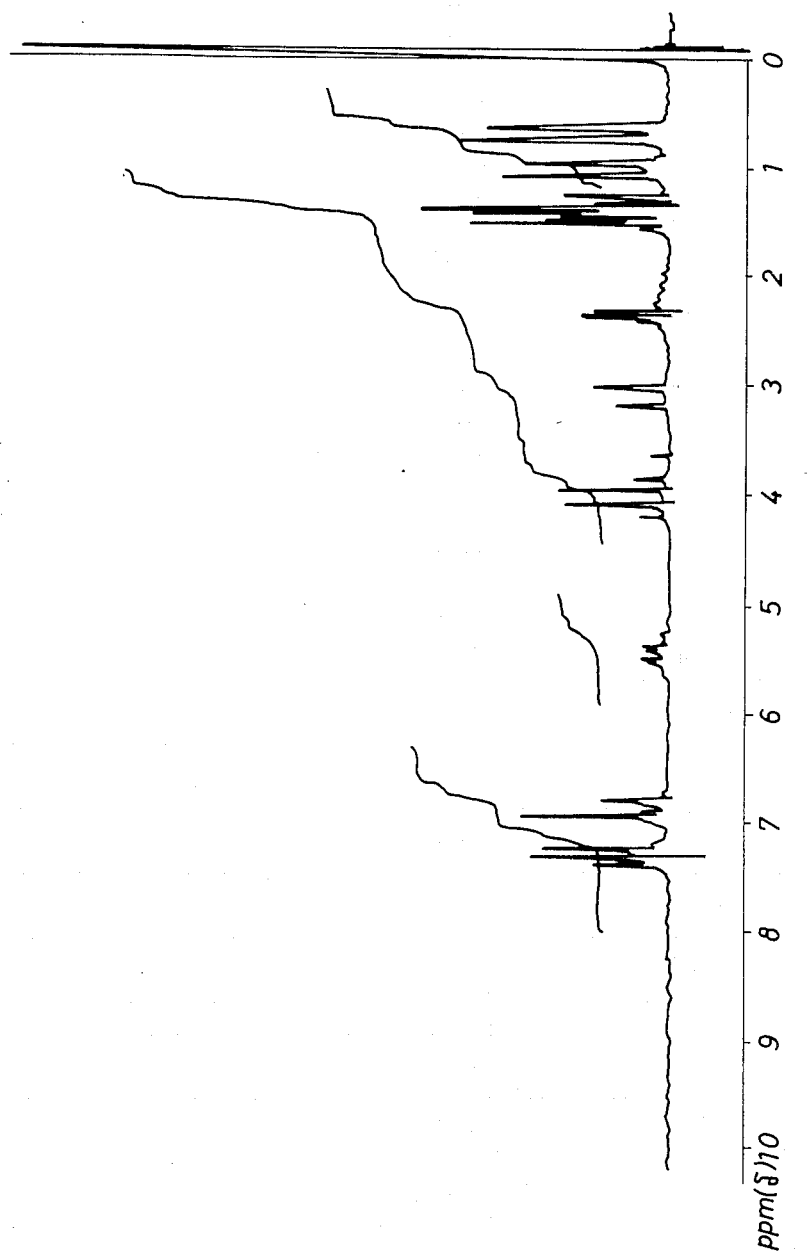
Figure 54:
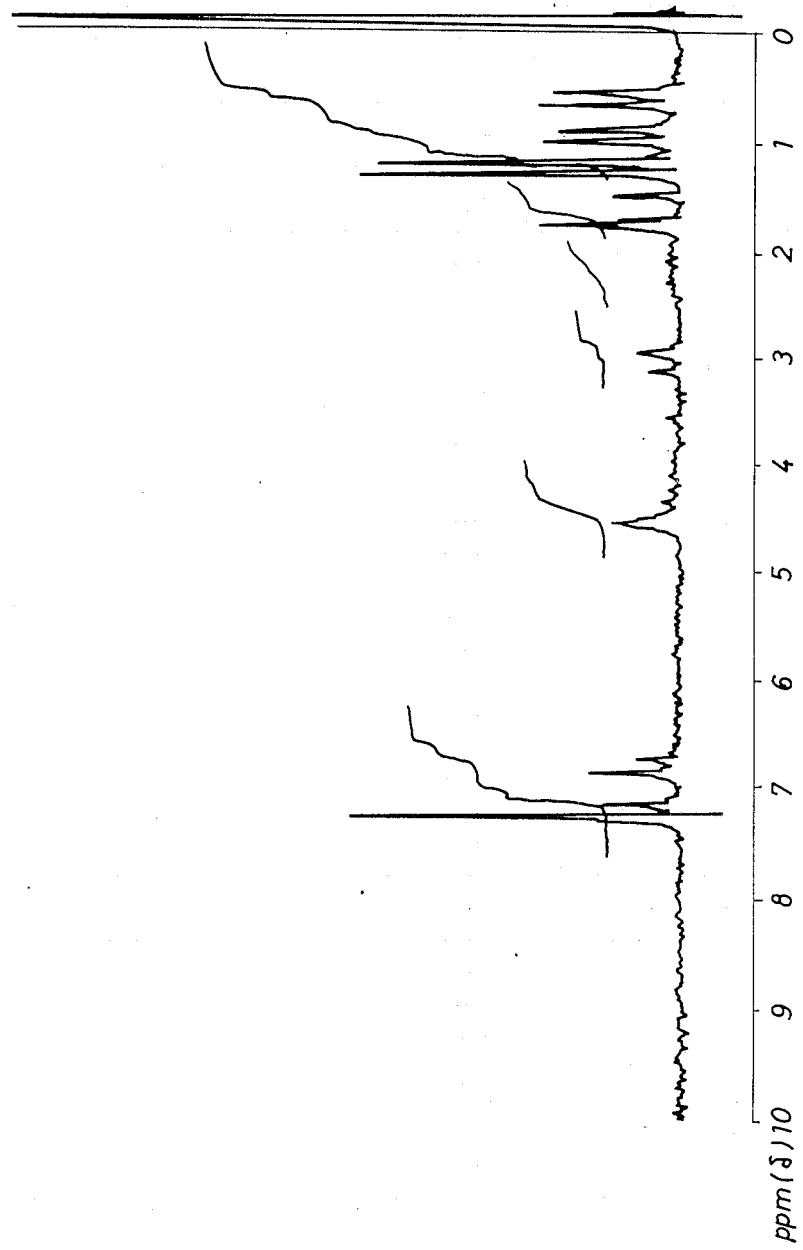
Figure 55:
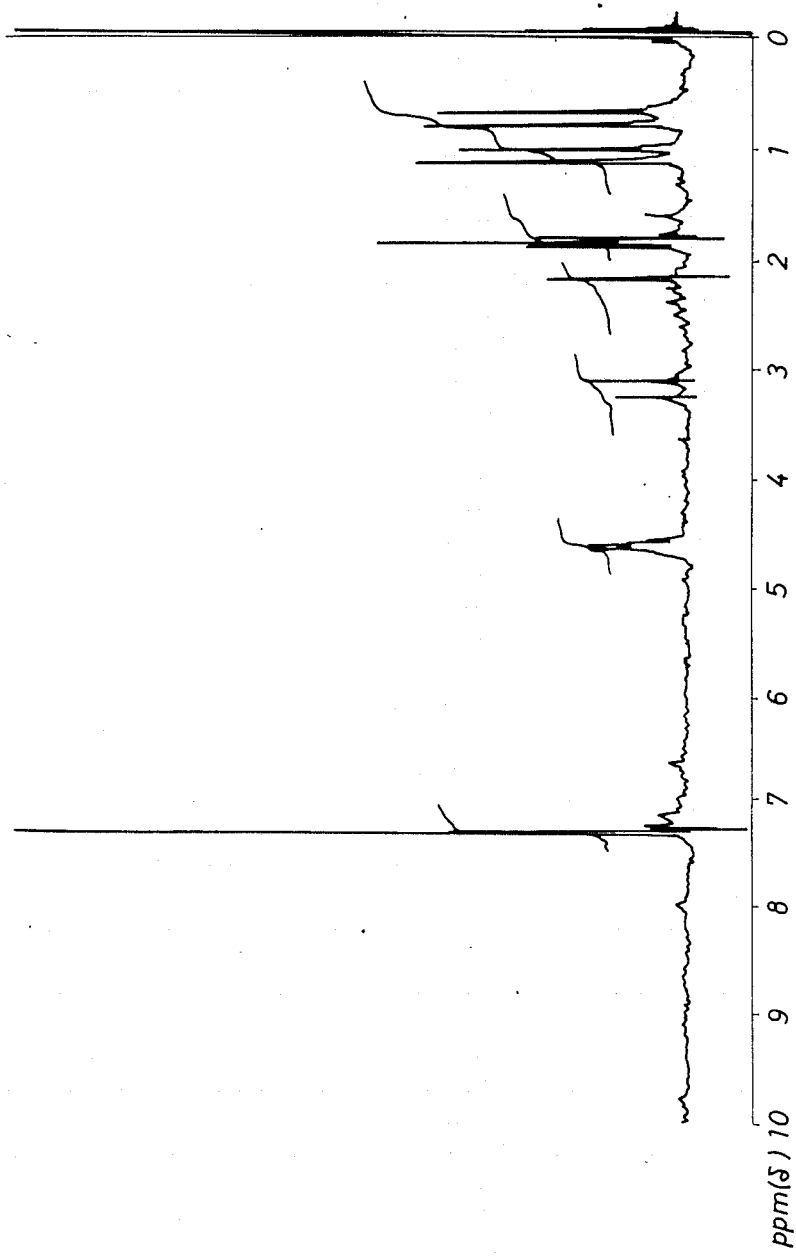
Figure 56:
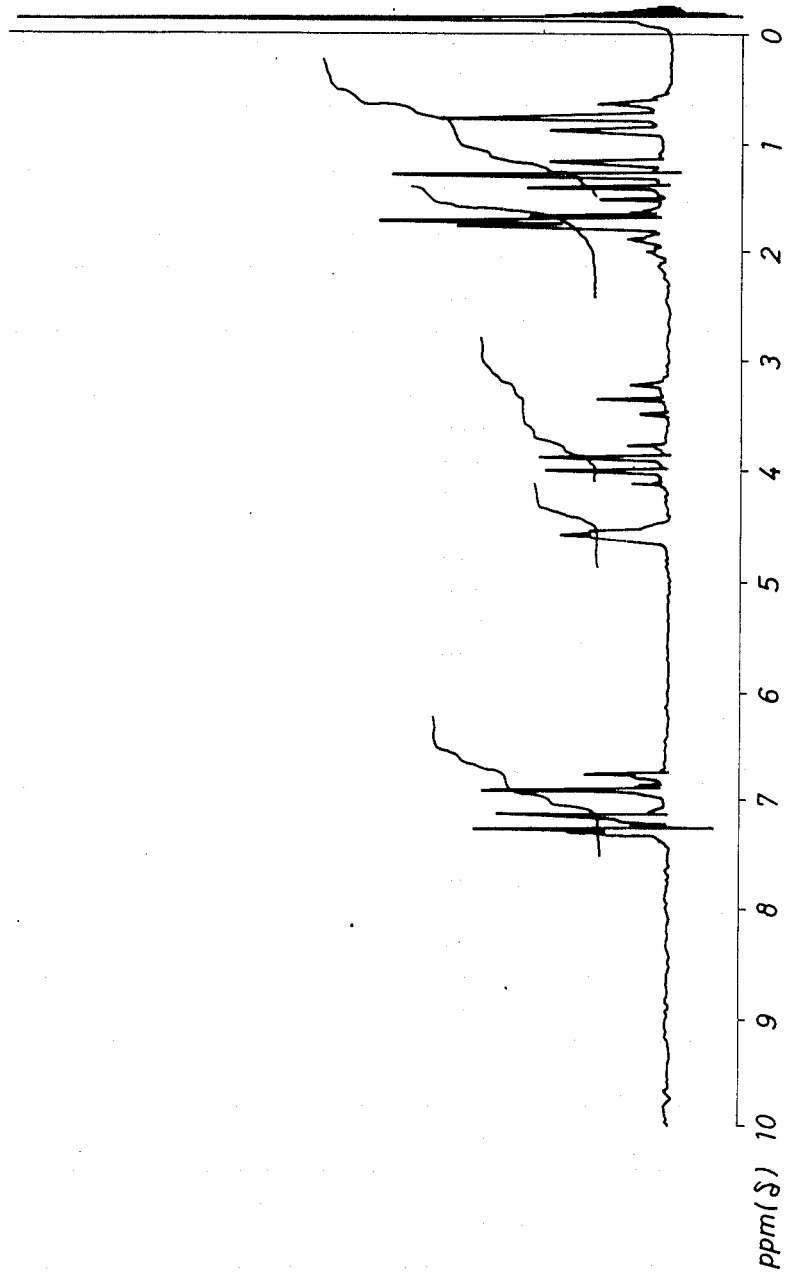
Figure 57:
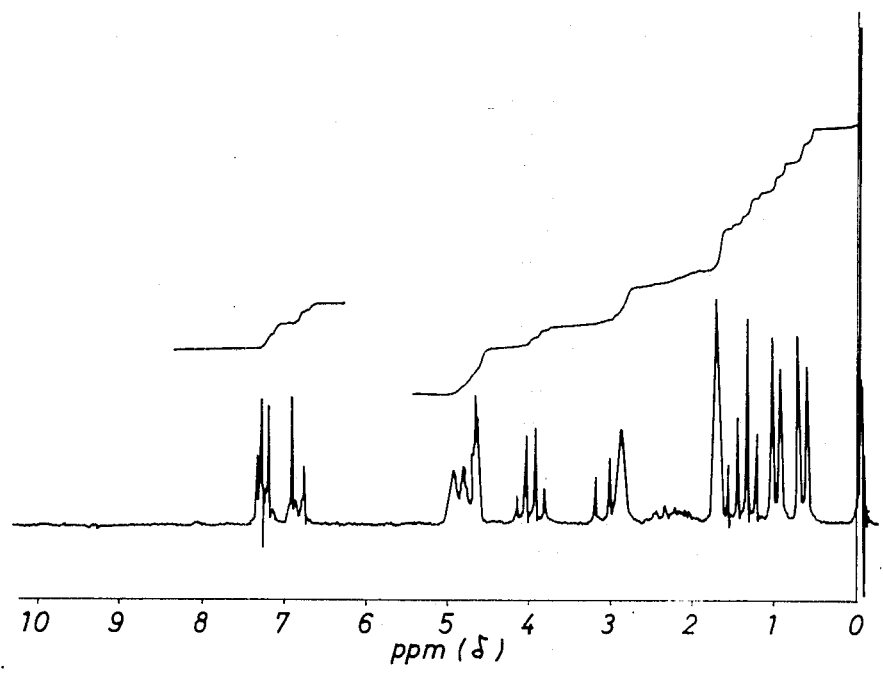
Figure 58:
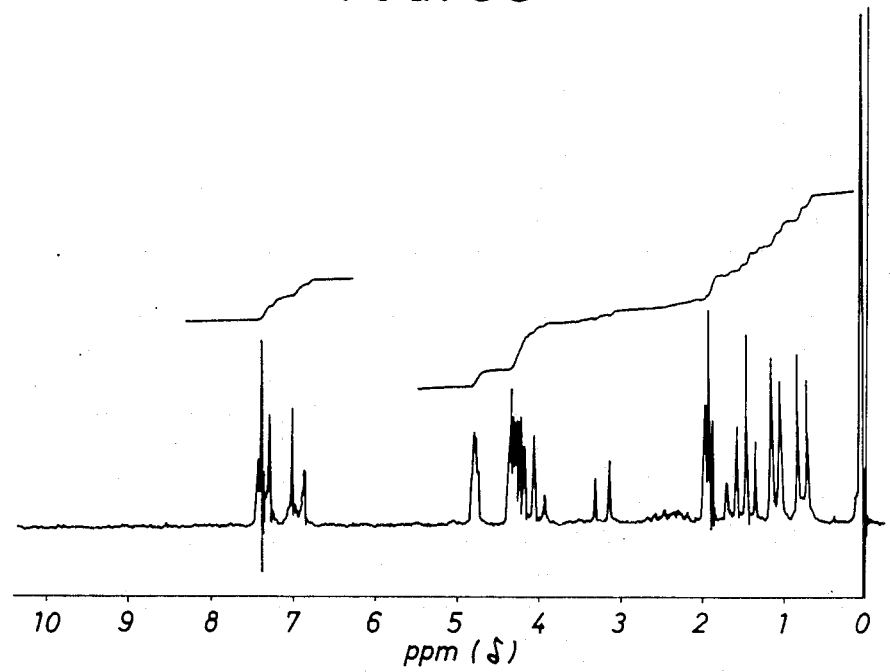
Figure 59:
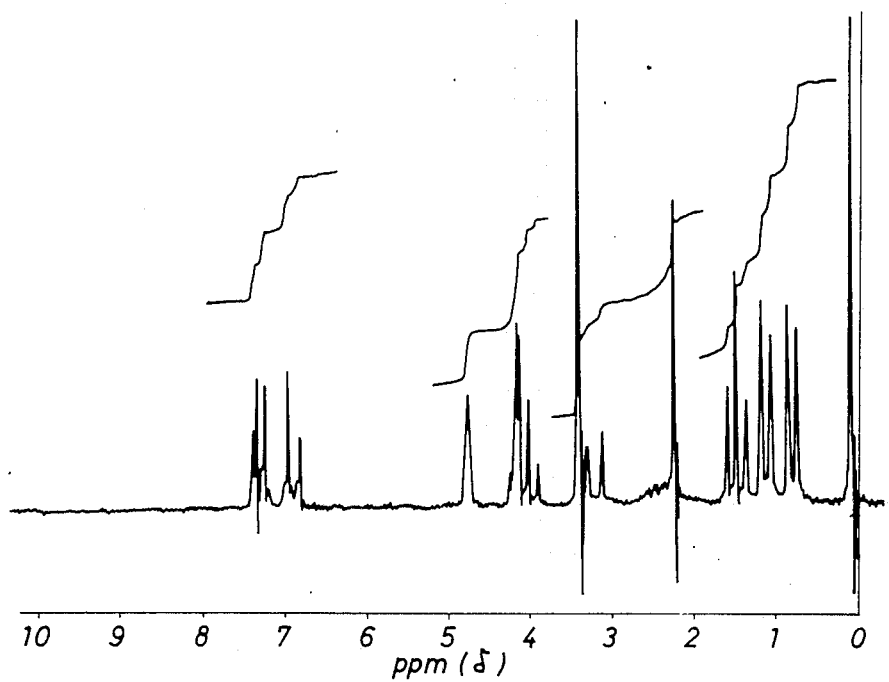
Figure 60:
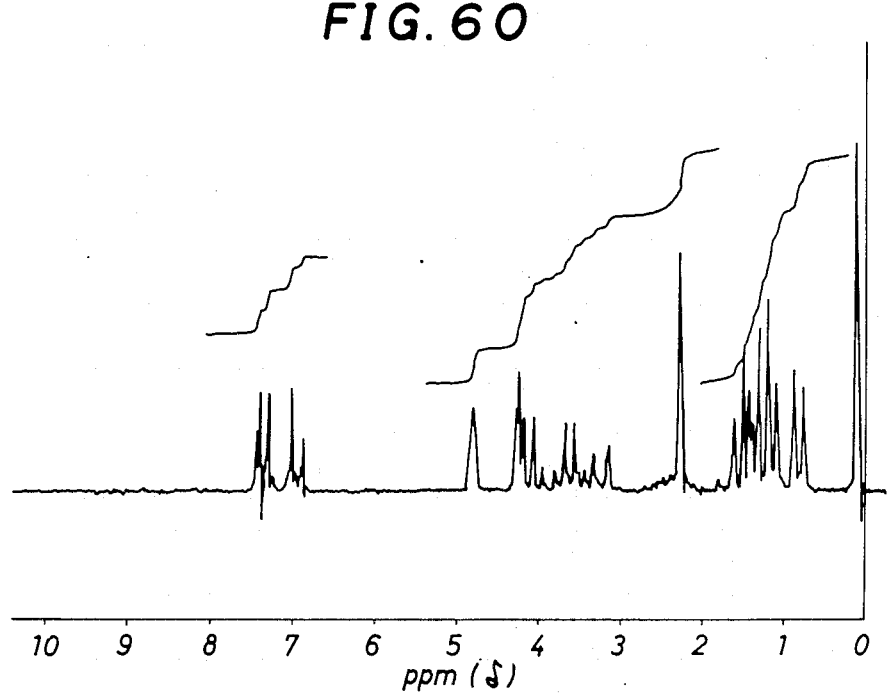
Figure 61:
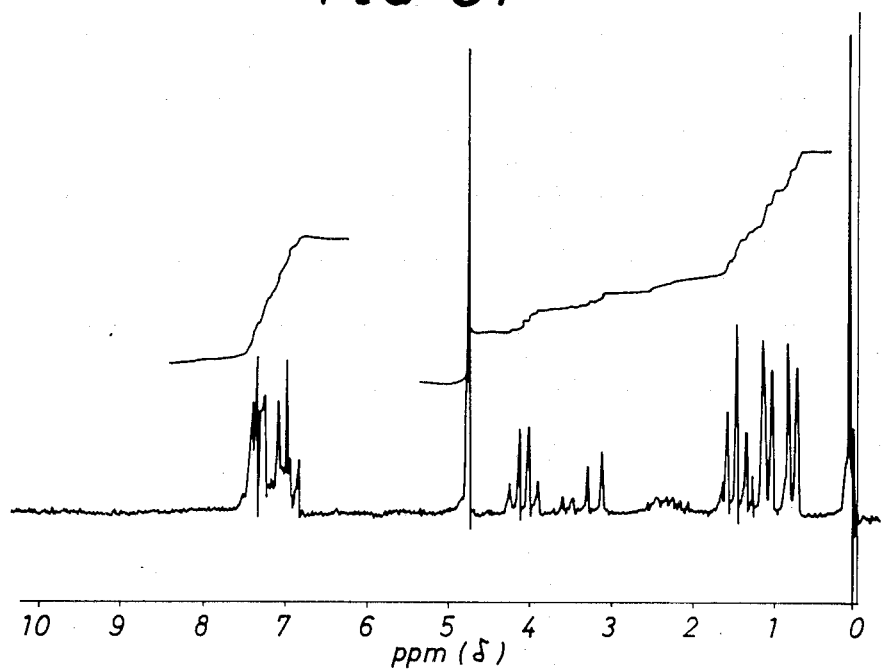
Figure 62:
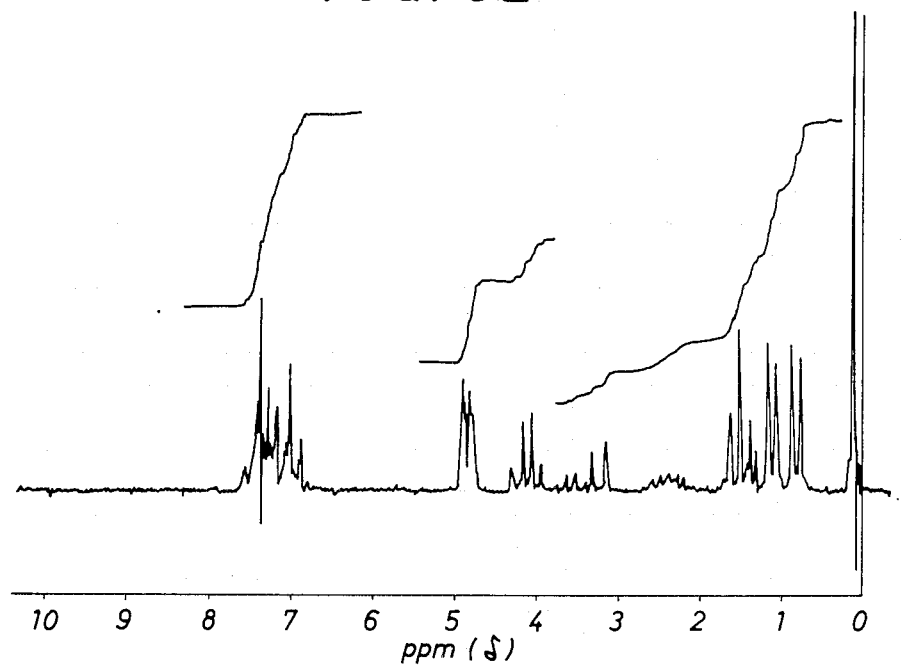
Figure 63:
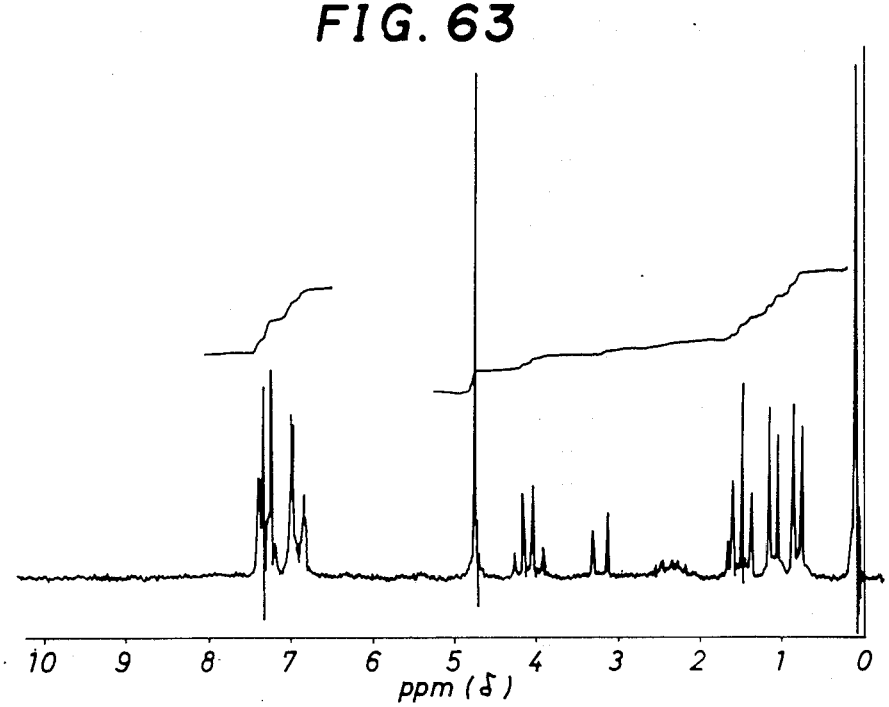
Figure 64:
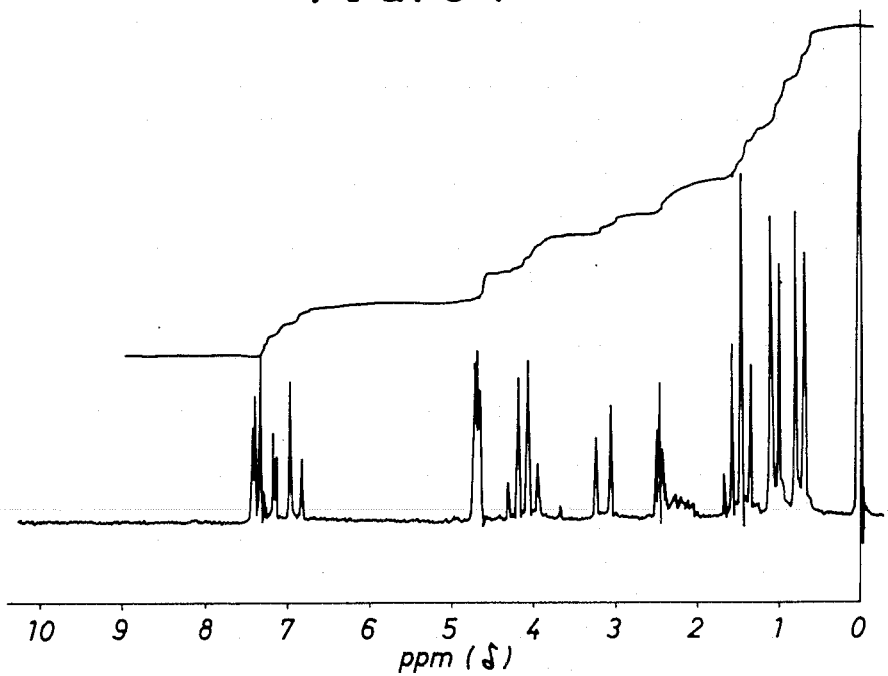

The infrared absorption spectrum of the thus obtained product and the nuclear magnetic resonance spectrum thereof (in CDCl$_3$ and TMS) are shown in FIGS. 1 and 42, respectively.

EXAMPLE 2

Synthesis of 2-butynyl 2-(3-chloro-4-ethoxyphenyl)isovalerate (Compound No. 24)

Into a solution of 0.15 g (0.55 mM) of Compound No. 2 (2-butynyl 2-(4-ethoxyphenyl)isovalerate) in 5 ml of chloroform, 0.76 g (5.5 mM) of thionyl chloride was added, and the mixture was stirred for 16 hours at room temperature. After condensing the reaction mixture, the condensate was subjected to silica gel column chromatography while using a 1:30 mixture of ethyl acetate and n-hexane as an eluent, thereby 0.14 g of the colourless and only compound No. 24 was obtained (yield: 80%).

Figure 24:
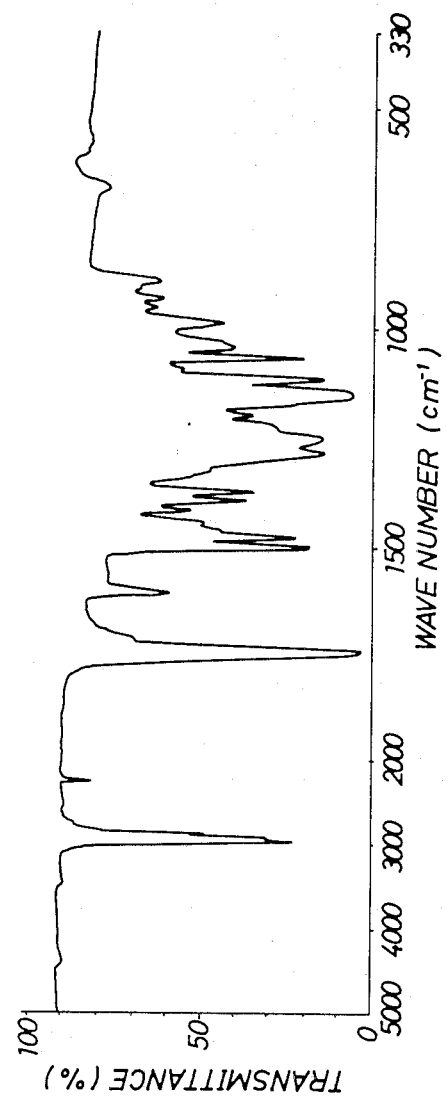
Figure 25:
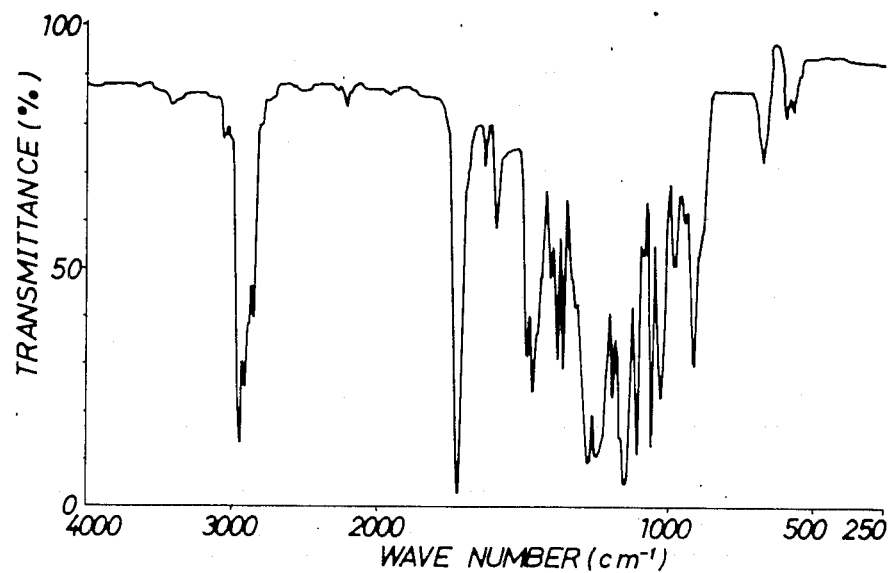
Figure 26:
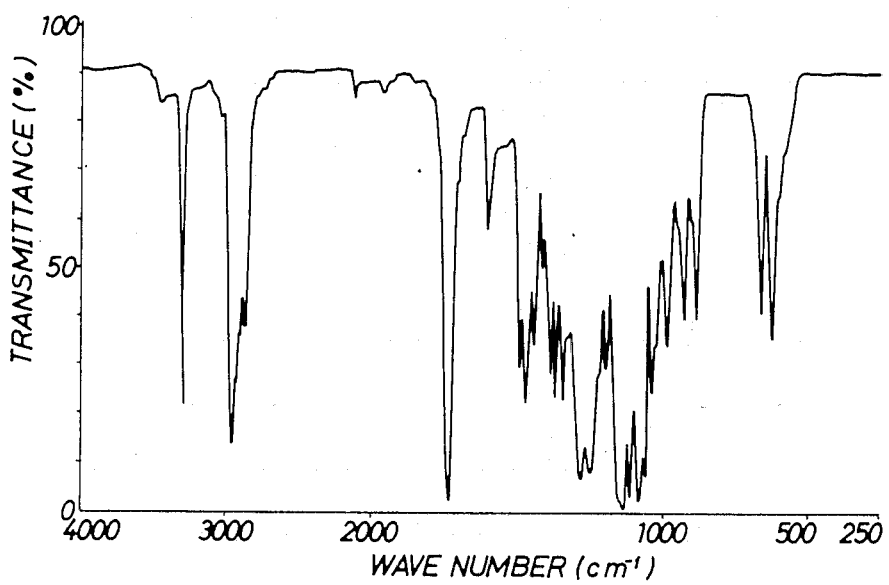
Figures 27, 28:
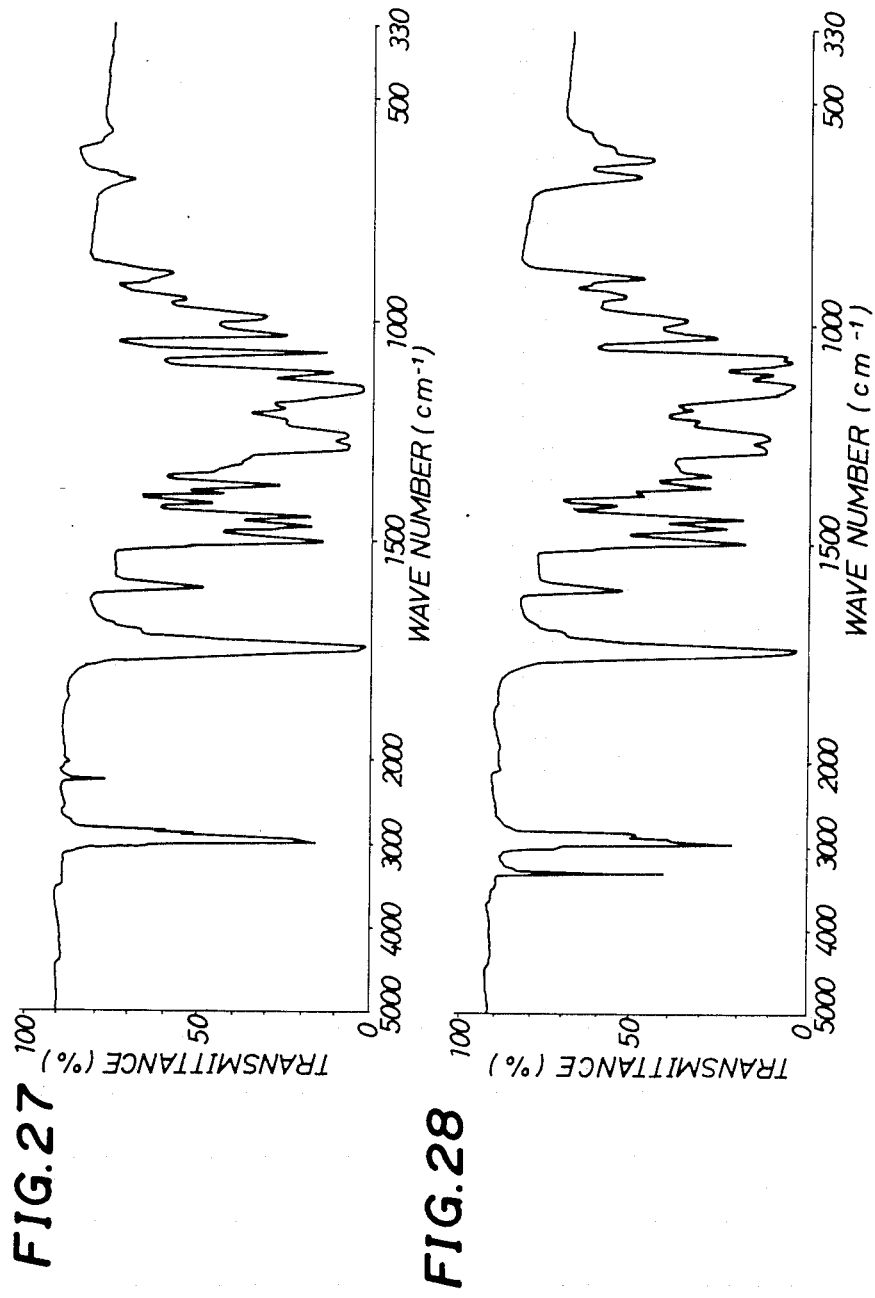
Figure 29:
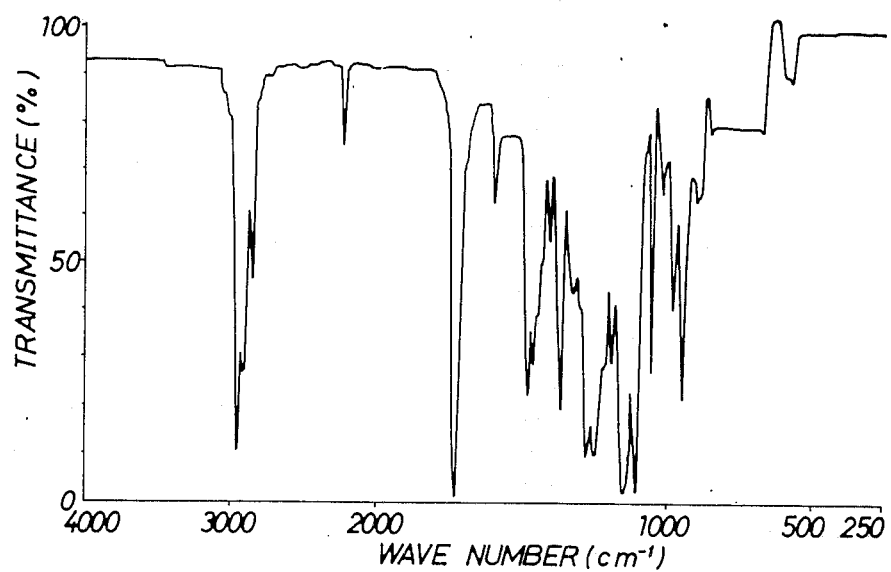
Figure 65:
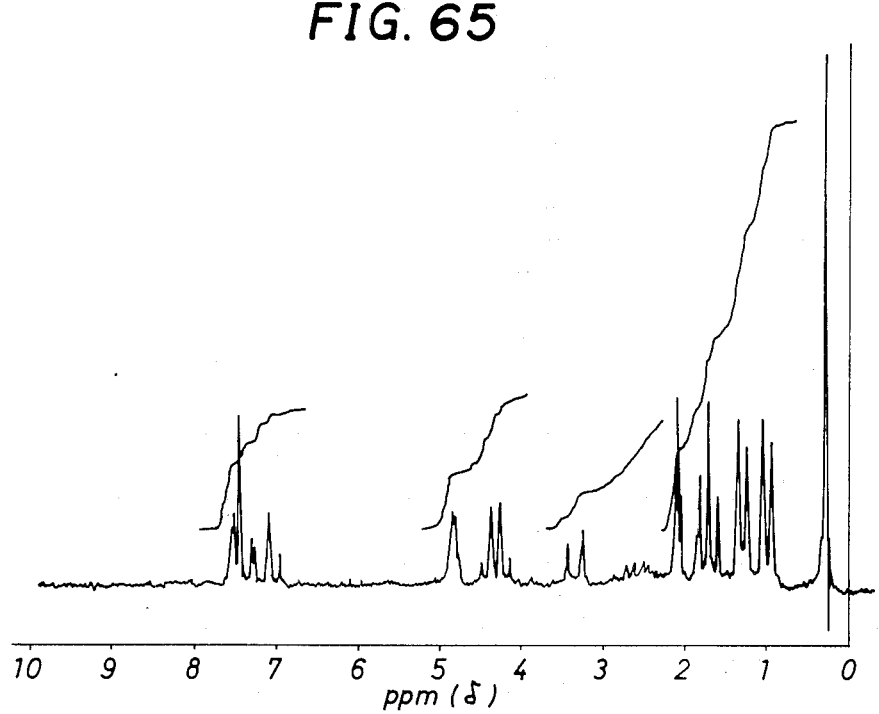
Figure 66:
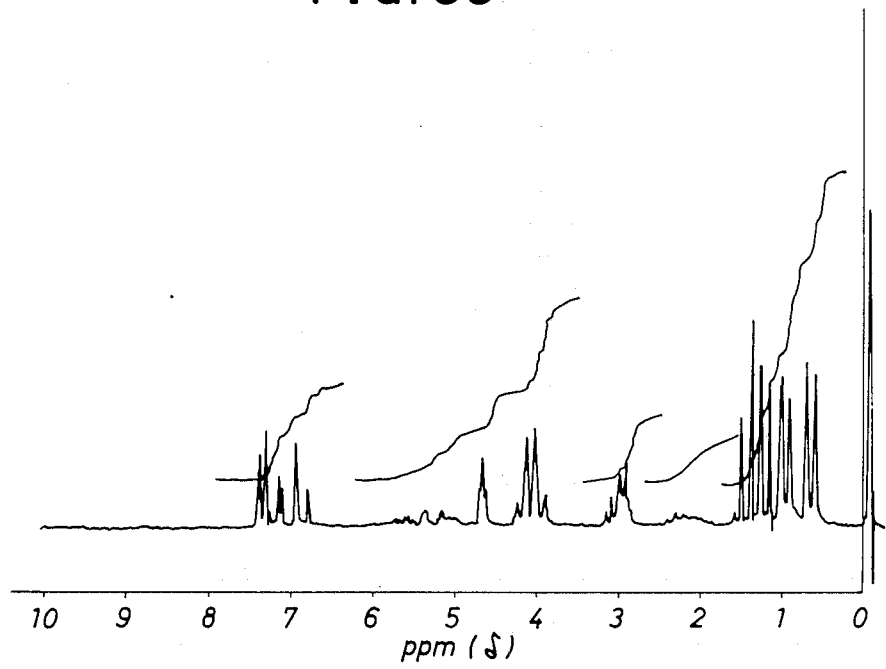
Figure 67:
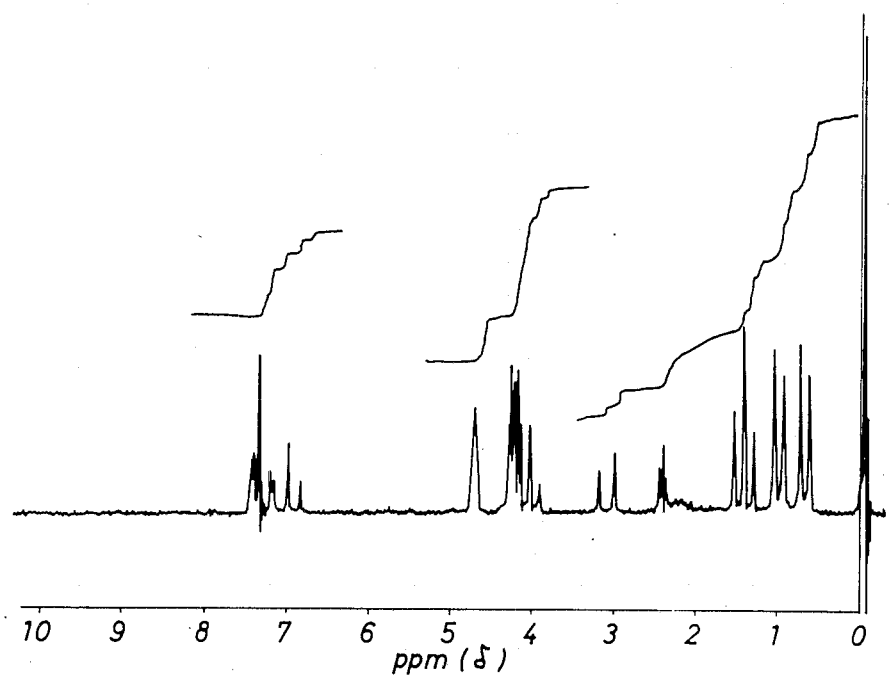
Figure 68:
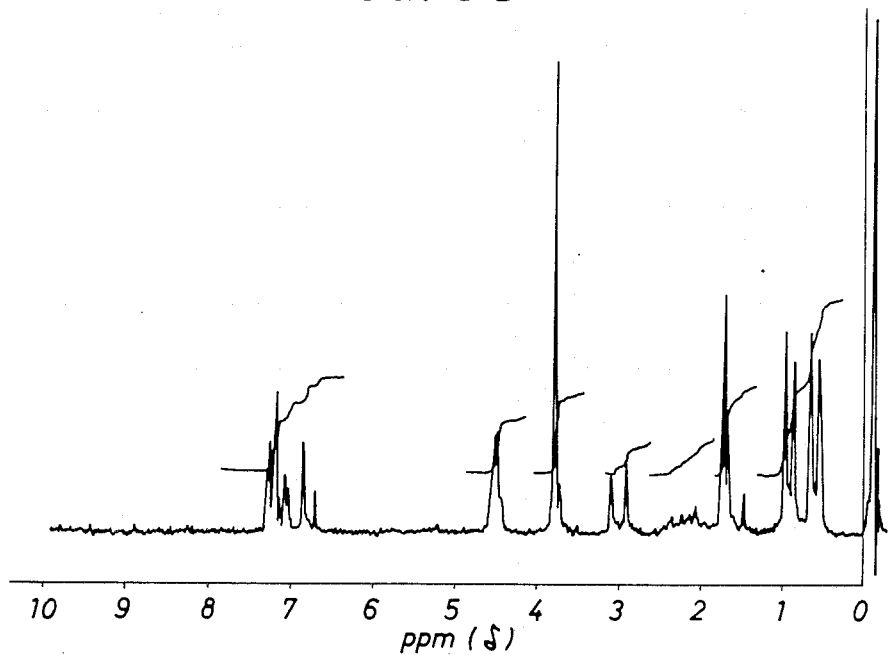
Figure 69:
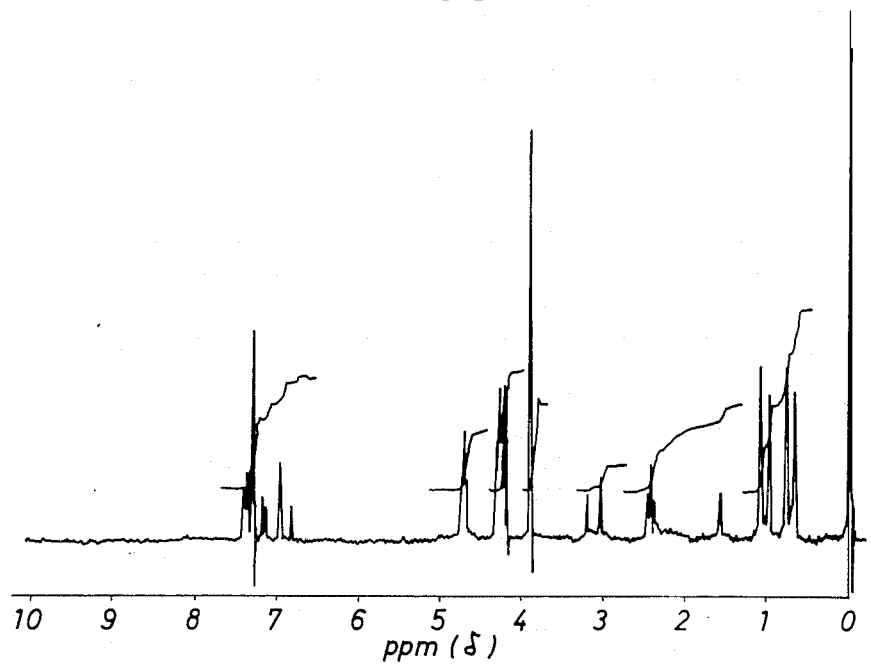
Figure 70:
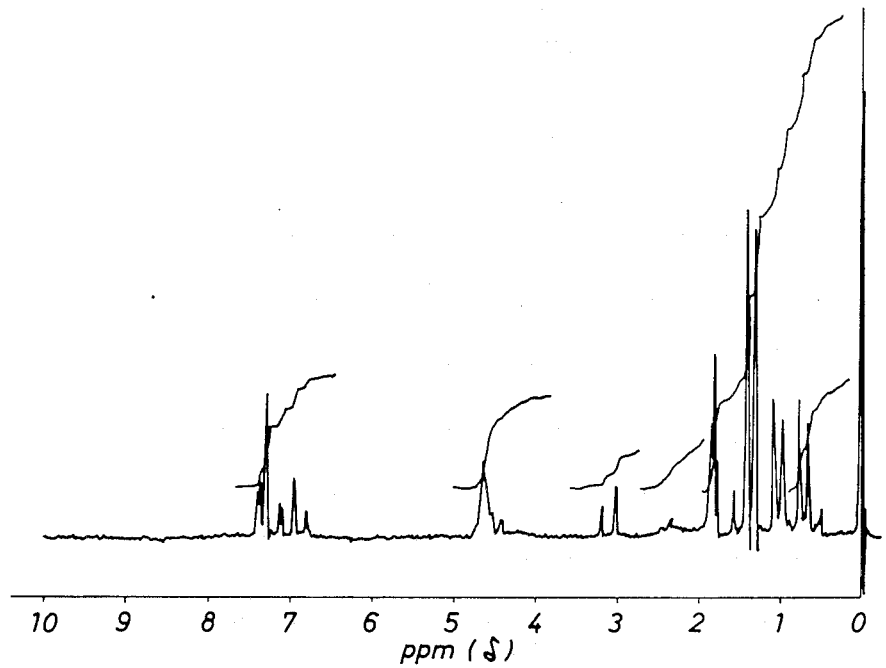
Figure 71:
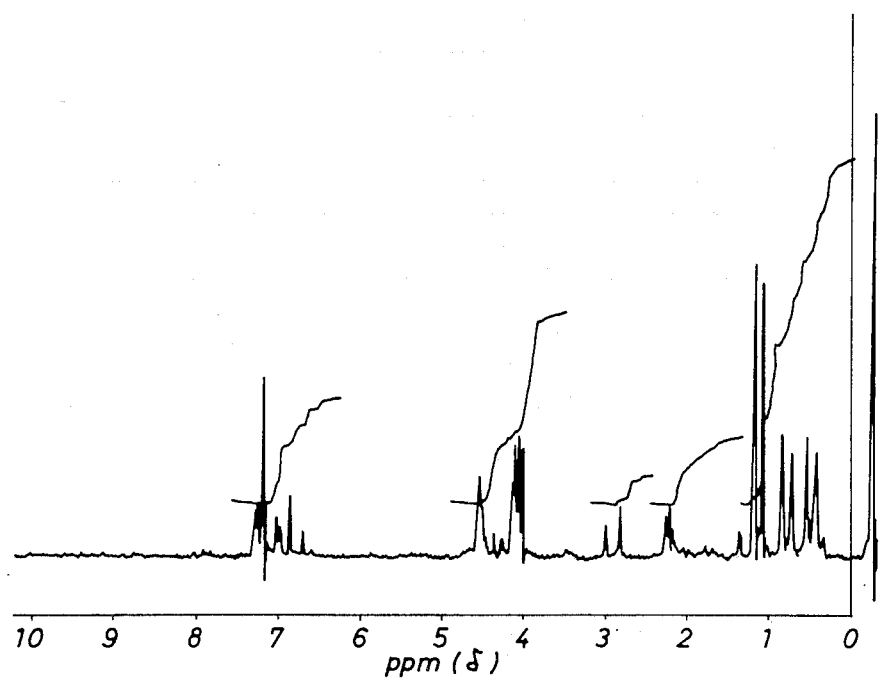

The infrared absorption spectrum of the thus obtained product and the nuclear magnetic resonance spectrum thereof (in CDCl$_3$ and TMS) are shown in FIGS. 24 and 65, respectively.

EXAMPLE 3

Synthesis of 2-butynyl 2-(3-bromo-4-ethoxyphenyl)isovalerate (Compound No. 31)

Into a solution of 0.15 g (0.67 mM) of 2-(4-ethoxyphenyl)isovaleric acid in 3 ml of chloroform, 0.24 g (1.35 mM) of N-bromosuccinimide was added, and the mixture was heated for 3 hours in the presence of a catalytic amount of anhydrous aluminum chloride under a reflux condition. The oily substance obtained by condensing the reaction mixture was subjected to silica gel column chromatography while using a 1:3 mixture of ethyl acetate and n-hexane as an eluent, thereby 0.12 g of 2-(3-bromo-4-ethoxyphenyl)isovaleric acid was obtained as a colourless and oily substance (yield: 60%).

After dissolving the thus obtained oily substance in 1.2 ml of anhydrous methylene chloride and adding a catalytic amount of dimethylformamide and 0.1 g (0.74 mM) of thionyl chloride to the solution, the thus prepared mixture was stirred for 2 hours in an oil bath at 40° C. Thereafter, an excess of thionyl chloride and methylene chloride were distilled off from the reaction mixture under a reduced pressure, whereby 2-(3-bromo-4-ethoxyphenyl)isovaleric chloride was obtained as an oily substance.

After dissolving the thus obtained oily substance in 1.3 ml of anhydrous benzene, a solution of 0.0376 g (0.54 mM) of 2-butyn-1-ol in 1.3 ml of anhydrous benzene and 0.0372 g of pyridine were added to the thus prepared solution, the thus prepared mixture was stirred for 2 hours at room temperature.

Then, iced water was added to the reaction mixture, and the aqueous mixture was extracted with benzene. After washing the extract with an aqueous 5% hydrochloric acid, a saturated aqueous solution of sodium hydrogencarbonate and a saturated aqueous solution of sodium chloride successively and drying the thus washed extract over anhydrous sodium sulfate, benzene was distilled off from the dried extract to obtain an oily substance. The oily substance was subjected to silica gel column chromatography while using a 1:40 mixture of ethyl acetate and n-hexane as an eluent to obtain 0.0721 g of compound No. 31 (yield: 51.3%).

Figures 30, 31:
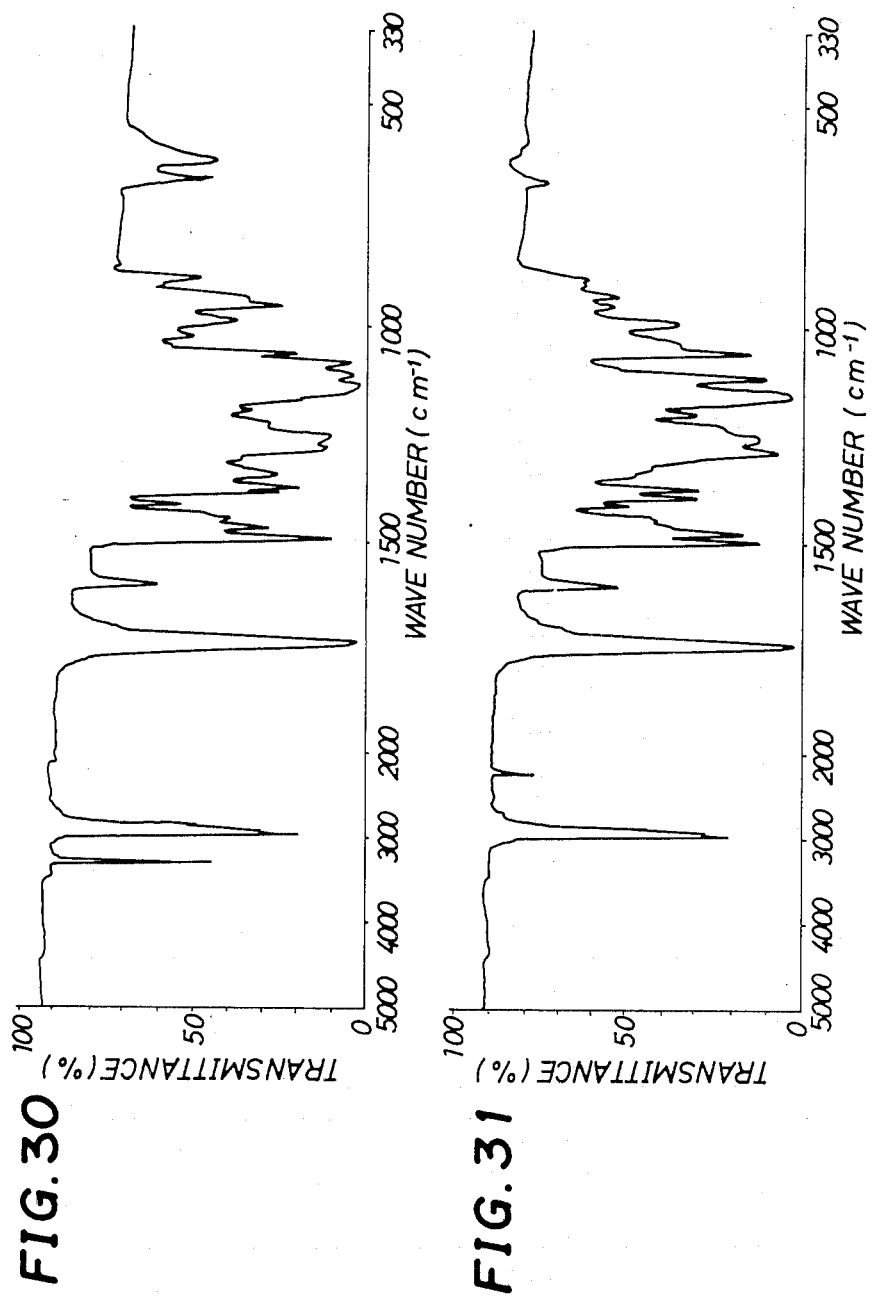
Figure 32:
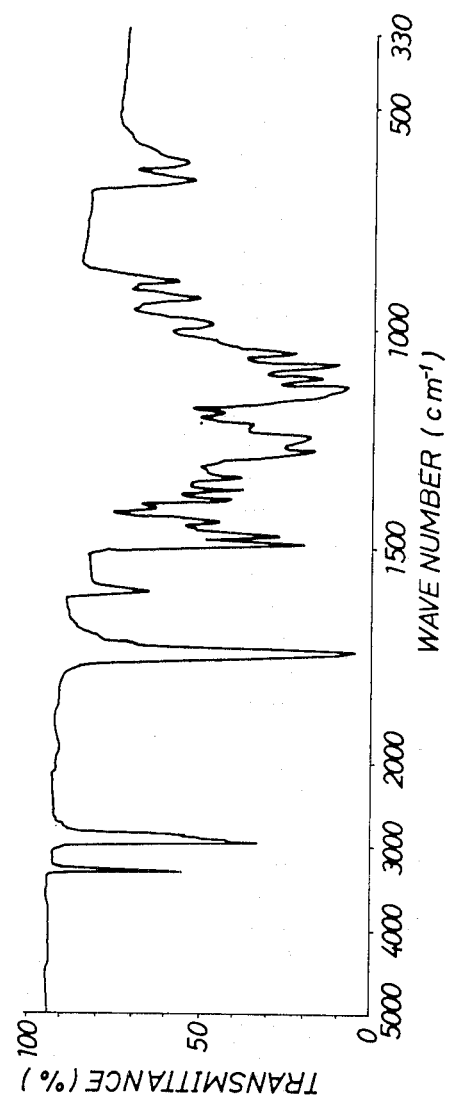
Figure 33:
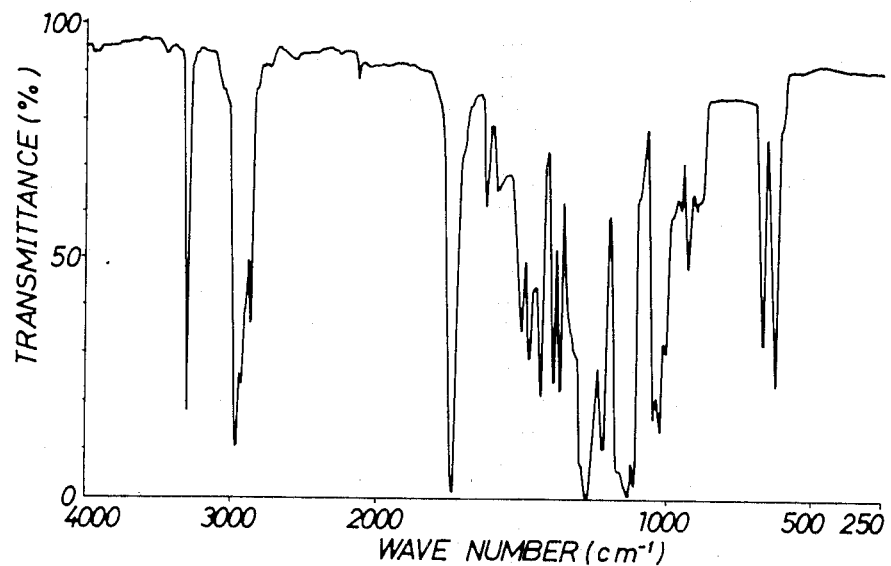
Figure 72:
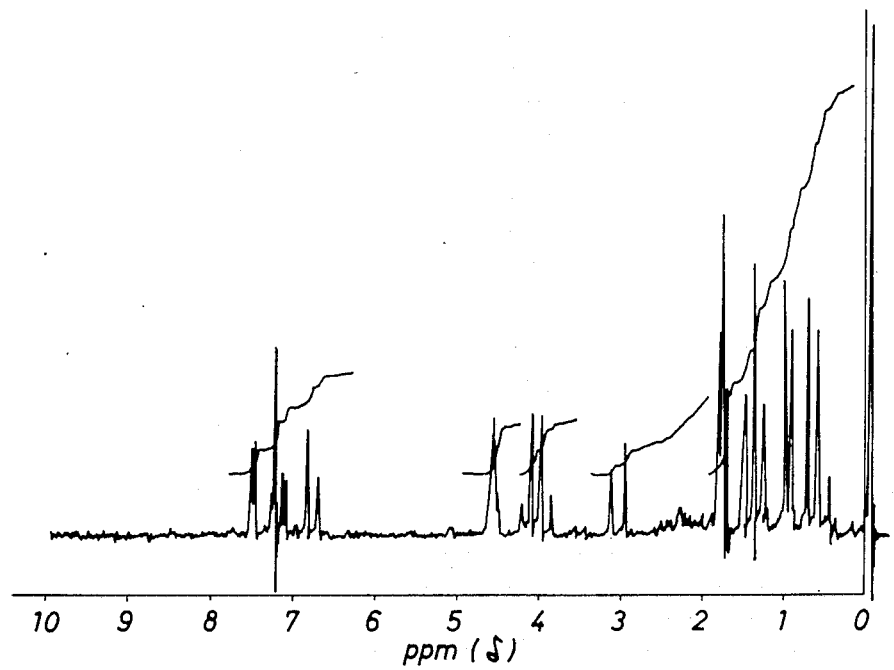
Figure 73:
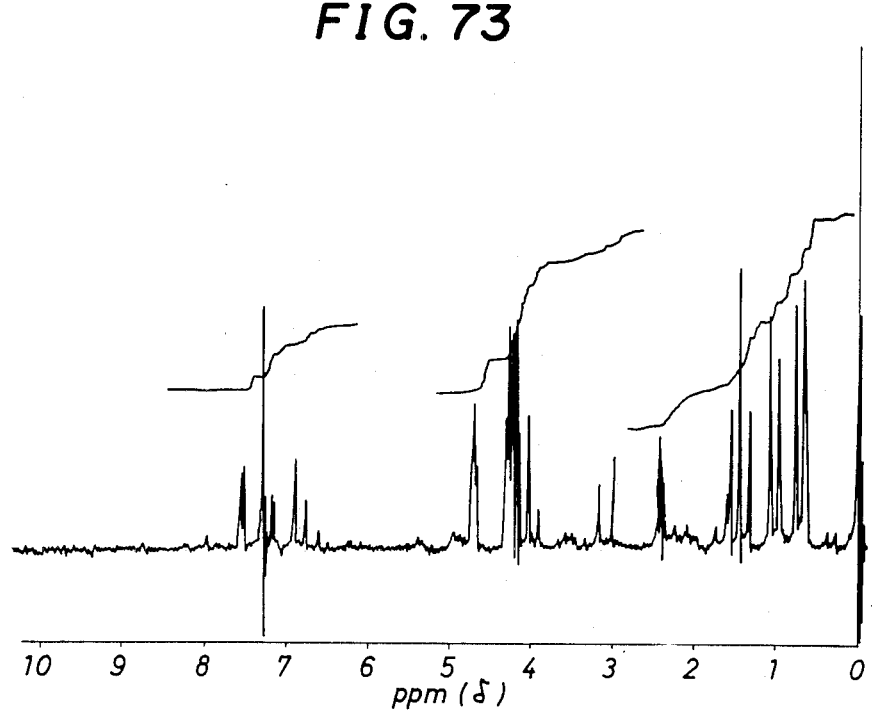
Figure 74:
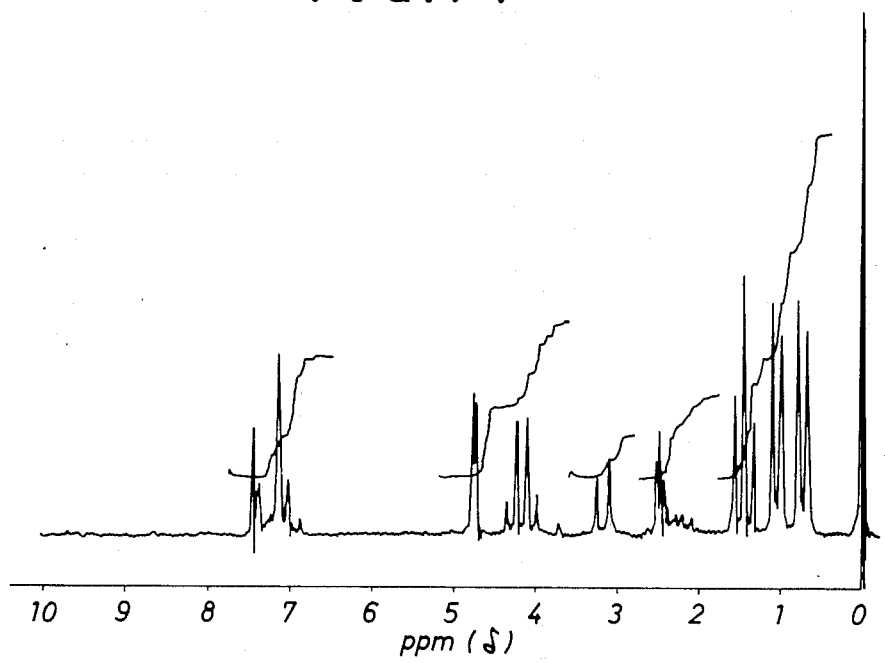

The infrared absorption spectrum of the thus obtained product and the nuclear magnetic resonance spectrum thereof (in CDCl$_3$ and TMS) are shown in FIGS. 31 and 72, respectively.

EXAMPLE 4

Synthesis of 2-butynyl 2-(3-fluoro-4-ethoxyphenyl)isovalerate (Compound No. 34)

Into a solution of 0.15 g (0.62 mM) of 2-(3-fluoro-4-ethoxyphenyl)isovaleric acid in 3.0 ml of anhydrous methylene chloride, a catalytic amount of dimethylformamide and 0.16 g (1.37 mM) of thionyl chloride were added, and the mixture was stirred for 2 hours in an oil bath at 40° C. Thereafter, an excess of thionyl chloride and methylene chloride were distilled off from the reaction mixture under a reduced pressure to obtain 2-(3-fluoro-4-ethoxyphenyl)isovaleric chloride as an oily substance.

After dissolving the thus obtained oily substance into 1.5 ml of anhydrous benzene, a solution of 0.0656 g (0.94 mM) of 2-butyn-1-ol in 1.5 ml of anhydrous benzene and 0.099 g of pyridine were added to the thus prepared solution, and the thus prepared mixture was stirred for one hour at room temperature.

Then, the reaction mixture was subjected to the same treatment as in Example 3, thereby 0.15 g of the compound No. 34 was obtained (yield: 80%).

Figure 34:
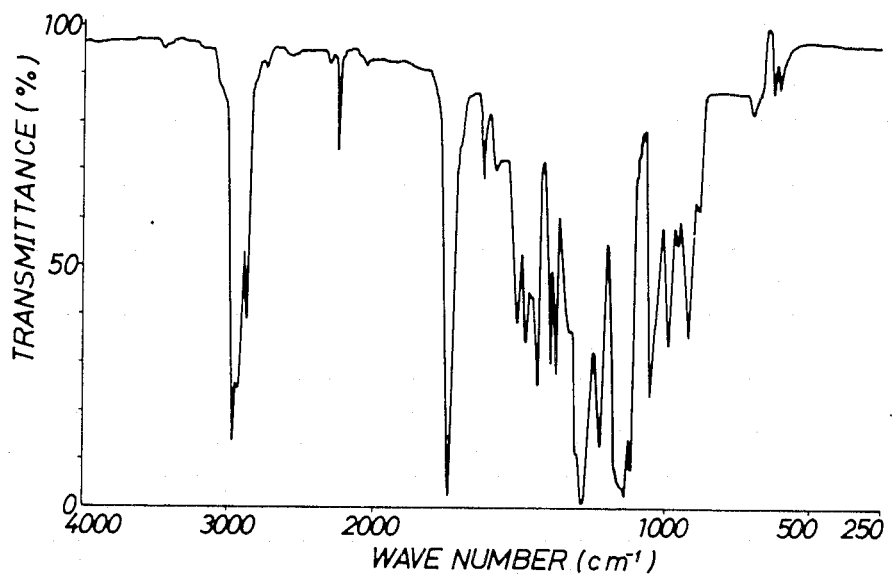
Figure 75:
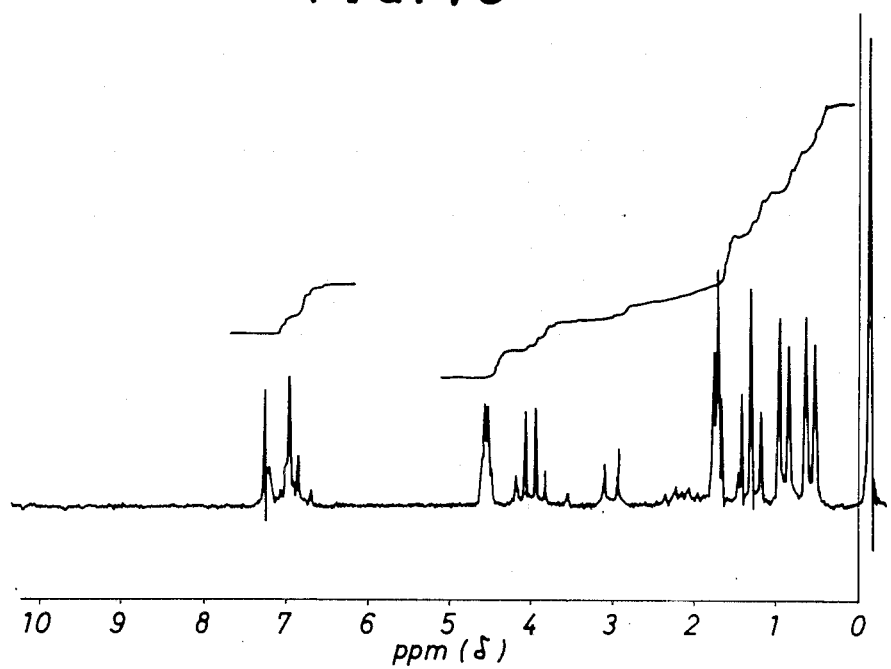

The infrared absorption spectrum of the thus obtained product and the nuclear magnetic resonance spectrum thereof (in CDCl$_3$ and TMS) are shown in FIGS. 34 and 75, respectively.

EXAMPLES 5 TO 25

In a similar manner to Example 1, compounds Nos. 2 to 22 to the present invention were produced, and their infrared absorption spectra (IR spectra) and nuclear magnetic resonance spectra (NMR spectra) are shown in FIGS. 2 to 22 (IR spectra) and FIGS. 43 to 63 (NMR spectra), respectively.

EXAMPLES 26 TO 33

In a similar manner to Example 2, compounds Nos. 23, 25 to 30 and 41 of the present invention were produced, and their infrared absorption spectra (IR spectra) and nuclear magnetic resonance spectra (NMR spectra) are shown in FIGS. 23, 25 to 30 and 41 (IR spectra) and FIGS. 64, 66 to 71 and 82 (NMR spectra), respectively.

EXAMPLE 34

Figure 35:
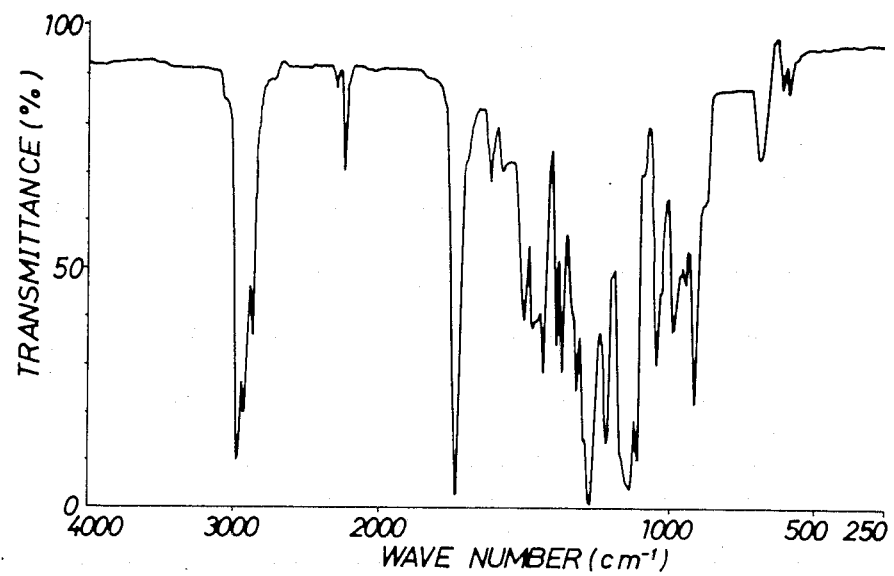
Figure 36:
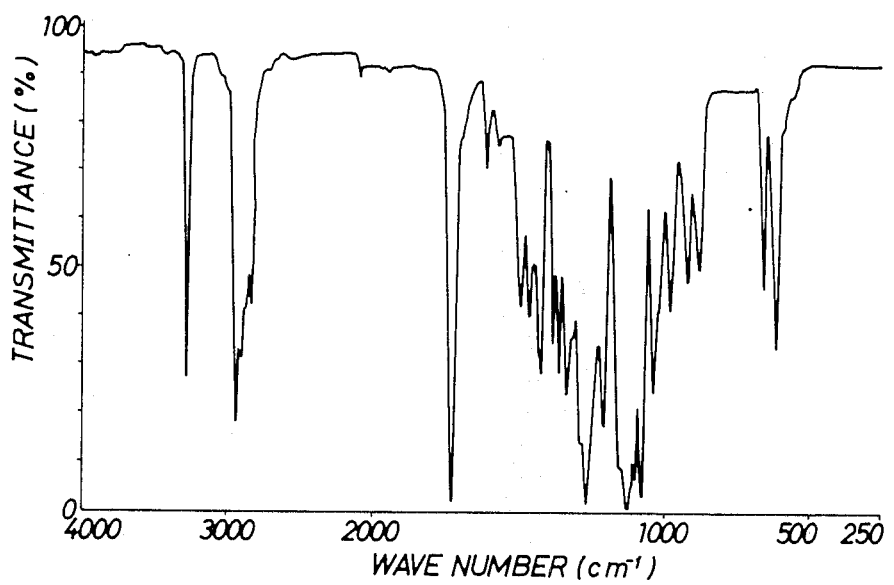
Figure 37:
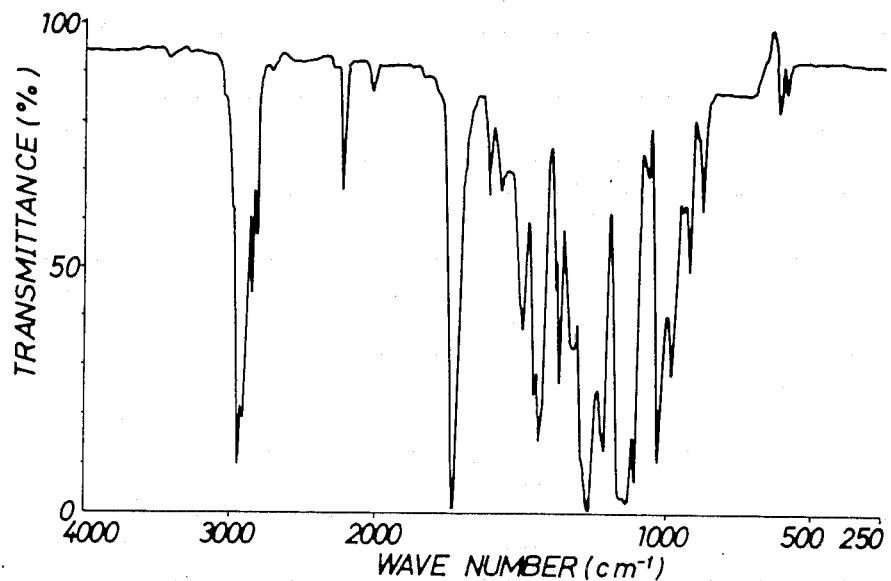
Figure 38:
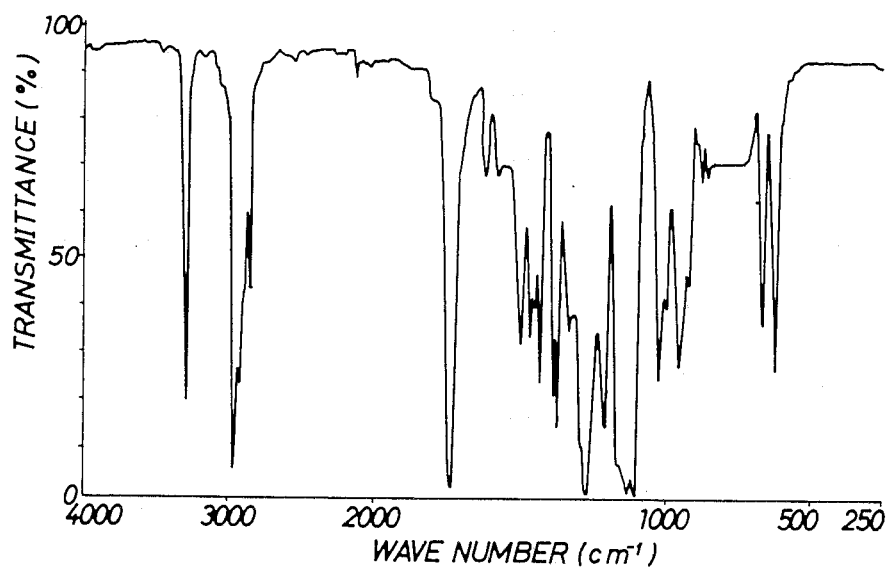
Figure 39:
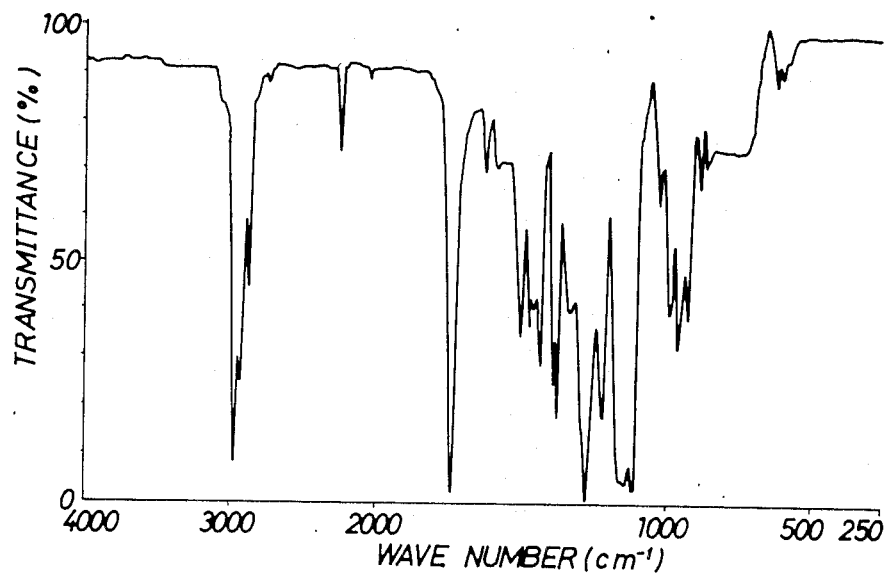
Figure 40:
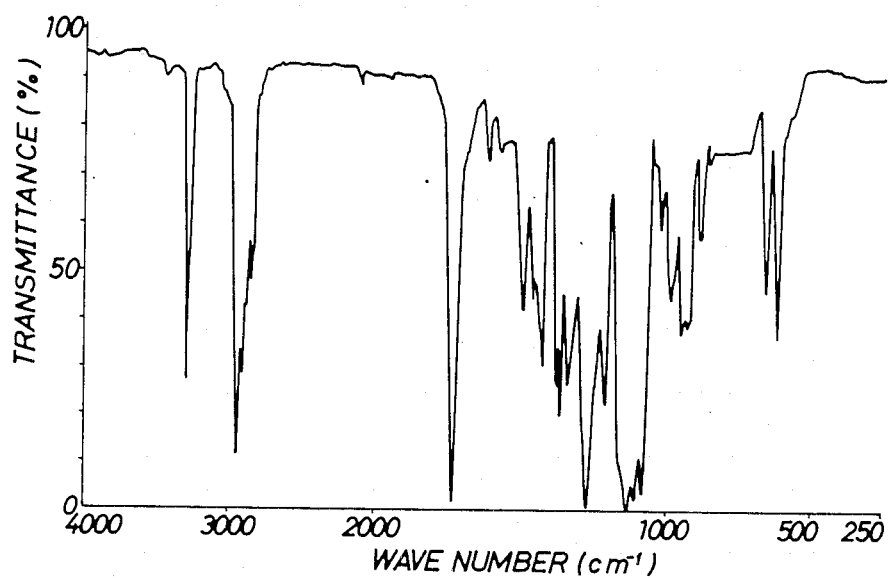
Figure 41:
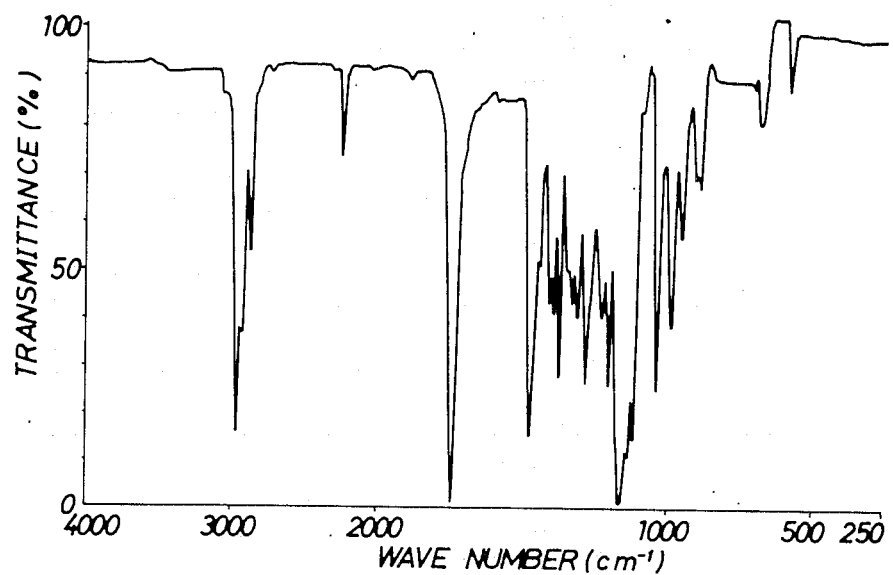
Figure 76:
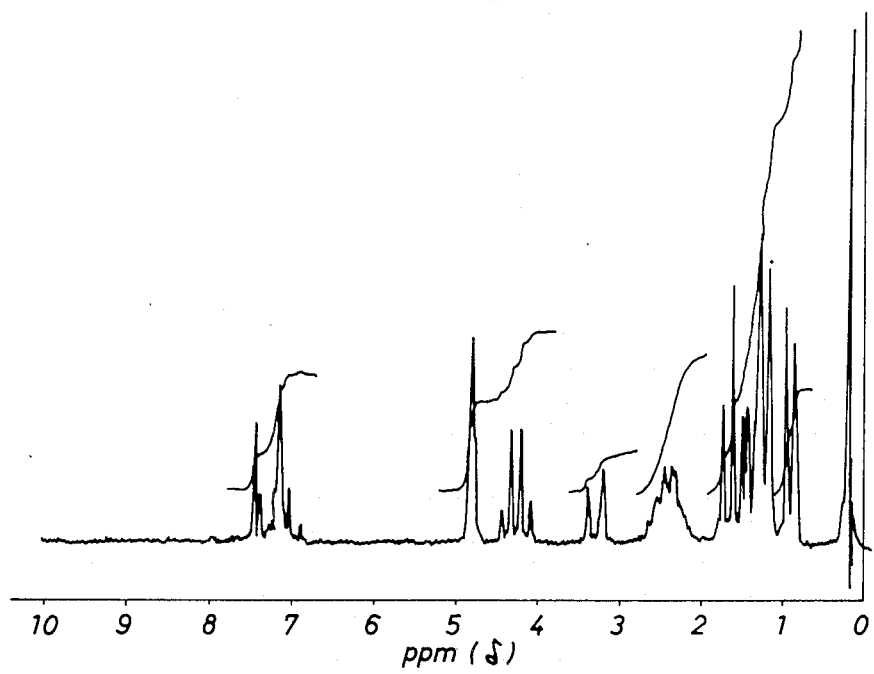
Figure 77:
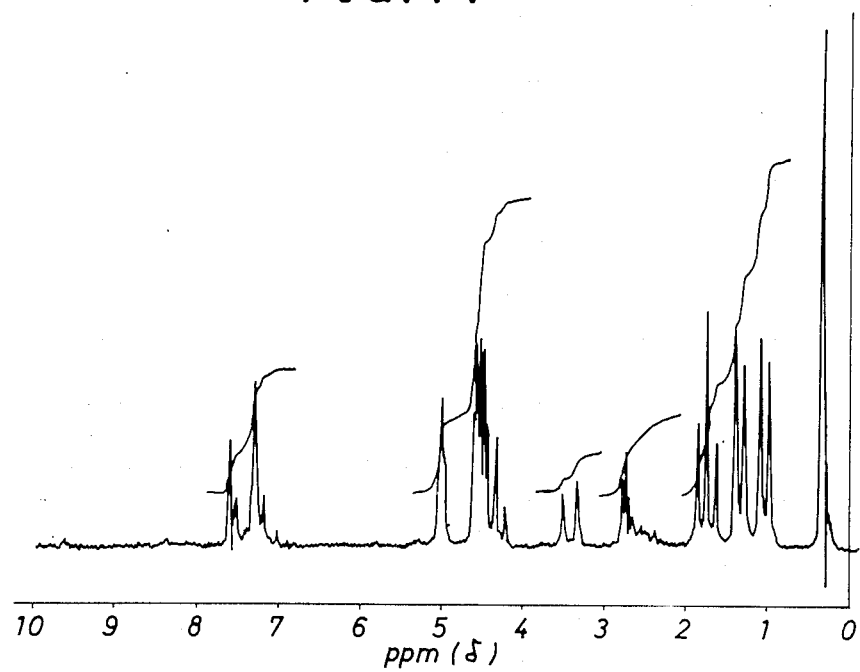
Figure 78:
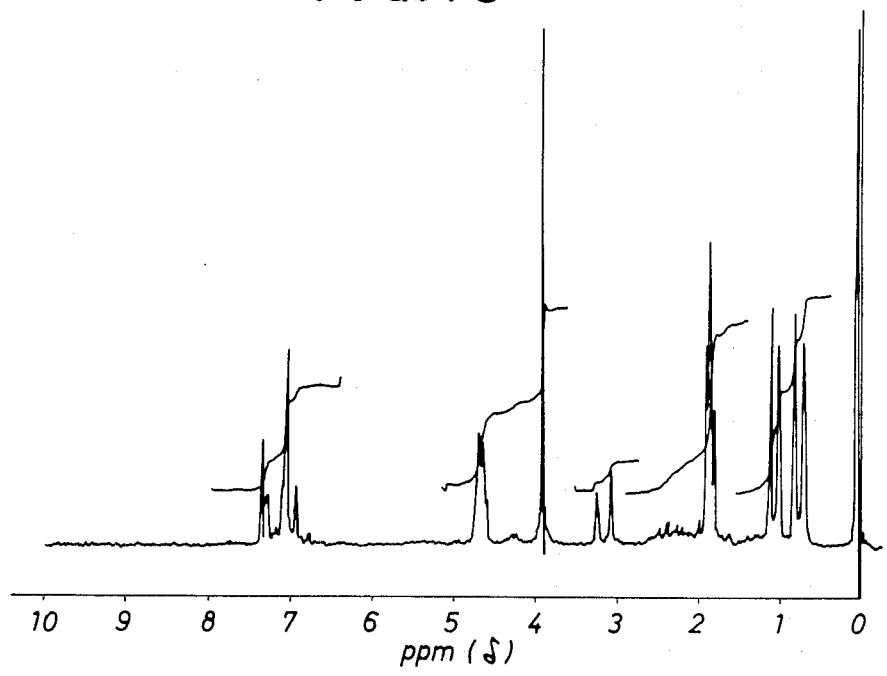
Figure 79:
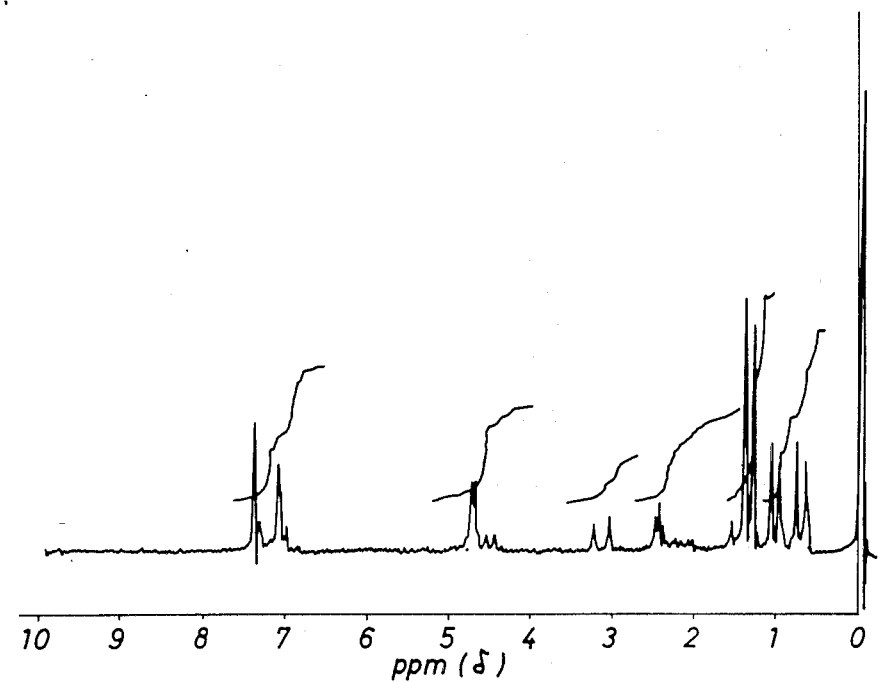
Figure 80:
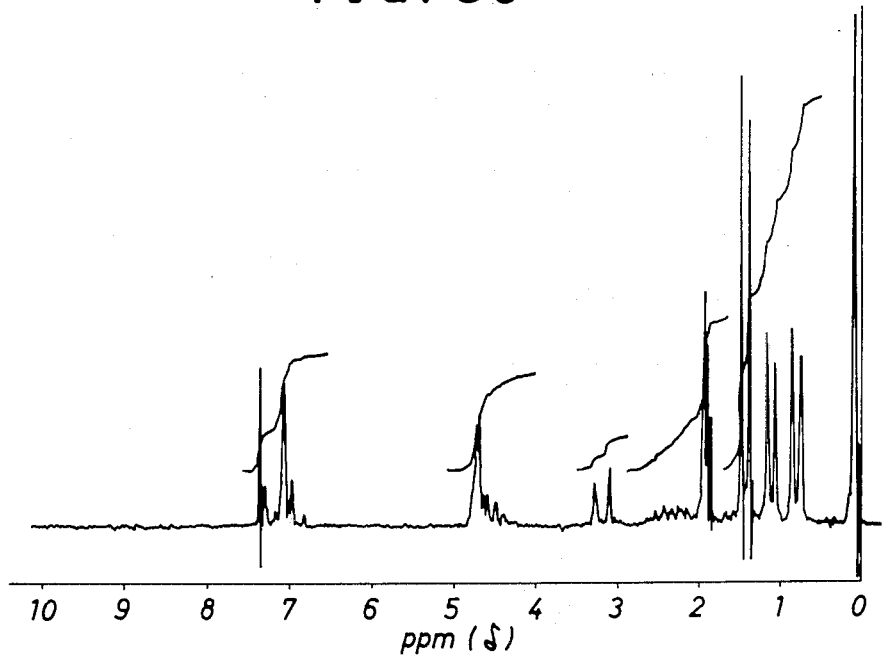
Figure 81:
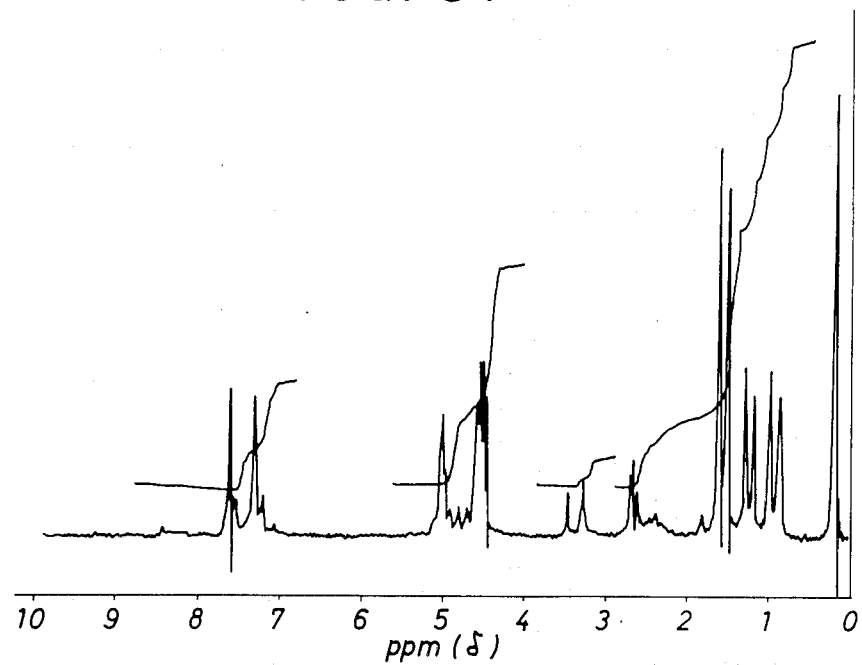
Figure 82:
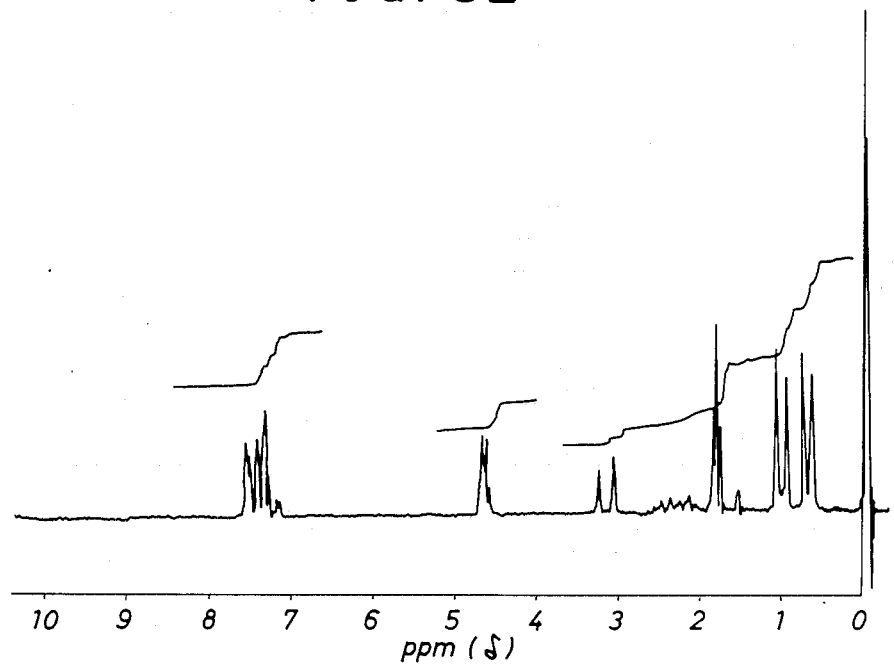

In a similar manner to Example 3, compound No. 32 to the present invention was produced, and the infrared absorption spectrum (IR spectrum) and nuclear magnetic resonance spectrum (NMR spectrum) are shown in FIG. 35 (IR spectrum) and FIG. 76 (NMR spectrum), respectively.

EXAMPLES 35 TO 41

In a similar manner to Example 4, compounds Nos. 33 and 35 to 40 of the present invention were produced, and their infrared absorption spectra (IR spectra) and nuclear magnetic resonance spectra (NMR spectra) are shown in FIGS. 33 and 35 to 40 (IR spectra) and FIGS. 74 and 76 to 81 (NMR spectra), respectively.

EXAMPLE 42

Preparation of Insecticidal Composition

Two kinds of solutions were prepared by exactly weighing one gram of each of the present compounds shown in Table 3 and dissolving the thus weighed compounds respectively into 5000 g, 2500 g and 1000 g of acetone.

EXAMPLE 43

Insecticidal test against Musca domestica by topical application

One μl of each of the insecticidal compositions of a solution-type prepared in Example 42 was applied dropwise on the back of the prothorax of each of sixty female adult *Musca domestica,* and thus treated insects were bred in a covered dish of 1.5 cm in height and 9.0 cm in diameter at 25° C. while being given an aqueous 5% sucrose solution.

After 24 hours of the treatment, mortality of the thus treated insects was observed. The results are shown in Table 3.

TABLE 3

| Present Compound No. | Mortality of Test Insects Mortality (%) | | |
|---|---|---|---|
| | 1,000 ppm | 400 ppm | 200 ppm |
| 1 | 100 | 60 | 0 |
| 2 | 100 | 100 | 70 |
| 3 | 100 | 100 | 20 |
| 5 | 100 | 60 | 30 |
| 8 | 100 | 100 | 50 |
| 13 | 100 | 60 | 0 |
| 14 | 100 | 60 | 10 |
| 23 | 100 | 70 | 10 |
| 24 | 100 | 100 | 70 |
| 26 | 100 | 100 | 70 |
| 27 | 100 | 20 | 0 |
| 29 | 100 | 100 | 60 |
| 30 | 100 | 80 | 40 |
| 31 | 100 | 90 | 20 |
| 32 | 100 | 60 | 10 |
| 33 | 100 | 50 | 20 |
| 34 | 100 | 100 | 100 |
| 35 | 100 | 60 | 30 |
| 36 | 100 | 100 | 100 |
| 37 | 100 | 100 | 50 |
| 38 | 100 | 70 | 10 |
| 39 | 100 | 100 | 70 |
| 40 | 100 | 90 | 40 |
| 41 | 80 | 30 | 0 |
| Allethrin* | 100 | 50 | 10 |

Note:
*a comparative insecticide

As are seen in Table 3, the present compounds tested showed higher insecticidal activity than allethrin at a concentration of as low as 200 ppm.

What is claimed is:

1. Derivatives of phenylisovaleric ester represented by the formula (I):

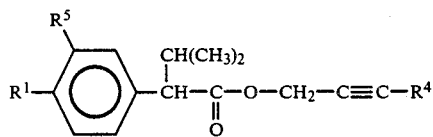

wherein $R^1$ represents a lower alkoxy group; $R^4$ represents a lower alkyl group,

—CH$_2$—CH=CH$_2$, —CH$_2$—CH=CH—CH$_3$,

—CH$_2$—C(CH$_3$)=CH$_2$, —CH$_2$OCH$_3$, —CH$_2$OCH$_2$CH$_3$,

—CH$_2$—O—CH$_2$—CH=CH$_2$, —CH$_2$—O—CH$_2$—C≡CH,
—CH$_2$—O—CH$_2$—C≡C—CH$_3$, —COCH$_3$,

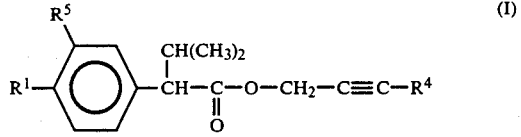

and $R^5$ represents a hydrogen atom or a halogen atom, and wherein (1) $R^4$ is not a methyl group when $R^1$ is an isopropoxy group and $R^5$ is a hydrogen atom, or when $R^1$ is a methoxy group and $R^5$ is a chlorine atom, (2) $R^4$ is not —CH$_2$—CH=CH$_2$ when $R^1$ is an ethoxy group and $R^5$ is a hydrogen atom, (3) $R^4$ is not —CH$_2$OCH$_2$C≡CH when $R^1$ is an ethoxy group and $R^5$ is a bromine atom and (4) $R^4$ is not an ethyl group when $R^1$ is an ethoxy group and $R^5$ is a fluorine atom.

2. 2-Butynyl 2-(4-ethoxyphenyl)isovalerate.

3. 2-Pentynyl 2-(4-ethoxyphenyl)isovalerate.

4. 4-(2-Propynyloxy)-2-butynyl 2-(4-ethoxyphenyl)isovalerate.

5. 2-Butynyl 2-(3-chloro-4-ethoxyphenyl)isovalerate.

6. 2-Butynyl 2-(3-chloro-4-isopropoxyphenyl)isovalerate.

7. 2-Butynyl 2-(3-fluoro-4-ethoxyphenyl)isovalerate.

8. 4-(2-Propynyloxy)-2-butynyl 2-(3-fluoro-4-ethoxyphenyl)isovalerate.

9. 2-Butynyl 2-(3-fluoro-4-isopropoxyphenyl)isovalerate.

10. 4-(2-Propynyloxy)-2-butyl 2-(3-chloro-4-ethoxyphenyl)isovalerate.

11. 2-Butynyl 2-(3-fluoro-4-methoxyphenyl)isovalerate.

12. A process for producing a derivative of phenylisovaleric ester represented by the formula (I):

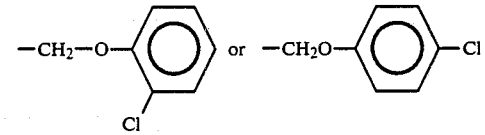

wherein $R^1$ represents a lower alkoxy group; $R^4$ represents a lower alkyl group,

—CH$_2$—CH=CH$_2$, —CH$_2$—CH=CH—CH$_3$,

—CH$_2$—C(CH$_3$)=CH$_2$, —CH$_2$OCH$_3$, —CH$_2$OCH$_2$CH$_3$,

—CH$_2$—O—CH$_2$—CH=CH$_2$, —CH$_2$—O—CH$_2$—C≡CH,

—CH$_2$—O—CH$_2$—C≡C—CH$_3$, —COCH$_3$,

—CH$_2$—O—COCH$_3$, —COOCH$_3$, —CH$_2$—O—⟨phenyl⟩,

—CH$_2$—O—⟨chlorophenyl⟩ or —CH$_2$O—⟨chlorophenyl⟩ and $R^5$ represents a hydrogen atom or a halogen atom, and wherein (1) $R^4$ is not a methyl group when $R^1$ is an isopropoxy group and $R^5$ is a hydrogen atom, or when $R^1$ is a methoxy group and $R^5$ is a chlorine atom, (2) $R^4$ is not —CH$_2$—CH=CH$_2$ when $R^1$ is an ethoxy group and $R^5$ is a hydrogen atom, (3) $R^4$ is not —CH$_2$OCH$_2$C≡CH when $R^1$ is an ethoxy group and $R^5$ is a bromine atom and (4) $R^4$ is not an ethyl group when $R^1$ is an ethoxy group and $R^5$ is a fluorine atom, comprising reacting carboxylic acid halide represented by the following formula (II):

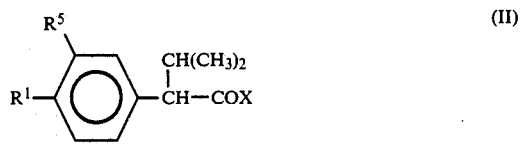

wherein $R^1$ and $R^5$ are the same as defined above and X represents a halogen atom, with an alcohol represented by the following formula (III):

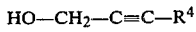

(III)

wherein $R^4$ is the same as defined above, in a solvent in the presence of a condensing agent.

13. The process according to claim 12, wherein said solvent is benzene, toluene, ethyl ether, dioxane, chloroform, methylene chloride or carbon tetrachloride.

14. The process according to claim 12, wherein said condensing agent is pyridine, triethylamine, sodium hydroxide, potassium hydroxide, sodium carbonate or potassium carbonate.

15. The process according to claim 12, wherein the reaction is carried out at a temperature of 0° to 100° C. for 1 to 24 hours.

16. An insecticidal composition comprising an insecticidally effective amount of at least one of the derivatives of phenylisovaleric ester represented by the formula (I) as an active ingredient:

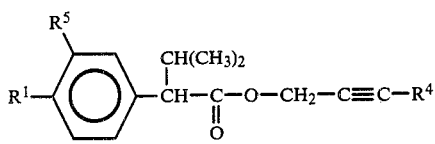

(I)

wherein $R^1$ represents a lower alkoxy group; $R^4$ represents a lower alkyl group,

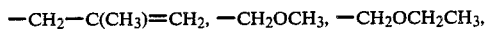

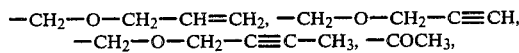

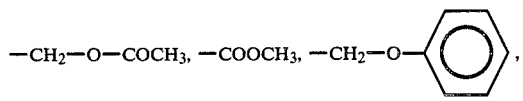

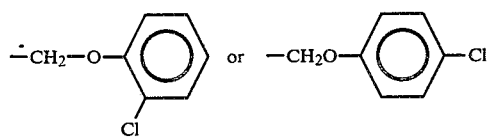

and $R^5$ represents a hydrogen atom or a halogen atom, and wherein (1) $R^4$ is not a methyl group when $R^1$ is an isopropoxy group and $R^5$ is a hydrogen atom, or when $R^1$ is a methoxy group and $R^5$ is a chlorine atom, (2) $R^4$ is not —CH$_2$—CH=CH$_2$ when $R^1$ is an ethoxy group and $R^5$ is a hydrogen atom, (3) $R^4$ is not —CH$_2$OCH$_2$C≡CH when $R^1$ is an ethoxy group and $R^5$ is a bromine atom and (4) $R^4$ is not an ethyl group when $R^1$ is an ethoxy group and $R^5$ is a fluorine atom, an insecticidally acceptable carrier and a diluent therefor.

17. The insecticidal composition according to claim 16, wherein said derivative is 2-butynyl 2-(4-ethoxyphenyl)isovalerate.

18. The insecticidal composition according to claim 16, wherein said derivative is 2-pentynyl 2-(4-ethoxyphenyl)isovalerate.

19. The insecticidal composition according to claim 16, wherein said derivative is 4-(2-propynyloxy)-2-butynyl 2-(4-ethoxyphenyl)isovalerate.

20. The insecticidal composition according to claim 16, wherein said derivative is 2-butynyl 2-(3-chloro-4-ethoxyphenyl)isovalerate.

21. The insecticidal composition according to claim 16, wherein said derivative is 2-butynyl 2-(3-chloro-4-isopropoxyphenyl)isovalerate.

22. The insecticidal composition according to claim 16, wherein said derivative is 2-butynyl 2-(3-fluoro-4-ethoxyphenyl)isovalerate.

23. The insecticidal composition according to claim 16, wherein said derivative is 4-(2-propynyloxy)-2-butynyl 2-(3-fluoro-4-ethoxyphenyl)isovalerate.

24. The insecticidal composition according to claim 16, wherein said derivative is 2-butynyl 2-(3-fluoro-4-isopropoxyphenyl)isovalerate.

25. The insecticidal composition according to claim 16, wherein said derivative is 4-(2-propynyloxy)-2-butynyl 2-(3-chloro-4-ethoxyphenyl)isovalerate.

26. The insecticidal composition according to claim 16, wherein said derivative is 2-butynyl 2-(3-fluoro-4-methoxyphenyl)isovalerate.

27. A method for controlling noxious insects, which comprises applying an insecticidally effective amount of a derivative of phenylisovaleric ester represented by the formula (I):

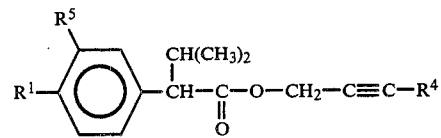

(I)

wherein $R^1$ represents a lower alkoxy group; $R^4$ represents a lower alkyl group,

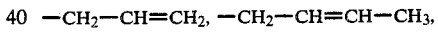

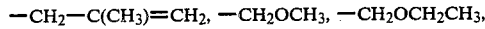

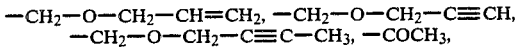

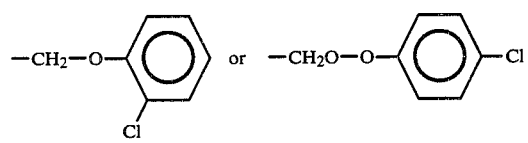

and $R^5$ represents a hydrogen atom or a halogen atom, and wherein (1) $R^4$ is not a methyl group when $R^1$ is an isopropoxy group and $R^5$ is a hydrogen atom, or when $R^1$ is a methoxy group and $R^5$ is a chlorine atom, (2) $R^4$ is not —CH$_2$—CH=CH$_2$ when $R^1$ is an ethoxy group and $R^5$ is a hydrogen atom, (3) $R^4$ is not —CH$_2$OCH$_2$C≡CH when $R^1$ is an ethoxy group and $R^5$ is a bromine atom and (4) $R^4$ is not an ethyl group when $R^1$ is an ethoxy group and $R^5$ is a fluorine atom.

28. The method for controlling noxious insects according to claim 27, wherein said derivative is 2-butynyl 2-(4-ethoxyphenyl)isovalerate.

29. The method for controlling noxious insects according to claim 27, wherein said derivative is 2-pentynyl 2-(4-ethoxyphenyl)isovalerate.

30. The method for controlling noxious insects according to claim 27, wherein said derivative is 4-(2-propynyloxy)-2-butynyl 2-(4-ethoxyphenyl)isovalerate.

31. The method for controlling noxious insects according to claim 27, wherein said derivative is 2-butynyl 2-(3-chloro-4-ethoxyphenyl)isovalerate.

32. The method for controlling noxious insects according to claim 27, wherein said derivative is 2-butynyl 2-(3-chloro-4-isopropoxyphenyl)isovalerate.

33. The method for controlling noxious insects according to claim 27, wherein said derivative is 2-butynyl 2-(3-fluoro-4-ethoxyphenyl)isovalerate.

34. The method for controlling noxious insects according to claim 27, wherein said derivative is 4-(2-propynyloxy) 2-butynyl 2-(3-fluoro-4-ethoxyphenyl)isovalerate.

35. The method for controlling noxious insects according to claim 27, wherein said derivative is 2-butynyl 2-(3-fluoro-4-isopropoxyphenyl)isovalerate.

36. The method for controlling noxious insects according to claim 27, wherein said derivative is 4-(2propynyloxy)-2-butynyl 2-(3-chloro-4-ethoxyphenyl)isovalerate.

37. The method for controlling noxious insects according to claim 27, wherein said derivative is 2-butynyl 2-(3-fluoro-4-methoxyphenyl)isovalerate.

* * * * *